US007442370B2

(12) United States Patent
Sah et al.

(10) Patent No.: US 7,442,370 B2
(45) Date of Patent: Oct. 28, 2008

(54) POLYMER CONJUGATES OF MUTATED NEUBLASTIN

(75) Inventors: Dinah Wen-Yee Sah, Boston, MA (US); R. Blake Pepinsky, Arlington, MA (US); Paula Ann Boriack-Sjodin, Waltham, MA (US); Stephan S. Miller, Arlington, MA (US); Anthony Rossomando, Revere, MA (US); Laura Silvian, Waban, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 310 days.

(21) Appl. No.: 10/356,264

(22) Filed: Jan. 31, 2003

(65) Prior Publication Data
US 2005/0142098 A1 Jun. 30, 2005

Related U.S. Application Data

(63) Continuation-in-part of application No. PCT/US02/02319, filed on Jan. 25, 2002.

(60) Provisional application No. 60/266,071, filed on Feb. 1, 2001.

(51) Int. Cl.
*A61K 38/18* (2006.01)
*A61K 31/74* (2006.01)
*C07K 14/475* (2006.01)
*C08G 63/48* (2006.01)
*C08G 63/91* (2006.01)

(52) U.S. Cl. .................. 424/78.27; 514/12; 525/54.1; 530/399

(58) Field of Classification Search .................. None
See application file for complete search history.

(56) References Cited

U.S. PATENT DOCUMENTS

| | | | |
|---|---|---|---|
| 4,883,666 A | 11/1989 | Sabel et al. | |
| 5,084,350 A | 1/1992 | Chang et al. | |
| 5,194,596 A * | 3/1993 | Tischer et al. | 530/399 |
| 5,284,761 A | 2/1994 | Aebischer et al. | |
| 5,350,836 A * | 9/1994 | Kopchick et al. | 530/399 |
| 5,414,135 A * | 5/1995 | Snow et al. | 568/29 |
| 5,496,804 A | 3/1996 | Reed et al. | |
| 5,618,531 A | 4/1997 | Cherksey | |
| 5,733,729 A | 3/1998 | Lipshutz et al. | |
| 5,754,524 A | 5/1998 | Wark | |
| 5,770,577 A | 6/1998 | Fandl et al. | |
| 5,795,716 A | 8/1998 | Chee et al. | |
| 5,800,992 A | 9/1998 | Fodor et al. | |
| 5,834,029 A | 11/1998 | Bellamkonda et al. | |
| 5,846,935 A | 12/1998 | Panayotatos | |
| 5,916,555 A | 6/1999 | Lee et al. | |
| 5,939,524 A * | 8/1999 | Bowditch et al. | 530/324 |
| 6,284,540 B1 * | 9/2001 | Milbrandt et al. | 435/455 |
| 6,593,133 B1 | 7/2003 | Johansen et al. | |
| 6,734,284 B1 | 5/2004 | Johansen et al. | |
| 2002/0055467 A1 | 5/2002 | Johansen et al. | |
| 2004/0077543 A1 | 4/2004 | Sah et al. | |
| 2004/0142418 A1 | 7/2004 | Sah et al. | |
| 2004/0265972 A1 | 12/2004 | Weintraub et al. | |

FOREIGN PATENT DOCUMENTS

| | | |
|---|---|---|
| WO | WO 93/06116 | 4/1993 |
| WO | WO 97/08196 | 3/1997 |
| WO | WO 97/11964 | 4/1997 |
| WO | WO 98/32869 | 7/1998 |
| WO | WO 99/03887 | 1/1999 |
| WO | WO 99/43813 | 9/1999 |
| WO | WO 00/01815 | 1/2000 |
| WO | WO 00/04050 | 1/2000 |
| WO | WO 00/18799 | 4/2000 |
| WO | WO 00/34475 | 6/2000 |
| WO | WO 00/73348 | 12/2000 |
| WO | WO 02/051433 | 7/2002 |
| WO | WO 02/060929 | 8/2002 |
| WO | WO 02/072826 | 9/2002 |
| WO | WO 02/078730 | 10/2002 |

OTHER PUBLICATIONS

Vukicevic et al., 1996, PNAS USA 93:9021-9026.*
Baudet et al., Development 127:4335-4344, 2000.*
Choh, PNAS 77(6):3211-14, 1990.*
Skolnick et al., 18(1):34-39, 2000.*
Watabe et al., J. Neurosci. Res., 41:279-90, 1995.*
Matsushita et al., Gene 203, 149-157, 1997.*
PIR_80 Accession No. 14968.*
Lin et al., Science 260(5111):1130-32, May 21, 1993.*
Airaksmen et al. (1999), GDNF family neurotrophic factor signaling: four masters, one servant, *Mol Cell Neurosci*, 13:313-325.
Atschul et al. (1997), "Gapped BLAST and PSI-BLAST: a new generation of protein database search programs," *Nucl. Acids Res.*, 25:3389-3402.
Baloh, R.H. et al. (1998), "Artemm, a novel member of the GDNF ligand family, supports peripheral and central neurons and signals through the GFRα3-RET receptor complex," *Neuron*, 21:1291-1302.
Baloh, R.H. et al. (2000), "Functional mapping of receptor specificity domains of glial cell line-derived neurotrophic factor (GDNF) family ligands and production of GFRalphaI RET-specific agonists," *Journal of biological Chemistry*, 275(5):3412-3420.
Borodovsky et al. (1995), "Detection of new genes in a bacterial genome using Markov models for three gene classes," *Nucl. Acids Res.*, 23:3554-3562.
Daopin et al. (1993), "Chrystal structure of TGF-β2 refined at 1.8 A resolution," *Proteins*, 17:176-192.

(Continued)

*Primary Examiner*—Elizabeth C. Kemmerer
*Assistant Examiner*—Gregory S. Emch
(74) *Attorney, Agent, or Firm*—Fish & Richardson P.C.

(57) ABSTRACT

A dimer comprising a mutated neublastin polypeptide coupled to a polymer is disclosed. Such dimers exhibit prolonged bioavailability and, in preferred embodiments, prolonged biological activity relative to wild-type forms of neublastin.

68 Claims, No Drawings

OTHER PUBLICATIONS

Delgado, C. et al., (1992), "The uses and properties of PEG-Linked proteins," *Critical Reviews in Therapeutic Drug Carrier Systems*, 9(3/4):249-304.

Eigenbrot and Gerber (1997), "X-ray structure of glial cell-derived neurotrophic factor at 1 9 A resolution and implications for receptor binding," *Nat. Struct. Biol.*, 4:435-438.

Finsen et al. (1992), "Somatostatin and neuropeptide Y in organotypic slice cultures of the rat hippocampus: an immunocytochemical and in situ hybridization study," *Neurosci*, 47:105-113.

Francis, G.E., et al., (1998), "Pegylation of Cytokines and other therapeutic proteins and peptides: the importance of biological optimization of coupling techniques," *Int'l. Journal of Hematology, Elsevier Science Publishers*, NL., 68(1):1-18.

GenBank™ Accession No. AA844072 (1998).

Lapchak (1977), "Therapeutic potential for glial cell line-derived neurotropic factor (GDNF) based upon pharmacological activities in the CNS," *Rev. Neurosci.*, 7:165-176).

Lapchak et al. (1996), "Pharmacological characterization of glial cell line-derived neurotrophic factor (GDNF): implications for GDNF as a therapeutic molecule for treating neurodegenerative diseases," *Cell Tissue Res.*, 286:179-189.

Lin et al. (1993), GDNF: A glial cell line-derived neurotrophic factor for midbrain dopaminergic neurons, *Science*, 260:1130-1132.

Lorenz et al. (1996), "Heteromultimeric CLC chloride channels with novel properties," *Proc. Natl. Acad. Sci USA*, 93: 13362-13366.

Massague et al. (1994), "The TGF-β family and its composite receptor," *Trends Cell Biol.*, 4:172-178.

Masure et al. (1999), "Enovin, a member of the glial cell-line-derived neurotrophic factor (GDNF) family with growth promoting activity on neuronal cells," *Eur. J. Biochem*, 266:892-902.

McDonald and Hendrickson (1993), "A structural superfamily of growth factors containing a cystine knot motif.," *Cell*, 73:421-424.

Milbrandt et al. (1998), Persephin, a novel neurotrophic factor related to GDNF and neurturin, *Neuron*, 20:245-253.

Reddy, K.R. (2000), "Controlled-release peylation, liposomal formulations: new mechanisms in the delivery of injectable drugs," *Annals of Pharmacotherapy*, 34(7/8):915-923.

Robertson and Manson (1997), "The GDNF-RET signaling in partnership," *Trends Genet.*, 13:1-3.

Saarma and Sariola (1999), *Microscopy Res. & Technique*, 45:292-302.

Sanicola et al. (1997), "Glial cell line-derived neurotrophic factor-dependent RET activation can be mediated by two different cell-surface accessory proteins," *Proc Natl Acad Sci USA*, 94:6238-6243.

Sauer and Oertel (1994), "Progressive degeneration of nigrostriatal dopamine neurons following intrastraiatal terminal lesions with 6-hydroxydopamine: a combined retrograde tracing and immunocytochemical study in the rat," *Neuroscience*, 59:401-415.

Slooth and Gramsbergen (1995), "Detection of salicylate and its hydroxylated adducts 2.3- and 2.5- dihydroxybenzoic acids as possible indices for in vivo hydroxyl radical formation in combination with catechol- and indoleamines and their metabolites in cerebrospinal fluid and brain tissue," *J. Neurosci. Meth.*, 60:141-149.

Stoppini et al. (1991), "A simple method for organotypic cultures of nervous tissue," *J. Neurosci. Methods*, 37:173-182.

Thompson et al. (1997), "The ClustalX windows interface: flexible strategies for multiple sequence alignment aided by quality analysis tools," *Nucl. Acids Res.*, 25:4876-4882.

Unsicker (1996), "GDNF: a cytokine at the interface of TGF-betas and neurotrophins," *Cell Tissue Res.*, 286:175-178.

Von Schwedler et al. (1993), "Vif is crucial for human immunodeficiency virus type 1 proviral DNA synthesis in infected cells," *J. Virol.*, 67:4945-4955.

Zufferey et al. (1997), "Multiply attenuated lentiviral vector achieves efficient gene delivery in vivo," *Nat. Biotechnol.*, 15:871-875.

Rosenblad, C., et al., "In Vivo Protection of Nigral Dopamine Neurons by Lentiviral Gene Transfer of the Novel GDNF-Family Member Neublastin/Artemin," *Molecular and Cellular Neuroscience* 15:199-214 (2000).

\* cited by examiner

```
                        SEQUENCE LISTING

<160> NUMBER OF SEQ ID NOS: 36

<210> SEQ ID NO 1
<211> LENGTH: 113
<212> TYPE: PRT
<213> ORGANISM: Artificial Sequence
<220> FEATURE:
<223> OTHER INFORMATION: mature neublastin consensus sequence
<220> FEATURE:
<221> NAME/KEY: VARIANT
<222> LOCATION: 3
<223> OTHER INFORMATION: Xaa = Gly or Thr
<220> FEATURE:
<221> NAME/KEY: VARIANT
<222> LOCATION: 4
<223> OTHER INFORMATION: Xaa = Pro or Arg
<220> FEATURE:
<221> NAME/KEY: VARIANT
<222> LOCATION: 5
<223> OTHER INFORMATION: Xaa = Gly or Ser
<220> FEATURE:
<221> NAME/KEY: VARIANT
<222> LOCATION: 10, 11
<223> OTHER INFORMATION: Xaa = Ala or Thr
<220> FEATURE:
<221> NAME/KEY: VARIANT
<222> LOCATION: 12
<223> OTHER INFORMATION: Xaa = Gly or Asp
<220> FEATURE:
<221> NAME/KEY: VARIANT
<222> LOCATION: 26, 33
<223> OTHER INFORMATION: Xaa = Arg or Ser
<220> FEATURE:
<221> NAME/KEY: VARIANT
<222> LOCATION: 38, 76
<223> OTHER INFORMATION: Xaa = Val or Ile
<220> FEATURE:
<221> NAME/KEY: VARIANT
<222> LOCATION: 53
<223> OTHER INFORMATION: Xaa = Pro or Gln
<220> FEATURE:
<221> NAME/KEY: VARIANT
<222> LOCATION: 69
<223> OTHER INFORMATION: Xaa = Pro or Ser
<220> FEATURE:
<221> NAME/KEY: VARIANT
<222> LOCATION: 103
<223> OTHER INFORMATION: Xaa = Arg or His

<400> SEQUENCE: 1

Ala Gly Xaa Xaa Xaa Ser Arg Ala Arg Xaa Xaa Xaa Ala Arg Gly Cys
 1               5                  10                  15

Arg Leu Arg Ser Gln Leu Val Pro Val Xaa Ala Leu Gly Leu Gly His
            20                  25                  30

Xaa Ser Asp Glu Leu Xaa Arg Phe Arg Phe Cys Ser Gly Ser Cys Arg
        35                  40                  45

Arg Ala Arg Ser Xaa His Asp Leu Ser Leu Ala Ser Leu Leu Gly Ala
 50                  55                  60

Gly Ala Leu Arg Xaa Pro Pro Gly Ser Arg Pro Xaa Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Xaa Leu Ser Ala Thr Ala Cys Gly Cys Leu
            100                 105                 110

Gly

<210> SEQ ID NO 2
```

```
<211> LENGTH: 113
<212> TYPE: PRT
<213> ORGANISM: Homo sapiens
<220> FEATURE:
<221> NAME/KEY: VARIANT
<222> LOCATION: (1)...(113)
<223> OTHER INFORMATION: mature NBN113

<400> SEQUENCE: 2

Ala Gly Gly Pro Gly Ser Arg Ala Arg Ala Gly Ala Arg Gly Cys
 1               5                  10                  15

Arg Leu Arg Ser Gln Leu Val Pro Val Arg Ala Leu Gly Leu Gly His
                20                  25                  30

Arg Ser Asp Glu Leu Val Arg Phe Arg Phe Cys Ser Gly Ser Cys Arg
            35                  40                  45

Arg Ala Arg Ser Pro His Asp Leu Ser Leu Ala Ser Leu Leu Gly Ala
        50                  55                  60

Gly Ala Leu Arg Pro Pro Gly Ser Arg Pro Val Ser Gln Pro Cys
 65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
                100                 105                 110

Gly

<210> SEQ ID NO 3
<211> LENGTH: 113
<212> TYPE: PRT
<213> ORGANISM: Mus musculus
<220> FEATURE:
<221> NAME/KEY: VARIANT
<222> LOCATION: (1)...(113)
<223> OTHER INFORMATION: mature NBN113

<400> SEQUENCE: 3

Ala Gly Thr Arg Ser Ser Arg Ala Arg Thr Thr Asp Ala Arg Gly Cys
 1               5                  10                  15

Arg Leu Arg Ser Gln Leu Val Pro Val Ser Ala Leu Gly Leu Gly His
                20                  25                  30

Ser Ser Asp Glu Leu Ile Arg Phe Arg Phe Cys Ser Gly Ser Cys Arg
            35                  40                  45

Arg Ala Arg Ser Gln His Asp Leu Ser Leu Ala Ser Leu Leu Gly Ala
        50                  55                  60

Gly Ala Leu Arg Ser Pro Gly Ser Arg Pro Ile Ser Gln Pro Cys
 65                  70                  75                  80

Cys Arg Pro Thr Arg Tyr Glu Ala Val Ser Phe Met Asp Val Asn Ser
                85                  90                  95

Thr Trp Arg Thr Val Asp His Leu Ser Ala Thr Ala Cys Gly Cys Leu
                100                 105                 110

Gly

<210> SEQ ID NO 4
<211> LENGTH: 113
<212> TYPE: PRT
<213> ORGANISM: Rattus norvegicus
<220> FEATURE:
<221> NAME/KEY: VARIANT
<222> LOCATION: (1)...(113)
<223> OTHER INFORMATION: mature NBN113

<400> SEQUENCE: 4
```

```
Ala Gly Thr Arg Ser Ser Arg Ala Arg Ala Thr Asp Ala Arg Gly Cys
  1               5                  10                  15

Arg Leu Arg Ser Gln Leu Val Pro Val Ser Ala Leu Gly Leu Gly His
             20                  25                  30

Ser Ser Asp Glu Leu Ile Arg Phe Arg Phe Cys Ser Gly Ser Cys Arg
             35                  40                  45

Arg Ala Arg Ser Pro His Asp Leu Ser Leu Ala Ser Leu Leu Gly Ala
         50                  55                  60

Gly Ala Leu Arg Ser Pro Gly Ser Arg Pro Ile Ser Gln Pro Cys
 65                  70                  75                  80

Cys Arg Pro Thr Arg Tyr Glu Ala Val Ser Phe Met Asp Val Asn Ser
                 85                  90                  95

Thr Trp Arg Thr Val Asp His Leu Ser Ala Thr Ala Cys Gly Cys Leu
                100                 105                 110

Gly

<210> SEQ ID NO 5
<211> LENGTH: 220
<212> TYPE: PRT
<213> ORGANISM: Homo sapiens

<400> SEQUENCE: 5

Met Glu Leu Gly Leu Gly Gly Leu Ser Thr Leu Ser His Cys Pro Trp
  1               5                  10                  15

Pro Arg Arg Gln Pro Ala Leu Trp Pro Thr Leu Ala Ala Leu Ala Leu
             20                  25                  30

Leu Ser Ser Val Ala Glu Ala Ser Leu Gly Ser Ala Pro Arg Ser Pro
             35                  40                  45

Ala Pro Arg Glu Gly Pro Pro Val Leu Ala Ser Pro Ala Gly His
         50                  55                  60

Leu Pro Gly Gly Arg Thr Ala Arg Trp Cys Ser Gly Arg Ala Arg Arg
 65                  70                  75                  80

Pro Pro Pro Gln Pro Ser Arg Pro Ala Pro Pro Pro Ala Pro Pro
                 85                  90                  95

Ser Ala Leu Pro Arg Gly Gly Arg Ala Ala Arg Ala Gly Gly Pro Gly
                100                 105                 110

Ser Arg Ala Arg Ala Ala Gly Ala Arg Gly Cys Arg Leu Arg Ser Gln
            115                 120                 125

Leu Val Pro Val Arg Ala Leu Gly Leu Gly His Arg Ser Asp Glu Leu
        130                 135                 140

Val Arg Phe Arg Phe Cys Ser Gly Ser Cys Arg Arg Ala Arg Ser Pro
145                 150                 155                 160

His Asp Leu Ser Leu Ala Ser Leu Leu Gly Ala Gly Ala Leu Arg Pro
                165                 170                 175

Pro Pro Gly Ser Arg Pro Val Ser Gln Pro Cys Cys Arg Pro Thr Arg
                180                 185                 190

Tyr Glu Ala Val Ser Phe Met Asp Val Asn Ser Thr Trp Arg Thr Val
            195                 200                 205

Asp Arg Leu Ser Ala Thr Ala Cys Gly Cys Leu Gly
        210                 215                 220

<210> SEQ ID NO 6
<211> LENGTH: 140
<212> TYPE: PRT
<213> ORGANISM: Homo sapiens
```

```
<220> FEATURE:
<221> NAME/KEY: VARIANT
<222> LOCATION: (1)...(140)
<223> OTHER INFORMATION: mature neublastin (NBN140)

<400> SEQUENCE: 6

Pro Pro Pro Gln Pro Ser Arg Pro Ala Pro Pro Pro Ala Pro Pro
1               5                   10                  15

Ser Ala Leu Pro Arg Gly Gly Arg Ala Ala Arg Ala Gly Pro Gly
                20                  25                  30

Ser Arg Ala Arg Ala Ala Gly Ala Arg Gly Cys Arg Leu Arg Ser Gln
                35                  40                  45

Leu Val Pro Val Arg Ala Leu Gly Leu Gly His Arg Ser Asp Glu Leu
    50                  55                  60

Val Arg Phe Arg Phe Cys Ser Gly Ser Cys Arg Arg Ala Arg Ser Pro
65                  70                  75                  80

His Asp Leu Ser Leu Ala Ser Leu Leu Gly Ala Gly Ala Leu Arg Pro
                85                  90                  95

Pro Pro Gly Ser Arg Pro Val Ser Gln Pro Cys Cys Arg Pro Thr Arg
                100                 105                 110

Tyr Glu Ala Val Ser Phe Met Asp Val Asn Ser Thr Trp Arg Thr Val
                115                 120                 125

Asp Arg Leu Ser Ala Thr Ala Cys Gly Cys Leu Gly
    130                 135                 140

<210> SEQ ID NO 7
<211> LENGTH: 116
<212> TYPE: PRT
<213> ORGANISM: Homo sapiens
<220> FEATURE:
<221> NAME/KEY: VARIANT
<222> LOCATION: (1)...(116)
<223> OTHER INFORMATION: mutated neublastin (NBN116)

<400> SEQUENCE: 7

Ala Ala Arg Ala Gly Gly Pro Gly Ser Arg Ala Arg Ala Ala Gly Ala
1               5                   10                  15

Arg Gly Cys Arg Leu Arg Ser Gln Leu Val Pro Val Arg Ala Leu Gly
                20                  25                  30

Leu Gly His Arg Ser Asp Glu Leu Val Arg Phe Arg Phe Cys Ser Gly
                35                  40                  45

Ser Cys Arg Arg Ala Arg Ser Pro His Asp Leu Ser Leu Ala Ser Leu
    50                  55                  60

Leu Gly Ala Gly Ala Leu Arg Pro Pro Pro Gly Ser Arg Pro Val Ser
65                  70                  75                  80

Gln Pro Cys Cys Arg Pro Thr Arg Tyr Glu Ala Val Ser Phe Met Asp
                85                  90                  95

Val Asn Ser Thr Trp Arg Thr Val Asp Arg Leu Ser Ala Thr Ala Cys
                100                 105                 110

Gly Cys Leu Gly
        115

<210> SEQ ID NO 8
<211> LENGTH: 112
<212> TYPE: PRT
<213> ORGANISM: Homo sapiens
<220> FEATURE:
<221> NAME/KEY: VARIANT
<222> LOCATION: (1)...(112)
<223> OTHER INFORMATION: truncated neublastin (NBN112)
```

<400> SEQUENCE: 8

```
Gly Gly Pro Gly Ser Arg Ala Arg Ala Ala Gly Ala Arg Gly Cys Arg
 1               5                  10                  15
Leu Arg Ser Gln Leu Val Pro Val Arg Ala Leu Gly Leu Gly His Arg
                20                  25                  30
Ser Asp Glu Leu Val Arg Phe Arg Phe Cys Ser Gly Ser Cys Arg Arg
             35                  40                  45
Ala Arg Ser Pro His Asp Leu Ser Leu Ala Ser Leu Leu Gly Ala Gly
 50                  55                  60
Ala Leu Arg Pro Pro Pro Gly Ser Arg Pro Val Ser Gln Pro Cys Cys
 65                  70                  75                  80
Arg Pro Thr Arg Tyr Glu Ala Val Ser Phe Met Asp Val Asn Ser Thr
                 85                  90                  95
Trp Arg Thr Val Asp Arg Leu Ser Ala Thr Ala Cys Gly Cys Leu Gly
                100                 105                 110
```

<210> SEQ ID NO 9
<211> LENGTH: 111
<212> TYPE: PRT
<213> ORGANISM: Homo sapiens
<220> FEATURE:
<221> NAME/KEY: VARIANT
<222> LOCATION: (1)...(111)
<223> OTHER INFORMATION: truncated neublastin (NBN111)

<400> SEQUENCE: 9

```
Gly Pro Gly Ser Arg Ala Arg Ala Ala Gly Ala Arg Gly Cys Arg Leu
 1               5                  10                  15
Arg Ser Gln Leu Val Pro Val Arg Ala Leu Gly Leu Gly His Arg Ser
                20                  25                  30
Asp Glu Leu Val Arg Phe Arg Phe Cys Ser Gly Ser Cys Arg Arg Ala
             35                  40                  45
Arg Ser Pro His Asp Leu Ser Leu Ala Ser Leu Leu Gly Ala Gly Ala
 50                  55                  60
Leu Arg Pro Pro Pro Gly Ser Arg Pro Val Ser Gln Pro Cys Cys Arg
 65                  70                  75                  80
Pro Thr Arg Tyr Glu Ala Val Ser Phe Met Asp Val Asn Ser Thr Trp
                 85                  90                  95
Arg Thr Val Asp Arg Leu Ser Ala Thr Ala Cys Gly Cys Leu Gly
                100                 105                 110
```

<210> SEQ ID NO 10
<211> LENGTH: 110
<212> TYPE: PRT
<213> ORGANISM: Homo sapiens
<220> FEATURE:
<221> NAME/KEY: VARIANT
<222> LOCATION: (1)...(110)
<223> OTHER INFORMATION: truncated neublastin (NBN110)

<400> SEQUENCE: 10

```
Pro Gly Ser Arg Ala Arg Ala Ala Gly Ala Arg Gly Cys Arg Leu Arg
 1               5                  10                  15
Ser Gln Leu Val Pro Val Arg Ala Leu Gly Leu Gly His Arg Ser Asp
                20                  25                  30
Glu Leu Val Arg Phe Arg Phe Cys Ser Gly Ser Cys Arg Arg Ala Arg
             35                  40                  45
Ser Pro His Asp Leu Ser Leu Ala Ser Leu Leu Gly Ala Gly Ala Leu
```

-continued

```
                    50                  55                  60
Arg Pro Pro Pro Gly Ser Arg Pro Val Ser Gln Pro Cys Cys Arg Pro
 65                  70                  75                  80

Thr Arg Tyr Glu Ala Val Ser Phe Met Asp Val Asn Ser Thr Trp Arg
                     85                  90                  95

Thr Val Asp Arg Leu Ser Ala Thr Ala Cys Gly Cys Leu Gly
                100                 105                 110

<210> SEQ ID NO 11
<211> LENGTH: 109
<212> TYPE: PRT
<213> ORGANISM: Homo sapiens
<220> FEATURE:
<221> NAME/KEY: VARIANT
<222> LOCATION: (1)...(109)
<223> OTHER INFORMATION: truncated neublastin (NBN109)

<400> SEQUENCE: 11

Gly Ser Arg Ala Arg Ala Ala Gly Ala Arg Gly Cys Arg Leu Arg Ser
 1               5                  10                  15

Gln Leu Val Pro Val Arg Ala Leu Gly Leu Gly His Arg Ser Asp Glu
                20                  25                  30

Leu Val Arg Phe Arg Phe Cys Ser Gly Ser Cys Arg Arg Ala Arg Ser
            35                  40                  45

Pro His Asp Leu Ser Leu Ala Ser Leu Leu Gly Ala Gly Ala Leu Arg
         50                  55                  60

Pro Pro Pro Gly Ser Arg Pro Val Ser Gln Pro Cys Cys Arg Pro Thr
 65                  70                  75                  80

Arg Tyr Glu Ala Val Ser Phe Met Asp Val Asn Ser Thr Trp Arg Thr
                     85                  90                  95

Val Asp Arg Leu Ser Ala Thr Ala Cys Gly Cys Leu Gly
                100                 105

<210> SEQ ID NO 12
<211> LENGTH: 108
<212> TYPE: PRT
<213> ORGANISM: Homo sapiens
<220> FEATURE:
<221> NAME/KEY: VARIANT
<222> LOCATION: (1)...(108)
<223> OTHER INFORMATION: truncated neublastin (NBN108)

<400> SEQUENCE: 12

Ser Arg Ala Arg Ala Ala Gly Ala Arg Gly Cys Arg Leu Arg Ser Gln
 1               5                  10                  15

Leu Val Pro Val Arg Ala Leu Gly Leu Gly His Arg Ser Asp Glu Leu
                20                  25                  30

Val Arg Phe Arg Phe Cys Ser Gly Ser Cys Arg Arg Ala Arg Ser Pro
            35                  40                  45

His Asp Leu Ser Leu Ala Ser Leu Leu Gly Ala Gly Ala Leu Arg Pro
         50                  55                  60

Pro Pro Gly Ser Arg Pro Val Ser Gln Pro Cys Cys Arg Pro Thr Arg
 65                  70                  75                  80

Tyr Glu Ala Val Ser Phe Met Asp Val Asn Ser Thr Trp Arg Thr Val
                     85                  90                  95

Asp Arg Leu Ser Ala Thr Ala Cys Gly Cys Leu Gly
                100                 105

<210> SEQ ID NO 13
```

```
<211> LENGTH: 107
<212> TYPE: PRT
<213> ORGANISM: Homo sapiens
<220> FEATURE:
<221> NAME/KEY: VARIANT
<222> LOCATION: (1)...(107)
<223> OTHER INFORMATION: truncated neublastin (NBN107)

<400> SEQUENCE: 13

Arg Ala Arg Ala Ala Gly Ala Arg Gly Cys Arg Leu Arg Ser Gln Leu
 1               5                  10                  15

Val Pro Val Arg Ala Leu Gly Leu Gly His Arg Ser Asp Glu Leu Val
            20                  25                  30

Arg Phe Arg Phe Cys Ser Gly Ser Cys Arg Arg Ala Arg Ser Pro His
        35                  40                  45

Asp Leu Ser Leu Ala Ser Leu Leu Gly Ala Gly Ala Leu Arg Pro Pro
    50                  55                  60

Pro Gly Ser Arg Pro Val Ser Gln Pro Cys Cys Arg Pro Thr Arg Tyr
65                  70                  75                  80

Glu Ala Val Ser Phe Met Asp Val Asn Ser Thr Trp Arg Thr Val Asp
                85                  90                  95

Arg Leu Ser Ala Thr Ala Cys Gly Cys Leu Gly
            100                 105

<210> SEQ ID NO 14
<211> LENGTH: 106
<212> TYPE: PRT
<213> ORGANISM: Homo sapiens
<220> FEATURE:
<221> NAME/KEY: VARIANT
<222> LOCATION: (1)...(106)
<223> OTHER INFORMATION: truncated neublastin (NBN106)

<400> SEQUENCE: 14

Ala Arg Ala Ala Gly Ala Arg Gly Cys Arg Leu Arg Ser Gln Leu Val
 1               5                  10                  15

Pro Val Arg Ala Leu Gly Leu Gly His Arg Ser Asp Glu Leu Val Arg
            20                  25                  30

Phe Arg Phe Cys Ser Gly Ser Cys Arg Arg Ala Arg Ser Pro His Asp
        35                  40                  45

Leu Ser Leu Ala Ser Leu Leu Gly Ala Gly Ala Leu Arg Pro Pro Pro
    50                  55                  60

Gly Ser Arg Pro Val Ser Gln Pro Cys Cys Arg Pro Thr Arg Tyr Glu
65                  70                  75                  80

Ala Val Ser Phe Met Asp Val Asn Ser Thr Trp Arg Thr Val Asp Arg
                85                  90                  95

Leu Ser Ala Thr Ala Cys Gly Cys Leu Gly
            100                 105

<210> SEQ ID NO 15
<211> LENGTH: 105
<212> TYPE: PRT
<213> ORGANISM: Homo sapiens
<220> FEATURE:
<221> NAME/KEY: VARIANT
<222> LOCATION: (1)...(105)
<223> OTHER INFORMATION: truncated neublastin (NBN105)

<400> SEQUENCE: 15

Arg Ala Ala Gly Ala Arg Gly Cys Arg Leu Arg Ser Gln Leu Val Pro
 1               5                  10                  15
```

```
Val Arg Ala Leu Gly Leu Gly His Arg Ser Asp Glu Leu Val Arg Phe
            20                  25                  30

Arg Phe Cys Ser Gly Ser Cys Arg Arg Ala Arg Ser Pro His Asp Leu
         35                  40                  45

Ser Leu Ala Ser Leu Leu Gly Ala Gly Ala Leu Arg Pro Pro Pro Gly
 50                  55                  60

Ser Arg Pro Val Ser Gln Pro Cys Cys Arg Pro Thr Arg Tyr Glu Ala
 65                  70                  75                  80

Val Ser Phe Met Asp Val Asn Ser Thr Trp Arg Thr Val Asp Arg Leu
                 85                  90                  95

Ser Ala Thr Ala Cys Gly Cys Leu Gly
                100                 105

<210> SEQ ID NO 16
<211> LENGTH: 104
<212> TYPE: PRT
<213> ORGANISM: Homo sapiens
<220> FEATURE:
<221> NAME/KEY: VARIANT
<222> LOCATION: (1)...(104)
<223> OTHER INFORMATION: truncated neublastin (NBN104)

<400> SEQUENCE: 16

Ala Ala Gly Ala Arg Gly Cys Arg Leu Arg Ser Gln Leu Val Pro Val
 1               5                  10                  15

Arg Ala Leu Gly Leu Gly His Arg Ser Asp Glu Leu Val Arg Phe Arg
                 20                  25                  30

Phe Cys Ser Gly Ser Cys Arg Arg Ala Arg Ser Pro His Asp Leu Ser
             35                  40                  45

Leu Ala Ser Leu Leu Gly Ala Gly Ala Leu Arg Pro Pro Pro Gly Ser
 50                  55                  60

Arg Pro Val Ser Gln Pro Cys Cys Arg Pro Thr Arg Tyr Glu Ala Val
 65                  70                  75                  80

Ser Phe Met Asp Val Asn Ser Thr Trp Arg Thr Val Asp Arg Leu Ser
                 85                  90                  95

Ala Thr Ala Cys Gly Cys Leu Gly
            100

<210> SEQ ID NO 17
<211> LENGTH: 103
<212> TYPE: PRT
<213> ORGANISM: Homo sapiens
<220> FEATURE:
<221> NAME/KEY: VARIANT
<222> LOCATION: (1)...(103)
<223> OTHER INFORMATION: truncated neublastin (NBN103)

<400> SEQUENCE: 17

Ala Gly Ala Arg Gly Cys Arg Leu Arg Ser Gln Leu Val Pro Val Arg
 1               5                  10                  15

Ala Leu Gly Leu Gly His Arg Ser Asp Glu Leu Val Arg Phe Arg Phe
                 20                  25                  30

Cys Ser Gly Ser Cys Arg Arg Ala Arg Ser Pro His Asp Leu Ser Leu
             35                  40                  45

Ala Ser Leu Leu Gly Ala Gly Ala Leu Arg Pro Pro Pro Gly Ser Arg
 50                  55                  60

Pro Val Ser Gln Pro Cys Cys Arg Pro Thr Arg Tyr Glu Ala Val Ser
 65                  70                  75                  80

Phe Met Asp Val Asn Ser Thr Trp Arg Thr Val Asp Arg Leu Ser Ala
```

```
                85                  90                  95

Thr Ala Cys Gly Cys Leu Gly
            100

<210> SEQ ID NO 18
<211> LENGTH: 102
<212> TYPE: PRT
<213> ORGANISM: Homo sapiens
<220> FEATURE:
<221> NAME/KEY: VARIANT
<222> LOCATION: (1)...(102)
<223> OTHER INFORMATION: truncated neublastin (NBN102)

<400> SEQUENCE: 18

Gly Ala Arg Gly Cys Arg Leu Arg Ser Gln Leu Val Pro Val Arg Ala
1               5                   10                  15

Leu Gly Leu Gly His Arg Ser Asp Glu Leu Val Arg Phe Arg Phe Cys
            20                  25                  30

Ser Gly Ser Cys Arg Arg Ala Arg Ser Pro His Asp Leu Ser Leu Ala
        35                  40                  45

Ser Leu Leu Gly Ala Gly Ala Leu Arg Pro Pro Pro Gly Ser Arg Pro
    50                  55                  60

Val Ser Gln Pro Cys Cys Arg Pro Thr Arg Tyr Glu Ala Val Ser Phe
65                  70                  75                  80

Met Asp Val Asn Ser Thr Trp Arg Thr Val Asp Arg Leu Ser Ala Thr
                85                  90                  95

Ala Cys Gly Cys Leu Gly
            100

<210> SEQ ID NO 19
<211> LENGTH: 101
<212> TYPE: PRT
<213> ORGANISM: Homo sapiens
<220> FEATURE:
<221> NAME/KEY: VARIANT
<222> LOCATION: (1)...(101)
<223> OTHER INFORMATION: truncated neublastin (NBN101)

<400> SEQUENCE: 19

Ala Arg Gly Cys Arg Leu Arg Ser Gln Leu Val Pro Val Arg Ala Leu
1               5                   10                  15

Gly Leu Gly His Arg Ser Asp Glu Leu Val Arg Phe Arg Phe Cys Ser
            20                  25                  30

Gly Ser Cys Arg Arg Ala Arg Ser Pro His Asp Leu Ser Leu Ala Ser
        35                  40                  45

Leu Leu Gly Ala Gly Ala Leu Arg Pro Pro Pro Gly Ser Arg Pro Val
    50                  55                  60

Ser Gln Pro Cys Cys Arg Pro Thr Arg Tyr Glu Ala Val Ser Phe Met
65                  70                  75                  80

Asp Val Asn Ser Thr Trp Arg Thr Val Asp Arg Leu Ser Ala Thr Ala
                85                  90                  95

Cys Gly Cys Leu Gly
            100

<210> SEQ ID NO 20
<211> LENGTH: 100
<212> TYPE: PRT
<213> ORGANISM: Homo sapiens
<220> FEATURE:
<221> NAME/KEY: VARIANT
<222> LOCATION: (1)...(100)
```

<223> OTHER INFORMATION: truncated neublastin (NBN100)

<400> SEQUENCE: 20

Arg Gly Cys Arg Leu Arg Ser Gln Leu Val Pro Val Arg Ala Leu Gly
1               5                   10                  15

Leu Gly His Arg Ser Asp Glu Leu Val Arg Phe Arg Phe Cys Ser Gly
            20                  25                  30

Ser Cys Arg Arg Ala Arg Ser Pro His Asp Leu Ser Leu Ala Ser Leu
        35                  40                  45

Leu Gly Ala Gly Ala Leu Arg Pro Pro Pro Gly Ser Arg Pro Val Ser
    50                  55                  60

Gln Pro Cys Cys Arg Pro Thr Arg Tyr Glu Ala Val Ser Phe Met Asp
65                  70                  75                  80

Val Asn Ser Thr Trp Arg Thr Val Asp Arg Leu Ser Ala Thr Ala Cys
                85                  90                  95

Gly Cys Leu Gly
            100

<210> SEQ ID NO 21
<211> LENGTH: 99
<212> TYPE: PRT
<213> ORGANISM: Homo sapiens
<220> FEATURE:
<221> NAME/KEY: VARIANT
<222> LOCATION: (1)...(99)
<223> OTHER INFORMATION: truncated neublastin (NBN99)

<400> SEQUENCE: 21

Gly Cys Arg Leu Arg Ser Gln Leu Val Pro Val Arg Ala Leu Gly Leu
1               5                   10                  15

Gly His Arg Ser Asp Glu Leu Val Arg Phe Arg Phe Cys Ser Gly Ser
            20                  25                  30

Cys Arg Arg Ala Arg Ser Pro His Asp Leu Ser Leu Ala Ser Leu Leu
        35                  40                  45

Gly Ala Gly Ala Leu Arg Pro Pro Pro Gly Ser Arg Pro Val Ser Gln
    50                  55                  60

Pro Cys Cys Arg Pro Thr Arg Tyr Glu Ala Val Ser Phe Met Asp Val
65                  70                  75                  80

Asn Ser Thr Trp Arg Thr Val Asp Arg Leu Ser Ala Thr Ala Cys Gly
                85                  90                  95

Cys Leu Gly

<210> SEQ ID NO 22
<211> LENGTH: 8
<212> TYPE: PRT
<213> ORGANISM: Artificial Sequence
<220> FEATURE:
<223> OTHER INFORMATION: purification tag peptide

<400> SEQUENCE: 22

Asp Tyr Lys Asp Asp Asp Asp Lys
1               5

<210> SEQ ID NO 23
<211> LENGTH: 113
<212> TYPE: PRT
<213> ORGANISM: Homo sapiens
<220> FEATURE:
<221> NAME/KEY: VARIANT
<222> LOCATION: (1)...(113)
<223> OTHER INFORMATION: mutated neublastin (NBN113-N95K)

<400> SEQUENCE: 23

Ala Gly Gly Pro Gly Ser Arg Ala Arg Ala Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

Arg Ala Arg Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Lys Ser
                85                  90                  95

Thr Trp Arg Thr Val Asp Arg Leu Ser Ala Thr Ala Cys Gly Cys Leu
            100                 105                 110

Gly

<210> SEQ ID NO 24
<211> LENGTH: 106
<212> TYPE: PRT
<213> ORGANISM: Homo sapiens
<220> FEATURE:
<221> NAME/KEY: VARIANT
<222> LOCATION: (1)...(106)
<223> OTHER INFORMATION: mutated neublastin (NBN106-N95K)

<400> SEQUENCE: 24

Ala Arg Ala Ala Gly Ala Arg Gly Cys Arg Leu Arg Ser Gln Leu Val
1               5                   10                  15

Pro Val Arg Ala Leu Gly Leu Gly His Arg Ser Asp Glu Leu Val Arg
            20                  25                  30

Phe Arg Phe Cys Ser Gly Ser Cys Arg Arg Ala Arg Ser Pro His Asp
        35                  40                  45

Leu Ser Leu Ala Ser Leu Leu Gly Ala Gly Ala Leu Arg Pro Pro Pro
    50                  55                  60

Gly Ser Arg Pro Val Ser Gln Pro Cys Cys Arg Pro Thr Arg Tyr Glu
65                  70                  75                  80

Ala Val Ser Phe Met Asp Val Lys Ser Thr Trp Arg Thr Val Asp Arg
                85                  90                  95

Leu Ser Ala Thr Ala Cys Gly Cys Leu Gly
            100                 105

<210> SEQ ID NO 25
<211> LENGTH: 675
<212> TYPE: DNA
<213> ORGANISM: Rattus norvegicus

<400> SEQUENCE: 25
atggaactgg gacttggaga gcctactgca ttgtcccact gcctccggcc taggtggcaa      60
ccagccttgt ggccaaccct agctgctcta gccctgctga gcagcgtcac agaagcttcc    120
ctggacccaa tgtcccgcag ccccgcctct cgcgatgttc cctcgccggt cctggcgccc    180
ccaacagact acctacctgg gggacacacc gcacatctgt gcagcgaaag agccctgcga    240
ccaccgccgc agtctcctca gcccgcaccc ccaccaccgg gtcccgcgct ccagtctcct    300
cccgctgcgc tccgcggggc acgcgcgcg cgtgcaggaa cccggagcag ccgcgcacgg    360

```
gctacagatg cgcgcggctg ccgcctgcgc tcacagctgg tgccggtgag cgctctcggc      420
ctgggccaca gctccgacga gctgatacgt ttccgcttct gcagcggttc gtgccgccga      480
gcacgctccc cgcacgatct cagcctggcc agcctgctgg gcgccggggc cctgcggtct      540
cctcccgggt cccggccgat cagccagccc tgttgccggc ccactcgcta tgaggcagtc      600
tccttcatgg acgtgaacag cacctggaga accgtggacc atctctccgc caccgcctgc      660
ggctgtctgg gctga                                                       675
```

<210> SEQ ID NO 26
<211> LENGTH: 224
<212> TYPE: PRT
<213> ORGANISM: Rattus norvegicus

<400> SEQUENCE: 26

```
Met Glu Leu Gly Leu Gly Glu Pro Thr Ala Leu Ser His Cys Leu Arg
1               5                   10                  15

Pro Arg Trp Gln Pro Ala Leu Trp Pro Thr Leu Ala Ala Leu Ala Leu
            20                  25                  30

Leu Ser Ser Val Thr Glu Ala Ser Leu Asp Pro Met Ser Arg Ser Pro
        35                  40                  45

Ala Ser Arg Asp Val Pro Ser Pro Val Leu Ala Pro Pro Thr Asp Tyr
    50                  55                  60

Leu Pro Gly Gly His Thr Ala His Leu Cys Ser Glu Arg Ala Leu Arg
65                  70                  75                  80

Pro Pro Pro Gln Ser Pro Gln Pro Ala Pro Pro Gly Pro Ala
                85                  90                  95

Leu Gln Ser Pro Pro Ala Ala Leu Arg Gly Ala Arg Ala Ala Arg Ala
            100                 105                 110

Gly Thr Arg Ser Ser Arg Ala Arg Ala Thr Asp Ala Arg Gly Cys Arg
        115                 120                 125

Leu Arg Ser Gln Leu Val Pro Val Ser Ala Leu Gly Leu Gly His Ser
    130                 135                 140

Ser Asp Glu Leu Ile Arg Phe Arg Phe Cys Ser Gly Ser Cys Arg Arg
145                 150                 155                 160

Ala Arg Ser Pro His Asp Leu Ser Leu Ala Ser Leu Leu Gly Ala Gly
                165                 170                 175

Ala Leu Arg Ser Pro Pro Gly Ser Arg Pro Ile Ser Gln Pro Cys Cys
            180                 185                 190

Arg Pro Thr Arg Tyr Glu Ala Val Ser Phe Met Asp Val Asn Ser Thr
        195                 200                 205

Trp Arg Thr Val Asp His Leu Ser Ala Thr Ala Cys Gly Cys Leu Gly
    210                 215                 220
```

<210> SEQ ID NO 27
<211> LENGTH: 37
<212> TYPE: DNA
<213> ORGANISM: Artificial Sequence
<220> FEATURE:
<223> OTHER INFORMATION: primer

<400> SEQUENCE: 27

```
gtatctttca tggacgttat gttctacatg gagaacc                                37
```

<210> SEQ ID NO 28
<211> LENGTH: 36
<212> TYPE: DNA
<213> ORGANISM: Artificial Sequence

```
<220> FEATURE:
<223> OTHER INFORMATION: primer

<400> SEQUENCE: 28
ggttctccat gtagaacata cgtccatgaa agatac                         36

<210> SEQ ID NO 29
<211> LENGTH: 35
<212> TYPE: DNA
<213> ORGANISM: Artificial Sequence
<220> FEATURE:
<223> OTHER INFORMATION: primer

<400> SEQUENCE: 29
gctcgtgcaa cggatgcaaa aggctgtcgt ctgcg                          35

<210> SEQ ID NO 30
<211> LENGTH: 35
<212> TYPE: DNA
<213> ORGANISM: Artificial Sequence
<220> FEATURE:
<223> OTHER INFORMATION: primer

<400> SEQUENCE: 30
cgcagacgac agccttttgc atccgttgca cgagc                          35

<210> SEQ ID NO 31
<211> LENGTH: 38
<212> TYPE: DNA
<213> ORGANISM: Artificial Sequence
<220> FEATURE:
<223> OTHER INFORMATION: primer

<400> SEQUENCE: 31
ggagccggag cactaaaatc tcccccggga tctagacc                       38

<210> SEQ ID NO 32
<211> LENGTH: 38
<212> TYPE: DNA
<213> ORGANISM: Artificial Sequence
<220> FEATURE:
<223> OTHER INFORMATION: primer

<400> SEQUENCE: 32
ggtctagatc ccgggggaga ttttagtgct ccggctcc                       38

<210> SEQ ID NO 33
<211> LENGTH: 32
<212> TYPE: DNA
<213> ORGANISM: Artificial Sequence
<220> FEATURE:
<223> OTHER INFORMATION: primer

<400> SEQUENCE: 33
gacgaattaa ttaagtttcg tttttgttca gg                             32

<210> SEQ ID NO 34
<211> LENGTH: 32
<212> TYPE: DNA
<213> ORGANISM: Artificial Sequence
<220> FEATURE:
<223> OTHER INFORMATION: primer

<400> SEQUENCE: 34
cctgaacaaa aacgaaactt aattaattcg tc                             32
```

<210> SEQ ID NO 35
<211> LENGTH: 414
<212> TYPE: DNA
<213> ORGANISM: Homo sapiens
<220> FEATURE:
<221> NAME/KEY: misc_feature
<222> LOCATION: (1)...(414)
<223> OTHER INFORMATION: His-tagged neublastin
<220> FEATURE:
<221> NAME/KEY: CDS
<222> LOCATION: (1)...(405)

<400> SEQUENCE: 35

```
atg ggc cat cat cat cat cat cat cat cat cac tcg agc ggc cat        48
Met Gly His His His His His His His His His Ser Ser Gly His
1               5                   10                  15 atc gac gac gac gac aag gct gga gga ccg gga tct cgt gct cgt gca    96
Ile Asp Asp Asp Asp Lys Ala Gly Gly Pro Gly Ser Arg Ala Arg Ala
                20                  25                  30 gca gga gca cgt ggc tgt cgt ctg cgt tct caa cta gtg ccg gtg cgt    144
Ala Gly Ala Arg Gly Cys Arg Leu Arg Ser Gln Leu Val Pro Val Arg
            35                  40                  45 gca ctc gga ctg gga cac cgt tcc gac gaa cta gta cgt ttt cgt ttt    192
Ala Leu Gly Leu Gly His Arg Ser Asp Glu Leu Val Arg Phe Arg Phe
        50                  55                  60 tgt tca gga tct tgt cgt cgt gca cgt tct ccg cat gat cta tct cta    240
Cys Ser Gly Ser Cys Arg Arg Ala Arg Ser Pro His Asp Leu Ser Leu
65                  70                  75                  80 gca tct cta cta gga gcc gga gca cta aga ccg ccg ccg gga tct aga    288
Ala Ser Leu Leu Gly Ala Gly Ala Leu Arg Pro Pro Pro Gly Ser Arg
                85                  90                  95 cct gta tct caa cct tgt tgt aga cct act aga tac gaa gca gta tct    336
Pro Val Ser Gln Pro Cys Cys Arg Pro Thr Arg Tyr Glu Ala Val Ser
                100                 105                 110 ttc atg gac gta aac tct aca tgg aga acc gta gat aga cta tct gca    384
Phe Met Asp Val Asn Ser Thr Trp Arg Thr Val Asp Arg Leu Ser Ala
            115                 120                 125 acc gca tgt ggc tgt cta gga tgataatag                              414
Thr Ala Cys Gly Cys Leu Gly
        130                 135
```

<210> SEQ ID NO 36
<211> LENGTH: 135
<212> TYPE: PRT
<213> ORGANISM: Homo sapiens
<220> FEATURE:
<221> NAME/KEY: VARIANT
<222> LOCATION: (1)...(135)
<223> OTHER INFORMATION: His-tagged neublastin

<400> SEQUENCE: 36

```
Met Gly His His His His His His His His His Ser Ser Gly His
1               5                   10                  15

Ile Asp Asp Asp Asp Lys Ala Gly Gly Pro Gly Ser Arg Ala Arg Ala
                20                  25                  30

Ala Gly Ala Arg Gly Cys Arg Leu Arg Ser Gln Leu Val Pro Val Arg
            35                  40                  45

Ala Leu Gly Leu Gly His Arg Ser Asp Glu Leu Val Arg Phe Arg Phe
        50                  55                  60

Cys Ser Gly Ser Cys Arg Arg Ala Arg Ser Pro His Asp Leu Ser Leu
65                  70                  75                  80

Ala Ser Leu Leu Gly Ala Gly Ala Leu Arg Pro Pro Pro Gly Ser Arg
```

```
                    85                  90                  95
Pro Val Ser Gln Pro Cys Cys Arg Pro Thr Arg Tyr Glu Ala Val Ser
                100                 105                 110
Phe Met Asp Val Asn Ser Thr Trp Arg Thr Val Asp Arg Leu Ser Ala
            115                 120                 125
Thr Ala Cys Gly Cys Leu Gly
        130                 135
```

POLYMER CONJUGATES OF MUTATED NEUBLASTIN

CROSS REFERENCE TO RELATED APPLICATIONS

This application claims priority from International application PCT/US02/02319, filed Jan. 25, 2002, which claims priority from U.S. provisional application Ser. No. 60/266,071, filed Feb. 1, 2001 (abandoned).

FIELD OF THE INVENTION

The invention relates to protein chemistry, molecular biology, neurobiology, neurology, and pain management.

BACKGROUND OF THE INVENTION

Neurotrophic factors are naturally-occurring proteins that regulate neuronal survival during development and regulate plasticity and structural integrity of the adult nervous system. Neurotrophic factors can be isolated from neural tissue and from non-neural tissue. During the last twenty years, many neurotrophic factors have been discovered. These neurotrophic factors can be classified into superfamilies, families, subfamilies and individual species based on their structure and function.

Neurotrophic factor superfamilies include the fibroblast growth factor (FGF) superfamily, the neurotrophin superfamily, and the transforming growth factor-β (TGF-β) superfamily. The glial cell line-derived neurotrophic factor (GDNF)-related ligands are a family of proteins within the TGF-β superfamily. GDNF-related ligands include GDNF, persephin (PSP), neurturin (NTN) and neublastin (NBN; known as artemin or enovin). Members of the GDNF-related ligand family are distinguished by, among other things, their seven conserved cysteine residues. These residues form intramolecular and intermolecular disulfide bridges and give rise to the tertiary and quaternary structure of the dimerized polypeptide ligand. Members of the family also share the ability to induce signaling through a multicomponent receptor complex consisting of a glycosylphosphatidylinositol (GPI)-anchored co-receptor of the GFRα family, a member of the GDNF-related ligand subfamily, and the RET tyrosine kinase receptor.

Activated RET initiates a signal transduction cascade that is responsible, at least in part, for the downstream effects of GDNF-related ligands. Accordingly, activation of RET may represent one desirable aspect of a therapy which acts through a GFRα receptor pathway to affect downstream cellular processes.

Neublastin is classified within the GDNF family because it shares regions of homology with other GDNF ligands including the seven cysteine motif (e.g., as described in EP02/02691, PCT publications US02/02319 and US02/06388), and because of its ability to bind to, and activate, the RET receptor as part of a GFRα complex. Specifically, neublastin is highly selective for binding to the GFRα3-RET receptor complex. In that respect, neublastin contains unique sub regions in its amino acid sequence as compared with other members of the GDNF-related ligand family.

Current data suggest that neublastin may have a protective and regenerative role in the peripheral and central nervous systems and, as a result, may be useful as a therapeutic agent for neurodegenerative disorders. For example, data suggest that neublastin may have survival promoting effects on cultured sensory neurons from dorsal root ganglia and from trigeminal ganglia, and on cultured substantia nigra dopaminergic neurons (Baloh et al., Neuron 21: 1291-1302 (1998)). It therefore appears that neublastin may promote survival of neuronal populations including sensory and dopaminergic neurons. This is important because the degeneration and dysfunction of neurons has been associated with disease states. For example, sensory and dopaminergic neuron pathologies underlie peripheral neuropathy and Parkinson's disease, respectively.

Therefore, administration of neublastin may be useful, for example, in the treatment of diseases associated with neuronal degeneration and dysfunction. However, neublastin is rapidly cleared by the body, which may affect the neublastin dosing paradigm required in therapeutic applications. Thus, a need exists for modified neublastin polypeptides with enhanced bioavailability. Accordingly, it is an object of the present invention to identify modified forms of neublastin which exhibit enhanced bioavailability.

SUMMARY OF THE INVENTION

The invention provides polymer-conjugated, mutated neublastin dimers. Each dimer contains a first polypeptide comprising a first amino-terminal amino acid and a second polypeptide comprising a second amino-terminal amino acid. Each polypeptide individually contains: (a) an amino acid sequence characterized by at least 70%, 80%, 90%, or 95% sequence identity with amino acids 8-113 of SEQ ID NO:1; (b) a cysteine residue at each of positions 16, 43, 47, 80, 81, 109, and 111 (numbering according to SEQ ID NO:1); (c) amino acid residues as follows: C at position 16, L at position 18, V at position 25, L at position 28, G at position 29, L at position 30, G at position 31, E at position 36, F at position 40, R at position 41, F at position 42, C at position 43, G at position 45, C at position 47, C at position 80, C at position 81, R at position 82, P at position 83, F at position 91, D at position 93, S at position 105, A at position 106, C at position 109 and C at position 111; and (d) an LGLG repeat (residues 28-31 of SEQ ID NO:1), an FRFC motif (residues 40-43 of SEQ ID NO:1), a QPCCRP motif (residues 78-83 of SEQ ID NO:1), and a SATACGC motif (residues 105-111 of SEQ ID NO:1). The dimer includes at least one amino acid substitution (with respect to SEQ ID NO:1), which provides an internal polymer conjugation site to which a polymer is conjugated.

The invention also provides a polymer-conjugated, mutated neublastin dimer containing a first polypeptide and a second polypeptide, wherein each polypeptide contains 90-140, e.g., 95-120 or 100-110, amino acids of SEQ ID NO:6 with 1-6 amino acid substitutions, each substitution providing a polymer conjugation site to which a polymer is conjugated. Specific examples of polypeptides of the invention include NBN113 (SEQ ID NO:2), NBN140 (SEQ ID NO:6), NBN116 (SEQ ID NO:7), NBN112 (SEQ ID NO:8), NBN111 (SEQ ID NO:9), NBN110 (SEQ ID NO:10), NBN109 (SEQ ID NO:11), NBN108 (SEQ ID NO:12), NBN107 (SEQ ID NO:13), NBN106 (SEQ ID NO:14), NBN105 (SEQ ID NO:15), NBN104 (SEQ ID NO:16), NBN103 (SEQ ID NO:17), NBN102 (SEQ ID NO:18), NBN101 (SEQ ID NO:19), NBN100 (SEQ ID NO:20) and NBN99 (SEQ ID NO:21).

Preferably, at least one of the two amino-terminal amino acids in the dimer is conjugated to a polymer. Preferred amino acid substitutions include replacement of an arginine residue with a lysine residue (Raa#K; where aa# is the amino acid number based on SEQ ID NO: 1), and replacement of an asparagine residue with a lysine residue (Naa#K) or an aspartate residue (Naa#D). Specific examples of such substitution are R14K, R39K, R68K, N95D, and N95K (numbering based on SEQ ID NO:1). A particularly preferred substitution is N95K.

Preferably, the total combined molecular weight of the polymers on a dimer is 20,000-40,000 Da. Preferably, the average molecular weight of each polymer is 2,000-100,000 Da; more preferably, 5,000-50,000 Da; and most preferably, about 10,000 to 20,000 Da. The polymer can be linear or branched. Preferably, the polymer is a polyalkylene glycol moiety, e.g., a polyethylene glycol (PEG) moiety. In some embodiments, at least one polypeptide is glycosylated.

In some embodiments of the invention, the polymer-conjugated dimer contains a first polypeptide and a second polypeptide, wherein: (a) each polypeptide individually comprises 100 to 110 amino acids of SEQ ID NO:1, (b) each polypeptide comprises an asparagine-to-lysine substitution at amino acid number 95 in SEQ ID NO: 1, (c) and the dimer comprises 3 or 4 PEG moieties, wherein the molecular weight of each PEG moiety is about 10,000 Da, and each PEG moiety is conjugated at an amino-terminus or at lysine 95. A preferred embodiment is a homodimer containing a pair of monomers designated 3(,4)×10 kDa PEG NBN106-N95K.

The invention includes a pharmaceutical composition comprising a dimer according to the invention. In some embodiments, the composition contains two or more different dimers according to the invention.

The invention includes a nucleic acid, e.g., a DNA expression vector that encodes a polypeptide for incorporation into a dimer of the invention. The invention also includes a host cell transformed with the nucleic acid.

The invention includes a method for treating neuropathic pain in a mammal. The method includes administering to the mammal a therapeutically effective amount of the dimer of the invention. In some embodiments, the therapeutically effective amount is from 0.1 µg/kg to 1000 µg/kg, from 1 µg/kg to 100 µg/kg, or from 1 µg/kg to 30 µg/kg. Administration of the dimer can be by various routes, e.g., intramuscular, subcutaneous or intravenous. In some methods according to the invention, the dimer is administered three times per week. The invention also provides a method of activating the RET receptor in a mammal. The method includes administering to the mammal an effective amount of the dimer.

Other features and advantages of the invention will be apparent from the following detailed description and claims.

DETAILED DESCRIPTION OF THE INVENTION

Unless otherwise stated, any reference to a neublastin amino acid position number will refer to the numbering illustrated in SEQ ID NO:1.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

As used herein, "wild-type neublastin polypeptide" means a naturally-occurring neublastin polypeptide sequence. A wild-type neublastin polypeptide may be further defined by the source of the neublastin, for example, human, mouse, or rat neublastin (see, e.g., SEQ ID NO: 2, 3, or 4). A consensus neublastin polypeptide sequence is provided as SEQ ID NO:1.

As used herein, "mutated neublastin polypeptide," means a polypeptide that contains at least a specified minimum level of sequence identity with respect to a wild-type neublastin polypeptide, contains at least one amino acid substitution, insertion or fusion, with respect to the wild-type neublastin polypeptide, and displays neublastin activity (e.g., as described in International application No. PCT/US02/02319 (WO 02/060929).)

As used herein, "internal polymer conjugation site" means a non-terminal amino acid residue in a mutated neublastin polypeptide, which residue provides a side chain suitable for conjugation of a polymer.

As used herein, "modified neublastin polypeptide," means a polypeptide that contains at least one attached polymer.

As used herein, "fusion" means a co-linear, covalent linkage of two or more polypeptides through their respective peptide backbones through genetic expression of a polynucleotide molecule encoding those proteins in the same reading frame.

As used herein, "identity" refers to the sequence similarity between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are homologous at that position. The "percentage identity" between two sequences is a function of the number of matching positions shared by the two sequences divided by the number of positions compared ×100. For instance, if 6 of 10 positions in two sequences are matched, then the two sequences have 60% identity. By way of example, the DNA sequences CTGACT and CAGGTT share 50% homology (3 of the 6 total positions are matched). Generally, a comparison is made when two sequences are aligned to give maximum homology. Such alignment can be provided using, for instance, the method of Needleman et al., J. Mol Biol. 48: 443-453 (1970), implemented conveniently by computer programs such as the Align program (DNAstar, Inc.). "Similar" sequences are those which, when aligned, share identical and similar amino acid residues, where similar residues are conservative substitutions for, or "allowed point mutations" of, corresponding amino acid residues in an aligned reference sequence. In this regard, a "conservative substitution" of a residue in a reference sequence is a substitution by a residue that is physically or functionally similar to the corresponding reference residue, e.g., that has a similar size, shape, electric charge, chemical properties, including the ability to form covalent or hydrogen bonds, or the like. Thus, a "conservative substitution mutated" sequence is one that differs from a reference sequence or a wild-type sequence in that one or more conservative substitutions or allowed point mutations are present. The "percentage positive" between two sequences is a function of the number of positions that contain matching residues or conservative substitutions shared by the two sequences divided by the number of positions compared ×100. For instance, if 6 of 10 positions in two sequences are matched and 2 of 10 positions contain conservative substitutions, then the two sequences have 80% positive homology.

Mutated Neublastin Polypeptides

The mutated neublastin polypeptides of the invention retain neurotrophic activity and have enhanced bioavailability as compared to the wild-type neublastin polypeptide. For example, the mutated neublastins of this invention activate the RET gene product in assays in which the wild-type neublastin activates RET. In general, the mutated neublastin polypeptide will retain at least one of the following features but will additionally comprise at least one modification, such that an internal polymer conjugation site is created:

i) seven conserved cysteine residues at positions 16, 43, 47, 80, 81, 109, and 111 when numbered in accordance with SEQ ID NO:1-4;

ii) amino acid residues as follows: C at position 16, L at position 18, V at position 25, L at position 28, G at position 29, L at position 30, G at position 31, E at position 36, F at position 40, R at position 41, F at position 42, C at position 43, G at position 45, C at position 47, C at position 80, C at position 81, R at position 82, P at position 83, F at position 91, D at position 93, S at position 105, A at position 106, C at position 109 and C at position 111, each when numbered in accordance with SEQ ID NO:1-4;

iii) an LGLG repeat (residues 28-31 of SEQ ID NO:1), an FRFC motif (residues 40-43 of SEQ ID NO:1), a QPC-CRP motif (residues 78-83 of SEQ ID NO:1), and a SATACGC motif (residues 105-111 of SEQ ID NO:1).

In some embodiments, the invention provides a truncated mutated neublastin polypeptide, wherein the amino terminus of the truncated neublastin polypeptide lacks one or more amino-terminal amino acids of a mature neublastin polypeptide but is mutated to possess an internal polymer attachment. Preferably, the truncated mutated neublastin polypeptide, when dimerized, activates a RET polypeptide. In some embodiments the mutated neublastin polypeptide induces dimerization of the RET polypeptide. Such induction may require additional polypeptides or co-factors, as would be apparent to one of skill in the art.

Amino acid sequences of human and mouse neublastin polypeptides are disclosed in PCT publication WO00/01815. Examples of wild-type neublastin polypeptides according to the invention are presented in Table 1A. A neublastin consensus sequence (consensus with respect to human, mouse and rat) is set forth in Table 1B.

TABLE 1A

Wild-type mature NBN113 polypeptides

```
  1 AGGPGSRARAAGARGCRLRSQLVPVRALGLGHRSDELVRF  human
    AGTRSSRARTTDARGCRLRSQLVPVSALGLGHSSDELIRF  mouse
    AGTRSSRARATDARGCRLRSQLVPVSALGLGHSSDELIRF  rat
    ||  ||||    |||||||||||||| ||||||  |||| ||
    ag---srar---argcrlrsqlvpv-alglgh-sdel-rf  consensus 41 RFCSGSCRRARSPHDLSLASLLGAGALRPPPGSRPVSQPC  human
    RFCSGSCRRARSQHDLSLASLLGAGALRSPPGSRPISQPC  mouse
    RFCSGSCRRARSPHDLSLASLLGAGALRSPPGSRPISQPC  rat
    |||||||||||| |||||||||||||| ||||||| ||||
    rfcagacrrars-hdlslasllgagalr-ppgsrp-sqpc  consensus 81 CRPTRYEAVSFMDVNSTWRTVDRLSATACGCLG         human  (SEQ ID NO:2)
    CRPTRYEAVSFMDVNSTWRTVDHLSATACGCLG         mouse  (SEQ ID NO:3)
    CRPTRYEAVSFMDVNSTWRTVDHLSATACGCLG         rat    (SEQ ID NO:4)
    |||||||||||||||||||||| |||||||||
    crptryeavsfmdvnstwrtvd-lsatacgclg         consensus (SEQ ID NO:1)
                  *                                 * = Asn95
```

In some embodiments, at least one of the arginine (Arg or R) or asparagine (Asn or N) residues shown in bold in Table 1A is substituted with a different amino acid residue. In a preferred embodiment, the mutated neublastin polypeptide has a lysine (Lys or K) residue substituted for the asparagine at amino acid position 95, indicated by an asterisk in Table 1A, and is referred to as NBN-N95K. In general, the N95K substitution results in improved solubility. This facilitates formulation at high concentrations.

TABLE 1B

NBN113 Consensus Sequence

Consensus sequence:

Ala Gly Xaa1 Xaa2 Xaa3 Ser Arg Ala Arg Xaa4 Xaa5 Xaa6 Ala Arg Gly Cys    (SEQ ID NO: 1)

Arg Leu Arg Ser Gln Leu Val Pro Val Xaa7 Ala Leu Gly Leu Gly His Xaa8 Ser

Asp Glu Leu Xaa9 Arg Phe Arg Phe Cys Ser Gly Ser Cys Arg Arg Ala Arg

Ser Xaa10 His Asp Leu Ser Leu Ala Ser Leu Leu Gly Ala Gly Ala Leu Arg

Xaa11 Pro Pro Gly Ser Arg Pro Xaa12 Ser Gln Pro Cys Cys Arg Pro Thr Arg

TABLE 1B-continued

NBN113 Consensus Sequence

Tyr Glu Ala Val Ser Phe Met Asp Val Asn Ser Thr Trp Arg Thr Val Asp

Xaa13 Leu Ser Ala Thr Ala Cys Gly Cys Leu Gly wherein:
Xaa$_1$ is Gly or Thr    Xaa$_6$ is Gly or Asp    Xaa$_{11}$ is Pro or Ser
Xaa$_2$ is Pro or Arg    Xaa$_7$ is Arg or Ser    Xaa$_{12}$ is Val or Ile
Xaa$_3$ is Gly or Ser    Xaa$_8$ is Arg or Ser    Xaa$_{13}$ is Arg or His
Xaa$_4$ is Ala or Thr    Xaa$_9$ is Val or Ile
Xaa$_5$ is Ala or Thr    Xaa$_{10}$ is Pro or Gln The invention includes a polymer-conjugated mutated neublastin polypeptide comprising an amino acid sequence that is, for example, at least 70% identical to amino acids 8-113 of SEQ ID NO:1 (also shown in Table 1). In one embodiment, one or more of the arginines at position 14, position 39, position 68, or the asparagine at position 95 is replaced by an amino acid other than arginine or asparagine. In one embodiment, the wild-type amino acid is substituted with lysine or cysteine.

The substituted residues in the mutated neublastin polypeptide can be chosen to facilitate coupling of a polymer, e.g., a polyalkylene glycol polymer, at the substituted amino acid. Advantageous sites of modification are those at solvent accessible regions in the neublastin polypeptide. Such sites can be chosen based on inspection of the crystal structure of the related neurotrophic factor, such as GDNF, whose crystal structure is described in Eigenbrot et al., Nat. Struct. Biol. 4:435-38, 1997. Sites also can be chosen based on the crystal structure of neublastin, whose crystallization and structure determination is described below. Also, sites can be chosen based on structural-functional information provided for persephin/neublastin chimeric proteins. These chimeras are described in Baloh et al., J. Biol. Chem. 275:3412-20, 2000. An exemplary listing of solvent accessible or surface exposed neublastin amino acids identified through this methodology is set forth in Table 2.

Table 2 provides a list of residues and numbers in human neublastin that are expected to be surface exposed. The first column refers to surface exposed residues determined by examining the structure of the rat GDNF dimer formed by chains A and B (PDB code 1AGQ) and determining whether a residue was on the surface of the structure. This structure was then compared to a sequence alignment of GDNF and neublastin in Baloh et al., Neuron 21:1291-1302, 1998 to determine the proper residues in neublastin. The second and third columns, respectively, refer to the surface exposed residues determined by examining the structure of the human neublastin dimer formed by chains A and B. The numbering scheme in Table 2 is that shown in Table 1.

TABLE 2

1 Ala nnn
 2 Gly nnn
 3 Gly nnn
 4 Pro nnn
 5 Gly nnn
 6 Ser nnn
 7 Arg nnn
 8 Ala nnn
 9 Arg nnn
10 Ala nnn
11 Ala nnn
12 Gly +nn TABLE 2-continued 13 Ala −nn
14 Arg ++n
15 Gly +−+
16 Cys −−−
17 Arg +++
18 Leu +++
19 Arg +−−
20 Ser +++
21 Gln +−+
22 Leu +++
23 Val −−−
24 Pro +−+
25 Val −−−
26 Arg +++
27 Ala +−−
28 Leu −−−
29 Gly +++
30 Leu +++
31 Gly +++
32 His +−+
33 Arg +++
34 Ser −−−
35 Asp +++
36 Glu +++
37 Leu +++
38 Val −−−
39 Arg +++
40 Phe −−−
41 Arg +++
42 Phe +−−
43 Cys −−−
44 Ser +−−
45 Gly +−−
46 Ser +−+
47 Cys −−−
48 Arg +++
49 Arg +++
50 Ala −++
51 Arg +−+
52 Ser +++
53 Pro +++
54 His −−−
55 Asp −−−
56 Leu +++
57 Ser −−−
58 Leu −−−
59 Ala +−−
60 Ser +−+
61 Leu −−−
62 Leu +++
63 Gly +++
64 Ala +++
65 Gly +++
66 Ala +++
67 Leu −−−
68 Arg n++
69 Pro n++
70 Pro n−−
71 Pro n++
72 Gly +++
73 Ser +++

TABLE 2-continued

| | | |
|---|---|---|
| 74 | Arg | n++ |
| 75 | Pro | n-- |
| 76 | Val | -++ |
| 77 | Ser | --- |
| 78 | Gln | +++ |
| 79 | Pro | --- |
| 80 | Cys | --- |
| 81 | Cys | --- |
| 82 | Arg | --- |
| 83 | Pro | --- |
| 84 | Thr | +++ |
| 85 | Arg | +++ |
| 86 | Tyr | +++ |
| 87 | Glu | +++ |
| 88 | Ala | +++ |
| 89 | Val | +-- |
| 90 | Ser | +++ |
| 91 | Phe | --- |
| 92 | Met | +++ |
| 93 | Asp | +-- |
| 94 | Val | +++ |
| 95 | Asn | +++ |
| 96 | Ser | +++ |
| 97 | Thr | +++ |
| 98 | Trp | +++ |
| 99 | Arg | +++ |
| 100 | Thr | +++ |
| 101 | Val | -++ |
| 102 | Asp | +++ |
| 103 | Arg | +++ |
| 104 | Leu | --- |
| 105 | Ser | --- |
| 106 | Ala | --- |
| 107 | Thr | +++ |
| 108 | Ala | +++ |
| 109 | Cys | --- |
| 110 | Gly | +-- |
| 111 | Cys | --- |
| 112 | Leu | +++ |
| 113 | Gly | n- | n indicates that the residues are not present in the structures of GDNF or neublastin. This is either because of construct design, flexible regions, or inserts in neublastin relative to GDNF (residues 68-71).

TABLE 2-continued

– indicates the residues are buried and not on the surface or are cysteine residues involved in disulfide bonds. As this protein is a cysteine knot, a great majority of the residues are on the surface.
+ indicates that this residue is surface exposed in the GDNF structure or in the neublastin structure, although the loop containing residues 66-75 is visible in only one of the GDNF monomers (presumably flexible). This loop also contains a 4 residue insert in neublastin relative to GDNF.

Insome embodiments, the neublastin polypeptide retains the seven conserved Cys residues that are characteristic of the GDNF subfamily and of the TGF-beta super family.

The sequence of the human full-length prepro NBN polypeptide (SEQ ID NO:5) is shown in Table 3. Three mature forms of neublastin polypeptides were identified. These forms include:

(i) the 140 AA polypeptide designated herein as NBN140, which possesses the amino acid sequence designated as SEQ ID NO:6;

(ii) the 116 AA polypeptide designated herein as NBN116, which possesses the amino acid sequence designated as SEQ ID NO:7; and (iii) the 113 AA polypeptide designated herein as NBN113, which possesses the amino acid sequence designated as SEQ ID NO:2.

Table 3 illustrates the relationship between the disclosed prepro neublastin polypeptide sequences of the invention. Line 1 provides the polypeptide of SEQ ID NO:5, line 2 provides the polypeptide of SEQ ID NO:6, line 3 provides the polypeptide of SEQ ID NO:7 and line 4 provides the polypeptide of SEQ ID NO:2. The seven conserved cysteine residues are designated by symbols ("*", "#", "+" and "|") to indicate the intramolecular (* with *, # with #, and + with +) and intermolecular ("|") disulfide bridges formed in the mature dimerized neublastin ligand. The caret mark ("|") indicates the asparagine residue at amino acid position 95 that is substituted with a lysine in NBN106-N95K.

Table 3. NBN polypeptide sequences

```
                   10        20        30        40        50
              ....|....|....|....|....|....|....|....|....|....|
PrePro        ---------------MELGLGGLSTLSHCPWPRRQPALWPTLAALALL      33
NBN140        --------------------------------------------------
NBN116        --------------------------------------------------
NBN113        --------------------------------------------------

60        70        80        90       100
              ....|....|....|....|....|....|....|....|....|....|
PrePro        SSVAEASLGSAPRSPAPREGPPPVLASPAGHLPGGRTARWCSGRARRPPP    83
NBN140        -----------------------------------------------PPP     3
NBN116        --------------------------------------------------
NBN113        --------------------------------------------------

110       120       130       140       150
              ....|....|....|....|....|....|....|....|....|....|
PrePro        QPSRPAPPPPAPPSALPRGGRAARAGGPGSRARAAGARGCRLRSQLVPVR   133
NBN140        QPSRPAPPPPAPPSALPRGGRAARAGGPGSRARAAGARGCRLRSQLVPVR    53
NBN116        --------------------AARAGGPGSRARAAGARGCRLRSQLVPVR    29
NBN113        ------------------------AGGPGSRARAAGARGCRLRSQLVPVR    26
                                                              *

160       170       180       190       200
              ....|....|....|....|....|....|....|....|....|....|
PrePro        ALGLGHRSDELVRFRFCSGSCRRARSPHDLSLASLLGAGALRPPPGSRPV   183
NBN140        ALGLGHRSDELVRFRFCSGSCRRARSPHDLSLASLLGAGALRPPPGSRPV   103
NBN116        ALGLGHRSDELVRFRFCSGSCRRARSPHDLSLASLLGAGALRPPPGSRPV    79
NBN113        ALGLGHRSDELVRFRFCSGSCRRARSPHDLSLASLLGAGALRPPPGSRPV    76
                             #  +

210       220       230
              ....|....|....|....|....|....|..
PrePro        SQPCCRPTRYEAVSFMDVNSTWRTVDRLSATACGCLG   220    (SEQ ID NO:5)
NBN140        SQPCCRPTRYEAVSFMDVNSTWRTVDRLSATACGCLG   140    (SEQ ID NO:6)
NBN116        SQPCCRPTRYEAVSFMDVNSTWRTVDRLSATACGCLG   116    (SEQ ID NO:7)
NBN113        SQPCCRPTRYEAVSFMDVNSTWRTVDRLSATACGCLG   113    (SEQ ID NO:2)
               | *           ^           #  +
```

In alternative embodiments, the sequence of the above identified neublastin polypeptides have been truncated at their amino-terminal amino acid sequence. Examples of these include:
- (iv) the 112AA polypeptide sequence designated herein as NBN112, which possesses the 112 carboxy terminal amino acids of a neublastin polypeptide, e.g., amino acids 29-140 of SEQ ID NO:6 (SEQ ID NO:8) or amino acids 2-113 of SEQ ID NOs:1, 3, or 4.
- (v) the 111 AA polypeptide sequence designated herein as NBN111, which possesses the 111 carboxy terminal amino acids of a neublastin polypeptide, e.g., amino acids 30-140 of SEQ ID NO:6 (SEQ ID NO:9) or amino acids 3-113 of SEQ ID NOs:1, 3 or 4.
- (vi) the 110AA polypeptide sequence designated herein as NBN110, which possesses the 110 carboxy terminal amino acids of a neublastin polypeptide, e.g., amino acids 31-140 of SEQ ID NO:6 (SEQ ID NO:10) or amino acids 4-113 of SEQ ID NOs:1, 3 or 4.
- (vii) the 109AA polypeptide sequence designated herein as NBN109, which possesses the 109 carboxy terminal amino acids of a neublastin polypeptide, e.g., amino acids 32-140 of SEQ ID NO:6 (SEQ ID NO: 11) or amino acids 5-113 of SEQ ID NOs:1, 3 or 4.
- (viii) the 108AA polypeptide sequence designated herein as NBN108, which possesses the 108 carboxy terminal amino acids of a neublastin polypeptide, e.g., amino acids 33-140 of SEQ ID NO:6 (SEQ ID NO:12) or amino acids 6-113 of SEQ ID NOs:1, 3 or 4.
- (ix) the 107AA polypeptide sequence designated herein as NBN107, which possesses the 107 carboxy terminal amino acids of a neublastin polypeptide, e.g., amino acids 34-140 of SEQ ID NO:6 (SEQ ID NO:13) or amino acids 7-113 of SEQ ID NOs:1, 3 or 4.
- (x) the 106AA polypeptide sequence designated herein alternatively as NBN106 or N-7, which possesses the 106 carboxy terminal amino acids of a neublastin polypeptide, e.g., amino acids 35-140 of SEQ ID NO:6 (SEQ ID NO:14) or amino acids 8-113 of SEQ ID NOs: 1, 3 or 4.
- (xi) the 105AA polypeptide sequence designated herein as NBN105, which possesses the 105 carboxy terminal amino acids of a neublastin polypeptide, e.g., amino acids 36-140 of SEQ ID NO:6 (SEQ ID NO:15) or amino acids 9-113 of SEQ ID NOs:1, 3 or 4.
- (xii) the 104AA polypeptide sequence designated herein alternatively as NBN104 or N-9, which possesses the 104 carboxy terminal amino acids of a neublastin polypeptide, e.g., amino acids 37-140 of SEQ ID NO:6 (SEQ ID NO:16) or amino acids 10-113 of SEQ ID NOs:1, 3 or 4.
- (xiii) the 103AA polypeptide sequence designated herein as NBN103, which possesses the 103 carboxy terminal amino acids of a neublastin polypeptide, e.g., amino acids 38-140 of SEQ ID NO:6 (SEQ ID NO:17) or amino acids 11-113 of SEQ ID NOs:1, 3 or 4.
- (xiv) the 102AA polypeptide sequence designated herein as NBN102, which possesses the 102 carboxy terminal amino acids of a neublastin polypeptide, e.g., amino acids 39-140 of SEQ ID NO:6 (SEQ ID NO:18) or amino acids 12-113 of SEQ ID NOs:1, 3 or 4.
- (xv) the 101AA polypeptide sequence designated herein as NBN101, which possesses the 101 carboxy terminal amino acids of a neublastin polypeptide, e.g., amino acids 40-140 of SEQ ID NO:6 (SEQ ID NO:19) or amino acids 13-113 of SEQ ID NOs:1, 3 or4.
- (xvi) the 100AA polypeptide sequence designated herein as NBN100, which possesses the 100 carboxy terminal amino acids of a neublastin polypeptide, e.g., amino acids 41-140 of SEQ ID NO:6 (SEQ ID NO:20) or amino acids 14-113 of SEQ ID NOs:1, 3 or 4.
- (xvii) the 99AA polypeptide sequence designated herein alternatively as NBN99 or N-14, which possesses the 99 carboxy terminal amino acids of a neublastin polypeptide, e.g., amino acids 42-140 of SEQ ID NO:6 (SEQ ID NO:21) or amino acids 15-113 of SEQ ID NOs:1, 3 or 4.

The polypeptide sequences of these truncated neublastin polypeptides are shown in Table 4 for NBN113 through NBN99. Disulfide bridge formation is as described for Table 3.

Table 4. Alignment of Truncated Neublastin Polypeptides

```
                 10        20        30        40        50
        ....|....|....|....|....|....|....|....|....|....|
NBN113  AGGPGSRARAAGARGCRLRSQLVPVRALGLGHRSDELVRFRFCSGSCRRA  50
NBN112  -GGPGSRARAAGARGCRLRSQLVPVRALGLGHRSDELVRFRFCSGSCRRA  49
NBN111  --GPGSRARAAGARGCRLRSQLVPVRALGLGHRSDELVRFRFCSGSCRRA  48
NBN110  ---PGSRARAAGARGCRLRSQLVPVRALGLGHRSDELVRFRFCSGSCRRA  47
NBN109  ----GSRARAAGARGCRLRSQLVPVRALGLGHRSDELVRFRFCSGSCRRA  46
NBN108  -----SRARAAGARGCRLRSQLVPVRALGLGHRSDELVRFRFCSGSCRRA  45
NBN107  ------RARAAGARGCRLRSQLVPVRALGLGHRSDELVRFRFCSGSCRRA  44
NBN106  -------ARAAGARGCRLRSQLVPVRALGLGHRSDELVRFRFCSGSCRRA  43
NBN105  --------RAAGARGCRLRSQLVPVRALGLGHRSDELVRFRFCSGSCRRA  42
NBN104  ---------AAGARGCRLRSQLVPVRALGLGHRSDELVRFRFCSGSCRRA  41
NBN103  ----------AGARGCRLRSQLVPVRALGLGHRSDELVRFRFCSGSCRRA  40
NBN102  -----------GARGCRLRSQLVPVRALGLGHRSDELVRFRFCSGSCRRA  39
NBN101  ------------ARGCRLRSQLVPVRALGLGHRSDELVRFRFCSGSCRRA  38
NBN100  -------------RGCRLRSQLVPVRALGLGHRSDELVRFRFCSGSCRRA  37
NBN99   --------------GCRLRSQLVPVRALGLGHRSDELVRFRFCSGSCRRA  36
                       *                          #    +

60        70        80        90       100
        ....|....|....|....|....|....|....|....|....|....|
NBN113  RSPHDLSLASLLGAGALRPPPGSRPVSQPCCRPTRYEAVSFMDVNSTWRT  100
NBN112  RSPHDLSLASLLGAGALRPPPGSRPVSQPCCRPTRYEAVSFMDVNSTWRT   99
NBN111  RSPHDLSLASLLGAGALRPPPGSRPVSQPCCRPTRYEAVSFMDVNSTWRT   98
NBN110  RSPHDLSLASLLGAGALRPPPGSRPVSQPCCRPTRYEAVSFMDVNSTWRT   97
NBN109  RSPHDLSLASLLGAGALRPPPGSRPVSQPCCRPTRYEAVSFMDVNSTWRT   96
NBN108  RSPHDLSLASLLGAGALRPPPGSRPVSQPCCRPTRYEAVSFMDVNSTWRT   95
NBN107  RSPHDLSLASLLGAGALRPPPGSRPVSQPCCRPTRYEAVSFMDVNSTWRT   94
NBN106  RSPHDLSLASLLGAGALRPPPGSRPVSQPCCRPTRYEAVSFMDVNSTWRT   93
NBN105  RSPHDLSLASLLGAGALRPPPGSRPVSQPCCRPTRYEAVSFMDVNSTWRT   92
NBN104  RSPHDLSLASLLGAGALRPPPGSRPVSQPCCRPTRYEAVSFMDVNSTWRT   91
NBN103  RSPHDLSLASLLGAGALRPPPGSRPVSQPCCRPTRYEAVSFMDVNSTWRT   90
NBN102  RSPHDLSLASLLGAGALRPPPGSRPVSQPCCRPTRYEAVSFMDVNSTWRT   89
NBN101  RSPHDLSLASLLGAGALRPPPGSRPVSQPCCRPTRYEAVSFMDVNSTWRT   88
NBN100  RSPHDLSLASLLGAGALRPPPGSRPVSQPCCRPTRYEAVSFMDVNSTWRT   87
NBN99   RSPHDLSLASLLGAGALRPPPGSRPVSQPCCRPTRYEAVSFMDVNSTWRT   86
                         |*                       ^

110
        ....|....|...
NBN113  VDRLSATACGCLG  113  (SEQ ID NO:2)
NBN112  VDRLSATACGCLG  112  (SEQ ID NO:8)
NBN111  VDRLSATACGCLG  111  (SEQ ID NO:9)
NBN110  VDRLSATACGCLG  110  (SEQ ID NO:10)
NBN109  VDRLSATACGCLG  109  (SEQ ID NO:11)
NBN108  VDRLSATACGCLG  108  (SEQ ID NO:12)
NBN107  VDRLSATACGCLG  107  (SEQ ID NO:13)
NBN106  VDRLSATACGCLG  106  (SEQ ID NO:14)
NBN105  VDRLSATACGCLG  105  (SEQ ID NO:15)
NBN104  VDRLSATACGCLG  104  (SEQ ID NO:16)
NBN103  VDRLSATACGCLG  103  (SEQ ID NO:17)
NBN102  VDRLSATACGCLG  102  (SEQ ID NO:18)
NBN101  VDRLSATACGCLG  101  (SEQ ID NO:19)
NBN100  VDRLSATACGCLG  100  (SEQ ID NO:20)
NBN99   VDRLSATACGCLG   99  (SEQ ID NO:21)
          # +
```

A mutated neublastin polypeptide according to the invention can be, e.g., at least 80%, 85%, 90%, 95%, 98% or 99% identical to amino acids 8-113 of SEQ ID NO:1. In some embodiments, the amino acid sequence of the mutated neublastin polypeptide includes the amino acid sequence of a naturally occurring rat, human or mouse neublastin polypeptide at amino acids 1-94 and 96-113 of the mutated neublastin polypeptide, e.g., the polypeptide has the amino acid sequence of SEQ ID NOs: 2, 3, or 4 at these positions.

A mutated neublastin polypeptide differing in sequence from those disclosed in SEQ ID NOs:1-4 may include one or more conservative amino acid substitutions. Alternatively, or in addition, the mutated neublastin polypeptide may differ by one or more non conservative amino acid substitutions, or by deletions or insertions. Preferably, the substitutions, insertions or deletions do not abolish the isolated protein's biological activity.

A conservative substitution is the substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution.

Other substitutions can be readily identified by those of ordinary skill in the art. For example, for the amino acid alanine, a substitution can be taken from any one of D-alanine, glycine, beta-alanine, cysteine and D-cysteine. For lysine, a replacement can be any one of D-lysine, arginine, D-arginine, homo-arginine, methionine, D-methionine, ornithine, or D-ornithine. Generally, substitutions in functionally important regions that may be expected to induce changes in the properties of isolated polypeptides are those in which: (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions may alter functional properties of the protein is also correlated to the position of the substitution with respect to functionally important regions of the protein. Some non-conservative substitutions may accordingly have little or no effect on biological properties.

In many cases, a polymer-conjugated mutated neublastin polypeptide has a longer serum half-life relative to the half-life of the wild-type polypeptide or mutated polypeptide in the absence of the polymer. In some embodiments, the polymer conjugated mutated neublastin polypeptide has significantly increased potency in vivo relative to the potency of the polypeptide or glycosylated-polypeptide in the absence of the polymer.

The polymer-conjugated neublastin polypeptide can be provided as a dimer that includes at least one polymer-conjugated neublastin polypeptide. In some embodiments, the dimer is a homodimer of polymer-conjugated mutated neublastin polypeptides. In other embodiments, the dimer is a homodimer of polymer-conjugated mutated truncated neublastin polypeptides. In other embodiments, the dimer is a heterodimer that includes one polymer-conjugated mutated neublastin polypeptide and one wild-type neublastin polypeptide. In other embodiments, the dimer is a heterodimer that includes one polymer-conjugated mutated neublastin polypeptide, and one polymer-conjugated wild-type neublastin polypeptide where the polymer conjugation is at the amino-terminus, and where the polypeptides may or may not be truncated. Other dimers include heterodimers or homodimers of polymer-conjugated mutated neublastin polypeptide forms that may or may not be truncated.

Provided in the invention are mature and truncated mutated polypeptide sequences comprising the carboxy-terminal-most amino acid residues of the preproNBN polypeptide, such as provided in SEQ ID NO:5, and which are designated herein as NBN#, where # represents the number of carboxy-terminal residues remaining in the referenced neublastin polypeptide. Polymer-conjugated neublastin polypeptides present in the bioactive neublastin dimers may be products of a protease cleavage reaction or a chemical cleavage reaction, or may be expressed from recombinant DNA construct, or may be synthesized. Example neublastin polypeptides include, e.g., NBN140, NBN116, and NBN113. Additional neublastin polypeptides of the invention include NBN112, NBN111, NBN110, NBN109, NBN108, NBN107, NBN106, NBN105, NBN104, NBN103, NBN102, NBN101, NBN100 and NBN99 (SEQ ID NOS:8-21).

A preferred polymer-conjugated neublastin polypeptide is a homodimer of NBN106-N95K conjugated either to three 10 kDa PEG moieties ("3×10 kDa PEG NBN106-N95K") or to four 10 kDa PEG moieties ("4×10 kDa PEG NBN106-N95K"). Also preferred is a mixed population of NBN106-N95K homodimers conjugated either to three 10 kDa PEG moieties or to four 10 kDa PEG moieties, referred to herein as "3(,4)×10 kDa PEG NBN106-N95K". Also preferred is a 3(,4)×10 kDa PEG NBN106-N95K homodimer, wherein the two amino-terminal amino acids are covalently linked to PEG moieties and the third and/or fourth PEG moiety is covalently linked to one or both substituted N95K residue(s).

In some embodiments, the polymer-conjugated neublastin polypeptide is based on the consensus sequence of SEQ ID NO:1. In certain embodiments, a polymer-conjugated neublastin polypeptide includes amino acids 1-7 of SEQ ID NO:1 in addition to amino acids 8-113.

In some embodiments, the polymer-conjugated neublastin polypeptide, when dimerized, binds GFRα3. In some embodiments, the polymer-conjugated neublastin polypeptide, when dimerized, stimulates tyrosine phosphorylation of a RET polypeptide, either on its own or when bound to GFRα3.

In some embodiments, the polymer-conjugated neublastin polypeptide, when dimerized, enhances neuron survival, e.g., enhances survival of a sensory neuron.

In some embodiments, the polymer-conjugated neublastin polypeptide, when dimerized, reduces or reverses pathological changes of a neuron, such as a sensory neuron.

In some embodiments, the polymer-conjugated neublastin polypeptide, when dimerized, enhances survival of a neuron, e.g., an autonomic neuron, or a dopaminergic neuron.

In some embodiments, the polymer-conjugated neublastin polypeptide includes one, two, three, four or more of the amino acid substitutions selected from the group consisting of an amino acid other than arginine at position 14 in the amino acid sequence of the polymer-conjugated polypeptide, an amino acid other than arginine at position 39 in the amino acid sequence of the polymer-conjugated polypeptide, an amino acid other than arginine at position 68 of the polymer-conjugated polypeptide, and an amino acid other than asparagine at position 95 of the polymer-conjugated polypeptide. In some embodiments, the amino acid at one or more of the amino acid at positions 14, 39, 68, and 95 is lysine. Preferably, amino acids 8-94 and 96-113 of the polymer-conjugated neublastin polypeptide are at least 90% identical to amino acids 8-94 and 96-113 of SEQ ID NO:1. More preferably, the amino acids sequences are at least 95% identical thereto. Most preferably, the amino acid sequence of the polymer-conjugated neublastin polypeptide includes the amino acid sequence of a naturally occurring human, mouse or rat neublastin polypeptide at amino acids 8-94 and 96-113 of the polymer-conjugated neublastin polypeptide. For example, amino acids 8-94 and 96-113 of the polymer-conjugated neublastin polypeptide can include the amino acid sequence of amino acids 8-94 and 96-113 of SEQ ID NO:1, SEQ ID NO:2, SEQ ID NO:3 or SEQ ID NO: 4. In the above embodiments, the preferred residue at amino acid position 95 is a lysine or a cysteine.

The invention includes a construct that is a heterodimer or a homodimer containing polymer-conjugated neublastin fusion proteins, e.g., the polyhistidine (His)-tagged neublastin provided in SEQ ID NO:36, or a neublastin fusion protein where the fusion moiety is an immunoglobulin (Ig) polypeptide, serum albumin polypeptide or a replicase-derived polypeptide. Neublastin fusion proteins can have enhanced pharmacokinetic and bioavailability properties in vivo.

The invention provides a nucleic acid molecule encoding a mature or truncated neublastin polypeptide, with a mutated polypeptide sequence. The nucleic acid molecule encoding a provided neublastin polypeptide is preferably provided in a vector, e.g., an expression vector. A mutated neublastin nucleic acid molecule, or a vector including the same, can be provided in a cell. The cell can be, e.g., a mammalian cell, fungal cell, yeast cell, insect cell, or bacterial cell. A preferred mammalian cell is a Chinese hamster ovary cell ("CHO cell").

Also provided by the invention is a method of making a polymer-conjugated neublastin polypeptide, by culturing a cell containing a nucleic acid encoding a neublastin polypeptide under conditions allowing for expression of a neublastin polypeptide. In some embodiments, the neublastin is conjugated to a naturally occurring moiety. In specific embodiments, the naturally occurring moiety is a glycosyl moiety. In certain embodiments, the glycosylated neublastin is expressed, e.g., in a CHO cell. The invention further includes a neublastin polypeptide expressed in a cell. Similar nucleic acids, vectors, host cells, and polypeptide production methods are disclosed herein for the fusion proteins (such as the neublastin-serum albumin fusion proteins) of this invention.

In some embodiments, a neublastin polypeptide that is expressed in a cell is recovered and conjugated to a polymer. In some embodiments, the polymer is a polyalkylene glycol moiety. In particular embodiments, the polymer is a PEG moiety.

Specifically provided by the invention is a composition that includes a mutated neublastin polypeptide coupled to a non-naturally occurring polymer. The mutated neublastin polypeptide in the composition preferably includes an amino acid sequence at least 70% identical to amino acids 8-113 of SEQ ID NO:1, provided that the polymer-conjugated neublastin polypeptide includes one or more of the amino acid substitutions selected from the group consisting of an amino acid other than arginine at position 14 in the amino acid sequence of the polymer-conjugated polypeptide, an amino acid other than arginine at position 39 in the amino acid sequence of the polymer-conjugated polypeptide, an amino acid other than arginine at position 68 of the polymer-conjugated polypeptide, and an amino acid other than asparagine at position 95 of the polymer-conjugated polypeptide, wherein the positions of the amino acids are numbered in accordance with the polypeptide sequence of SEQ ID NO:1.

The invention includes a stable, aqueous soluble conjugated neublastin polypeptide or mutated neublastin polypeptide complex comprising a neublastin polypeptide or mutated neublastin polypeptide coupled to a PEG moiety, wherein the neublastin polypeptide or mutated neublastin polypeptide is coupled to the PEG moiety by a labile bond. In some embodiments, the labile bond is cleavable by biochemical hydrolysis, proteolysis, or sulfhydryl cleavage. In some embodiments, the labile bond is cleavable under in vivo conditions.

Also provided by the invention is a method for making a modified neublastin polypeptide that has prolonged serum half-life relative to a wild-type neublastin. The method included providing a neublastin polypeptide or mutated neublastin polypeptide, and coupling the polypeptide or mutatedneublastin polypeptide to a non-naturally occurring polymer moiety, thereby forming a coupled polymer neublastin polypeptide composition.

The polymer-conjugated mutated neublastin polypeptides of this invention include one or more amino acid substitutions in which, for example, an amino acid other than arginine occurs at position 14 in the amino acid sequence of the polymer-conjugated polypeptide, an amino acid other than arginine at position 39 occurs in the amino acid sequence of the polymer-conjugated polypeptide, an amino acid other than arginine at position 68 occurs in the polymer-conjugated polypeptide, or an amino acid other than asparagine at position 95 occurs in the polymer-conjugated polypeptide, when the positions of the amino acids are numbered in accordance with the polypeptide sequence of SEQ ID NO:1.

Synthesis and Isolation of Wild-Type and Mutated Neublastin Polypeptides

Neublastin polypeptides can be isolated using methods known in the art. Naturally occurring neublastin polypeptides can be isolated from cells or tissue sources by an appropriate purification scheme using standard protein purification techniques. Alternatively, mutated neublastin polypeptides can be synthesized chemically using standard peptide synthesis techniques. The synthesis of short amino acid sequences is well established in the peptide art. See, e.g., Stewart, et al., Solid Phase Peptide Synthesis (2d ed., 1984).

In some embodiments, mutated neublastin polypeptides are produced by recombinant DNA techniques. For example, a nucleic acid molecule encoding a mutated neublastin polypeptide can be inserted into a vector, e.g., an expression vector, and the nucleic acid can be introduced into a cell. Suitable cells include, e.g., mammalian cells (such as human cells or CHO cells), fungal cells, yeast cells, insect cells, and bacterial cells. When expressed in a recombinant cell, the cell is preferably cultured under conditions allowing for expression of a mutated neublastin polypeptide. The mutated neublastin polypeptide can be recovered from a cell suspension if desired. As used herein, "recovered" means that the mutated polypeptide is removed from those components of a cell or culture medium in which it is present prior to the recovery process. The recovery process may include one or more refolding or purification steps.

Mutated neublastin polypeptides can be constructed using any of several methods known in the art. One such method is site-directed mutagenesis, in which a specific nucleotide (or, if desired a small number of specific nucleotides) is changed in order to change a single amino acid (or, if desired, a small number of predetermined amino acid residues) in the encoded neublastin polypeptide. Those skilled in the art recognize that site-directed mutagenesis is a routine and widely used technique. In fact, many site-directed mutagenesis kits are commercially available. One such kit is the "Transformer Site Directed Mutagenesis Kit" sold by Clontech Laboratories (Palo Alto, Calif.).

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition. (Sambrook, Fritsch and Maniatis, eds.), Cold Spring Harbor Laboratory Press, 1989; DNA Cloning, Volumes I and II (D. N. Glover, ed), 1985; Oligonucleotide Synthesis, (M. J. Gait, ed.), 1984; U.S. Pat. No. 4,683,195 (Mullis et al.,); Nucleic Acid Hybridization (B. D. Haines and S. J. Higgins, eds.), 1984; Transcription and Translation (B. D. Hames and S. J. Higgins, eds.), 1984; Culture of Animal Cells (R. I. Freshney, ed). Alan R. Liss, Inc., 1987; Immobilized Cells and Enzymes, IRL Press, 1986; A Practical Guide to Molecular Cloning (13.Perbal), 1984; Methods in Enzymology, Volumes 154 and 155 (Wu et al., eds), Academic Press, New York; Gene Transfer Vectors for Mammalian Cells (J. H. Miller and M. P. Calos, eds.), 1987, Cold Spring Harbor Laboratory; Immunochernical Methods in Cell and Molecular Biology (Mayer and Walker, eds.), Academic Press, London, 1987; Handbook of Experiment Immunology, Volumes I-IV (D. M. Weir and C. C. Blackwell, eds.), 1986; Manipulating the Mouse Embryo, Cold Spring Harbor Laboratory Press, 1986.

Polymer Conjugation of Neublastin Polypeptides

Chemically modified neublastin polypeptides may be prepared by one of skill in the art based upon the present disclosure. The chemical moieties preferred for conjugation to a neublastin polypeptide are water-soluble polymers. A water-soluble polymer is advantageous because the protein to which it is attached does not precipitate in an aqueous environment, such as a physiological environment. Preferably, the polymer will be pharmaceutically acceptable for the preparation of a therapeutic product or composition.

If desired, a single polymer molecule may be employed for conjugation with a neublastin polypeptide, although more than one polymer molecule can be attached as well. Conjugated neublastin compositions of the invention may find utility in both in vivo as well as non-in vivo applications. Additionally, it will be recognized that the conjugating polymer may utilize any other groups, moieties, or other conjugated species, as appropriate to the end use application. By way of example, it may be useful in some applications to covalently bond to the polymer a functional moiety imparting UV-degradation resistance, or antioxidation, or other properties or characteristics to the polymer. As a further example, it may be advantageous in some applications to functionalize the polymer to render it reactive or cross-linkable in character, to enhance various properties or characteristics of the overall conjugated material. Accordingly, the polymer may contain any functionality, repeating groups, linkages, or other constituent structures that do not preclude the efficacy of the conjugated neublastin composition for its intended purpose.

One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization may be ascertained by administering the derivative, in the desired form (e.g., by osmotic pump, or, more preferably, by injection or infusion, or, further formulated for oral, pulmonary or other delivery routes), and determining its effectiveness.

Suitable water-soluble polymers include, but are not limited to, PEG, copolymers of ethylene glycol/propylene glycol, carboxymethylcellulose, dextran, polyvinyl alcohol, polyvinyl pyrrolidone, poly-1, 3-dioxolane, poly-1, 3, 6-trioxane, ethylene/maleic anhydride copolymer, polyaminoacids (either homopolymers or random copolymers), and dextran or poly(n-vinyl pyrrolidone) PEG, propropylene glycol homopolymers, polypropylene oxide/ethylene oxide co-polymers, polyoxyethylated polyols (e.g., glycerol), polyvinyl alcohol, and mixtures thereof.

The polymer may be of any suitable molecular weight, and may be branched or unbranched.

For PEG, suitable average molecular weight is between about 2 kDa and about 100 kDa. This provides for ease in handling and manufacturing. Those of skill in the art will appreciate that in preparations of PEG, some molecules will weigh more, some less, than the stated molecular weight. Thus, molecular weight is typically specified as "average molecular weight." Other molecular weights (sizes) may be used, depending on the desired therapeutic profile (e.g., the duration of sustained release desired; the effects, if any, on biological activity; the ease in handling; the degree or lack of antigenicity and other known effects of PEG on a therapeutic protein). In various embodiments, the molecular weight is about 2 kDa, about 5 kDa, about 10 kDa, about 15 kDa, about 20 kDa, about 25 kDa, about 30 kDa, about 40 kDa or about 100 kDa. In certain preferred embodiments, the average molecular weight of each PEG chain is about 20 kDa. In certain preferred embodiments, the average molecular weight is about 10 kDa.

The number of polymer molecules so attached may vary, and one skilled in the art will be able to ascertain the effect on function. One may mono-derivatize, or may provide for a di-, tri-, tetra- or some combination of derivatization, with the same or different chemical moieties (e.g., polymers, such as different weights of PEGs). The proportion of polymer molecules to protein (or polypeptide) molecules will vary, as will their concentrations in the reaction mixture. In general, the optimum ratio (in terms of efficiency of reaction in that there is no excess unreacted protein or polymer) will be determined by factors such as the desired degree of derivatization (e.g., mono, di-, tri-, etc.), the molecular weight of the polymer selected, whether the polymer is branched or unbranched, and the reaction conditions.

The PEG molecules (or other chemical moieties) should be attached to the protein with consideration of effects on functional or antigenic domains of the protein. There are a number of attachment methods available to those skilled in the art. See, e.g., EP 0 401384 (coupling PEG to G-CSF); Malik et al., Exp. Hematol. 20: 1028-1035, 1992 (reporting PEGylation of GM-CSF using tresyl chloride).

For example, PEG may be covalently bound (PEGylation) through amino acid residues via a reactive group, such as, a free amino or carboxyl group. The amino acid residues having a free amino group include lysine residues and the amino-terminal amino acid residue. Those having a free carboxyl group include aspartic acid residues, glutamic acid residues, and the C-terminal amino acid residue. Sulfhydryl groups may also be used as a reactive group for attaching the PEG molecule(s). For therapeutic purposes, attachment can be at an amino group, e.g. at the N-terminus or lysine group. One may specifically desire an amino-terminal chemically modified protein.

Using PEG as an illustration of the present compositions, one may select from a variety of PEG molecules (by molecular weight, branching, etc.), the proportion of PEG molecules to protein (or peptide) molecules in the reaction mix, the type of PEGylation reaction to be performed, and the method of obtaining the selected amino-terminally PEGylated protein. The method of obtaining the amino-terminal PEGylated preparation (i.e., separating this moiety from other monoPEGylated moieties if necessary) may be by purification of the amino-terminal PEGylated material from a population of PEGylated protein molecules. Selective amino-terminal chemical modification may be accomplished by reductive alkylation that exploits differential reactivity of different types of primary amino groups (lysine versus the amino-terminal) available for derivatization in a particular protein. Under the appropriate reaction conditions, substantially selective derivatization of the protein at the amino-terminus with a carbonyl group containing polymer is achieved. For example, one may selectively PEGylate the amino-terminus of the protein by performing the reaction at a pH which allows one to take advantage of the pKa differences between the epsilon (ε)-amino group of the lysine residues and that of the alpha (α)-amino group of the amino-terminal residue of the protein. By such selective derivatization, attachment of a water soluble polymer to a protein is controlled: the conjugation with the polymer takes place predominantly at the amino-terminus of the protein and no significant modification of other reactive groups, such as the lysine side chain amino groups, occurs.

Using reductive alkylation, the water-soluble polymer may be of the type described above, and should have a single reactive aldehyde for coupling to the protein. PEG propional-dehyde, containing a single reactive aldehyde, may be used.

The present invention includes mutated neublastin polypeptides that are expressed in prokaryotes or eukaryotes or made synthetically. In some embodiments, the neublastin is glycosylated. In some specific embodiments, the neublastin dimer is polymer-conjugated at each amino-terminus and glycosylated at each internal Asn95 residue. In other embodiments, the mutated neublastin dimer is polymer-conjugated at each amino-terminus and polymer-conjugated at one or both internal Lys95 residues.

PEGylation may be carried out by any suitable PEGylation reaction. Various PEGylation chemistries are known in the art. See, e.g., Focus on Growth Factors, 3 (2): 4-10, 1992; EP 0 154 316; EP 0 401 384; and the other publications cited herein that relate to PEGylation. The PEGylation may be carried out via an acylation reaction or an alkylation reaction with a reactive PEG molecule (or an analogous reactive water-soluble polymer).

PEGylation by acylation generally involves reacting an active ester derivative of PEG. Any known or subsequently discovered reactive PEG molecule may be used to carry out the PEGylation. A preferred activated PEG ester is PEG esterified to N-hydroxysuccinimide (NHS). As used herein, "acylation" includes without limitation the following types of linkages between the therapeutic protein and a water soluble polymer such as PEG: amide, carbamate, urethane, and the like. See, *Bioconjugate Chem*. 5: 133-140, 1994. Reaction conditions may be selected from any of those known in the PEGylation art or those subsequently developed, but should avoid conditions such as temperature, solvent, and pH that would inactivate the neublastin protein or polypeptide to be modified.

PEGylation by acylation will generally result in a poly-PEGylated neublastin protein product. Preferably, the connecting linkage will be an amide. Also preferably, the resulting product will be substantially only (e.g., >95%) mono, di- or tri-PEGylated. However, some species with higher degrees of PEGylation may be formed in amounts depending on the specific reaction conditions used. If desired, more purified PEGylated species may be separated from the mixture, particularly unreacted species, by standard purification techniques, including, among others, dialysis, salting-out, ultrafiltration, ion-exchange chromatography, gel filtration chromatography and electrophoresis.

PEGylation by alkylation generally involves reacting a terminal aldehyde derivative of PEG with neublastin in the presence of a reducing agent. PEGylation by alkylation can also result in poly-PEGylated neublastin protein products. In addition, one can manipulate the reaction conditions to favor PEGylation substantially only at the α-amino group of the amino-terminus of neublastin (i.e., a mono-PEGylated protein). In either case of mono-PEGylation or poly-PEGylation, the PEG groups are preferably attached to the protein via a $—CH_2—NH—$ group. With particular reference to the $—CH_2—$ group, this type of linkage is referred to herein as an "alkyl" linkage.

Derivatization via reductive alkylation to produce a mono-PEGylated product exploits differential reactivity of different types of primary amino groups (lysine versus the amino-terminal) available for derivatization. The reaction is performed at a pH that allows one to take advantage of the pKa differences between the ϵ-amino groups of the lysine residues and that of the α-amino group of the amino-terminal residue of the protein. By such selective derivatization, attachment of a water soluble polymer that contains a reactive group such as an aldehyde, to a protein is controlled: the conjugation with the polymer takes place predominantly at the amino-terminus of the protein and no significant modification of other reactive groups, such as the lysine side chain amino groups, occurs.

The polymer molecules used in both the acylation and alkylation approaches may be selected from among water-soluble polymers as described above. The polymer selected should be modified to have a single reactive group, such as an active ester for acylation or an aldehyde for alkylation, preferably, so that the degree of polymerization may be controlled as provided for in the present methods. An exemplary reactive PEG aldehyde is PEG propionaldehyde, which is water stable, or mono C1-C10 alkoxy or aryloxy derivatives thereof (see, U.S. Pat. No. 5,252,714). The polymer may be branched or unbranched. For the acylation reactions, the polymer(s) selected should have a single reactive ester group. For the present reductive alkylation, the polymer(s) selected should have a single reactive aldehyde group. Generally, the water-soluble polymer will not be selected from naturally-occurring glycosyl residues since these are usually made more conveniently by mammalian recombinant expression systems. The polymer may be of any molecular weight, and may be branched or unbranched.

An exemplary water-soluble polymer for use herein is PEG. As used herein, polyethylene glycol encompasses any of the forms of PEG that have been used to derivatize other proteins, including but not limited to, e.g., mono-(C1-C10) alkoxy- or aryloxy-PEG.

In general, chemical derivatization may be performed under any suitable condition used to react a biologically active substance with an activated polymer molecule. Methods for preparing a PEGylated neublastin will generally comprise the steps of (a) reacting a neublastin protein or polypeptide with PEG (such as a reactive ester or aldehyde derivative of PEG) under conditions whereby the molecule becomes attached to one or more PEG groups, and (b) obtaining the reaction product(s). In general, the optimal reaction conditions for the acylation reactions will be determined case by case based on known parameters and the desired result. For example, the larger the ratio of PEG:protein, the greater the percentage of poly-PEGylated product.

Reductive alkylation to produce a substantially homogeneous population of mono-polymer/neublastin will generally comprise the steps of: (a) reacting a neublastin protein or polypeptide with a reactive PEG molecule under reductive alkylation conditions, at a pH suitable to pen-nit selective modification of the α-amino group at the amino terminus of neublastin; and (b) obtaining the reaction product(s).

For a substantially homogeneous population of mono-polymer/neublastin, the reductive alkylation reaction conditions are those that permit the selective attachment of the water-soluble polymer moiety to the amino-terminus of neublastin. Such reaction conditions generally provide for pKa differences between the lysine amino groups and the α-amino group at the amino-terminus (the pKa being the pH at which 50% of the amino groups are protonated and 50% are not). The pH also affects the ratio of polymer to protein to be used. In general, if the pH is lower, a larger excess of polymer to protein will be desired (i.e., the less reactive the amino-terminal α-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3-9, preferably 3-6.

Another important consideration is the molecular weight of the polymer. In general, the higher the molecular weight of the polymer, the fewer polymer molecules may be attached to the protein. Similarly, branching of the polymer should be taken into account when optimizing these parameters. Generally, the higher the molecular weight (or the more branches) the higher the polymer:protein ratio. In general, for the PEGylation reactions included herein, the preferred average molecular weight is about 2 kDa to about 100 kDa. The preferred average molecular weight is about 5 kDa to about 50 kDa, particularly preferably about 10 kDa to about 20 kDa. The preferred total molecular weight is about 10 kDa to about 40 kDa.

In some embodiments, the neublastin polypeptide is linked to the polymer via a terminal reactive group on the polypeptide. Alternatively, or in addition, the neublastin polypeptide may be linked via the side chain amino group of an internal lysine residue, e.g., a lysine residue introduced into the amino acid sequence of a naturally occurring neublastin polypeptide. Thus, conjugations can also be branched from the non terminal reactive groups. The polymer with the reactive group(s) is designated herein as "activated polymer". The reactive group selectively reacts with reactive groups on the protein, e.g., free amino.

Attachment may occur in the activated polymer at any available neublastin amino group such as the alpha amino groups or the epsilon amino groups of a lysine residue or residues introduced into the amino acid sequence of a neublastin polypeptide. Free carboxylic groups, suitably activated carbonyl groups, hydroxyl, guanidyl, imidazole, oxidized carbohydrate moieties and mercapto groups of the neublastin (if available) can also be used as attachment sites.

Generally from about 1.0 to about 10 moles of activated polymer per mole of protein, depending on protein concentration, is employed. The final amount is a balance between maximizing the extent of the reaction while minimizing non-specific modifications of the product and, at the same time, defining chemistries that will maintain optimum activity, while at the same time optimizing, if possible, the half-life of the protein. Preferably, at least about 50% of the biological activity of the protein is retained, and most preferably near 100% is retained.

The polymer can be coupled to the neublastin polypeptide using methods known in the art. For example, in one embodiment, the polyalkylene glycol moiety is coupled to a lysine group of the mutated neublastin polypeptide. Linkage to the lysine group can be performed with an N-hydroxylsuccinimide (NHS) active ester such as PEG succinimidyl succinate (SS-PEG) and succinimidyl propionate (SPA-PEG). Suitable polyalkylene glycol moieties include, e.g., carboxymethyl-NHS, norleucine-NHS, SC-PEG, tresylate, aldehyde, epoxide, carbonylimidazole, and PNP carbonate.

Additional amine reactive PEG linkers can be substituted for the succinimidyl moiety. These include, e.g. isothiocyanates, nitrophenylcarbonates, epoxides, and benzotriazole carbonates. Conditions are preferably chosen to maximize the selectivity and extent or reaction.

If desired, polymer-conjugated neublastin polypeptides may contain a tag, e.g., a tag that can subsequently be released by proteolysis. Thus, the lysine moiety can be selectively modified by first reacting a His-tag modified with a low molecular weight linker such as Traut's reagent (Pierce) which will react with both the lysine and amino-terminus, and then releasing the his tag. The polypeptide will then contain a free SH group that can be selectively modified with a PEG containing a thiol reactive head group such as a maleimide group, a vinylsulfone group, a haloacetate group, or a free or protected SH.

Traut's reagent can be replaced with any linker that will set up a specific site for PEG attachment. By way of example, Traut's reagent could be replaced with SPDP, SMPT, SATA, or SATP (all available from Pierce). Similarly one could react the protein with an amine reactive linker that inserts a maleimide (for example SMCC, AMAS, BMPS, MBS, EMCS, SMPB, SMPH, KMUS, or GMBS), a haloacetate group (SBAP, SIA, SIAB), or a vinylsulfone group and react the resulting product with a PEG that contains a free SH. The only limitation to the size of the linker that is employed is that it cannot block the subsequent removal of the amino-terminal tag.

Thus, in other embodiments, the polyalkylene glycol moiety is coupled to a cysteine group of the mutated neublastin polypeptide. Coupling can be effected using, e.g., a maleimide group, a vinylsulfone group, a haloacetate group, and a thiol group.

In preferred embodiments, the polymer-conjugated neublastin polypeptide in the composition has a longer serum half-life relative to the half-life of the neublastin polypeptide in the absence of the polymer. Alternatively, or in addition, the polymer-conjugated neublastin polypeptide dimer in the composition binds GFRα, activates RET, normalizes pathological changes of a neuron, enhances survival of a neuron, or ameliorates neuropathic pain, or performs a combination of these physiological functions. Assays for determining whether a polypeptide enhances survival of a neuron, or normalizes pathological changes of a neuron, are described in, e.g., WO00/01815. Preferably, the neuron is a sensory neuron, an autonomic neuron, or a dopaminergic neuron.

In preferred embodiments, the composition is provided as a stable, aqueous soluble conjugated neublastin polypeptide complex comprising a neublastin polypeptide or mutated neublastin polypeptide coupled to a PEG moiety. If desired, the neublastin polypeptide or mutated neublastin polypeptide may be coupled to the PEG moiety by a labile bond. The labile bond can be cleaved in, e.g., biochemical hydrolysis, proteolysis, or sulfhydryl cleavage. For example, the bond can be cleaved under in vivo (physiological) conditions.

Other reaction parameters, such as solvent, reaction times, temperatures, etc., and means of purification of products, can be determined case by case based on the published information relating to derivatization of proteins with water soluble polymers.

If desired, a single polymer molecule for conjugation per neublastin polypeptides may be employed. Alternatively, more than one polymer molecule may be attached. Conjugated neublastin compositions of the invention may find utility in both in vivo as well as non-in vivo applications. Additionally, it will be recognized that the conjugating polymer may utilize any other groups, moieties, or other conjugated species, as appropriate to the end use application. By way of example, it may be useful in some applications to covalently bond to the polymer a functional moiety imparting UV-degradation resistance, or antioxidation, or other properties or characteristics to the polymer. As a further example, it may be advantageous in some applications to functionalize the polymer to render it reactive or cross-linkable in character, to enhance various properties or characteristics of the overall conjugated material. Accordingly, the polymer may contain any functionality, repeating groups, linkages, or other constituent structures that do not preclude the efficacy of the conjugated neublastin mutein composition for its intended purpose.

Illustrative polymers that may usefully be employed to achieve these desirable characteristics are described herein below in exemplary reaction schemes. In covalently bonded peptide applications, the polymer may be functionalized and then coupled to free amino acid(s) of the peptide(s) to form labile bonds.

The reactions may take place by any suitable method used for reacting biologically active materials with inert polymers, preferably at about pH 5-8, e.g., pH 5, 6, 7, or 8, if the reactive groups are on the alpha amino group at the amino-terminus. Generally the process involves preparing an activated polymer and thereafter reacting the protein with the activated polymer to produce the soluble protein suitable for formulation. The above modification reaction can be performed by several methods, which may involve one or more steps.

Linear and branched forms of PEG can be used as well as other alkyl forms. The length of the PEG can be varied. Most common forms vary in size from 2K-100 kDa. While the present examples report that targeted PEGylation at the amino-terminus does not affect pharmokinetic properties, the fact that the material retained physiological function indicates that modification at the site or sites disclosed herein is not deleterious. Consequently, in generating mutant forms of neublastin that could provide additional sites of attachment through insertion of lysine residues, the likely outcome that these forms would be PEGylated both at the lysine and at the amino-terminus is encompassed by the invention.

One or more sites on a neublastin polypeptide can be coupled to a polymer. For example, one two, three, four, or five PEG moieties can be attached to the polypeptide. In some embodiments, a PEG moiety is attached at the amino terminus and/or amino acids 14, 39, 68, and 95 of a neublastin polypeptide numbered as shown in Table 1 and SEQ ID NO:1.

In advantageous embodiments, the polymer-conjugated neublastin polypeptide in the composition has a longer serum half-life relative to the half-life of the neublastin wild-type or mutated polypeptide in the absence of the polymer. Alternatively, or in addition, the polymer-conjugated neublastin polypeptide in the composition binds GFRα3, activates RET, normalizes pathological changes of a neuron, enhances survival of a neuron, or ameliorates neuropathic pain, or performs a combination of these physiological functions.

In some embodiments, the mutated neublastin polypeptide or polymer conjugate in the complex has a physiological activity selected from the group consisting of: GFRα3 binding, RET activation, normalization of pathological changes of a neuron, enhancing neuron survival, or ameliorating neuropathic pain.

Also provided by the invention are multimeric polypeptides that include a polymer-conjugated neublastin polypeptide. The multimeric polypeptides are preferably provided as purified multimeric polypeptides. Examples of multimeric complexes include, e.g., dimeric complexes. The multimeric complex can be provided as a heteromeric or homomeric complex. Thus, the multimeric complex can be a heterodimeric polymer-conjugated polypeptide complex including one mutated neublastin polypeptide and one non-mutated neublastin or a heterodimeric polymer-conjugated polypeptide complex including two or more mutated neublastin polypeptides.

In some embodiments, the polymer-conjugated neublastin polypeptide binds GFRα3. Preferably, binding of the polymer-conjugated neublastin polypeptide stimulates phosphorylation of a RET polypeptide. To determine whether a polypeptide binds GFRα3, assays can be performed as described in WO00/01815. For example, the presence of neublastin in the media of CHO cell line supernatants can be described using a modified form of a ternary complex assay described by Sanicola et al. (Proc. Natl. Acad. Sci. USA, 1997, 94: 6238). In this assay, the ability of GDNF-like molecules can be evaluated for their ability to mediate binding between the extracellular domain of RET and the various co-receptors, GFRα1, GFRα2, and GFRα3. Soluble forms of RET and the co-receptors are generated as fusion proteins. A fusion protein between the extracellular domain of rat RET and placental alkaline phosphatase (RET-AP) and a fusion protein between the extracellular domain of rat GFRα-1 (disclosed in published application WO9744356; Nov. 27, 1997) and the Fc domain of human IgG1 (rGFR(α1-Ig) have been described (Sanicola et al., Proc. Natl. Acad. Sci. USA 1997, 94: 6238).

The polymer of the invention is preferably a polyalkylene glycol moiety, and more preferably a PEG moiety. In some embodiments, a polymeric moiety has an average molecular weight of about 100 Da to about 25,000 Da; of about 1000 Da to about 20,000 Da; or of about 5000 Da to about 20,000 Da. In some embodiments, at least one polymeric moiety has an average molecular weight of about 5000 Da; an average molecular weight of about 10,000 Da; or an average molecular weight of about 20,000 Da.

The functional group on the polyalkylene glycol moiety can be, e.g., carboxymethyl-NHS, norleucine-NHS, SC-PEG, tresylate, aldehyde, epoxide, carbonylimidazole, or PNP carbonate. Coupling can occur via an N-hydroxylsuccinimide (NHS) active ester. The active ester can be, e.g., PEG succinimidyl succinate (SS-PEG), succinimidyl butyrate (SPB-PEG), or succinimidyl propionate (SPA-PEG). In some embodiments, the polyalkylene glycol moiety is coupled to a cysteine group of the neublastin polypeptide or mutated neublastin polypeptide. For example, coupling can occur via a maleimide group, a vinylsulfone group, a haloacetate group, and a thiol group. In various embodiments, the neublastin polypeptide or mutated neublastin polypeptide comprises one, two, three, or four PEG moieties.

In some embodiments, the polymer is coupled to the polypeptide at a site on the neublastin that is an N terminus. In some embodiments, the polymer is coupled to the polypeptide at a site in a non-terminal amino acid of the neublastin polypeptide or mutated neublastin polypeptide. In some embodiments, the polymer is coupled to a solvent exposed amino acid of the neublastin polypeptide or mutated neublastin polypeptide.

In some embodiments, the polymer is coupled to the neublastin polypeptide or mutated neublastin polypeptide at a residue selected from the group consisting of the amino terminal amino acid of the polymer-conjugated polypeptide, position 14 in the amino acid sequence of the neublastin polypeptide or mutated neublastin polypeptide, position 39 in the amino acid sequence of the neublastin polypeptide or mutated neublastin polypeptide, position 68 in the amino acid sequence of the neublastin polypeptide or mutated neublastin polypeptide, and position 95 in the amino acid sequence of the neublastin polypeptide or mutated polypeptide.

Polymer-Conjugated Neublastin Fusion Proteins

If desired, the polymer-conjugated neublastin polypeptide can be provided as a fusion protein. Fusion polypeptide derivatives of proteins of the invention also include various structural forms of the primary protein that retain biological activity.

Polymer-conjugated neublastin-serum albumin fusions can be constructed using methods known in the art. Any of a number of cross-linkers that contain a corresponding amino reactive group and thiol reactive group can be used to link neublastin to serum albumin. Examples of suitable linkers include amine reactive cross-linkers that insert a thiol reactive-maleimide. These include, e.g., SMCC, AMAS, BMPS, MBS, EMCS, SMPB, SMPH, KMUS, or GMBS. Other suitable linkers insert a thiol reactive-haloacetate group. These include, e.g., SBAP, SIA, SIAB and that provide a protected or non protected thiol for reaction with sulfhydryl groups to product a reducible linkage are SPDP, SMPT, SATA, or SATP all of which are commercially available (e.g., Pierce Chemicals). One skilled in the art can similarly envision with alternative strategies that will link the amino-terminus of neublastin with serum albumin.

It is also envisioned that one skilled in the art can generate conjugates to serum albumin that are not targeted at the amino-terminus of neublastin or at the thiol moiety on serum albumin. If desired, neublastin-serum albumin fusions can be generated using genetic engineering techniques, wherein neublastin is fused to the serum albumin gene at its amino-terminus carboxy-terminus, or at both ends.

Any neublastin conjugate that results in a product with a prolonged half-life, for example, in vivo or, specifically, in animals (including humans) can be generated using a similar strategy. Another example of a neublastin conjugate that results in a product with a prolonged half-life in vivo is a neublastin fusion protein where the fusion partner is an Ig.

Other derivatives of polymer-conjugated neublastins include covalent or aggregate conjugates of mutated neublastin or its fragments with other proteins or polypeptides, such as by synthesis in recombinant culture as additional amino-termini, or carboxy-termini. For example, the conjugated peptide may be a signal (or leader) polypeptide sequence at the amino-terminal region of the protein which co-translationally or post-translationally directs transfer of the protein from its site of synthesis to its site of function inside or outside of the cell membrane or wall (e.g., the yeast alpha-factor leader). Neublastin receptor proteins can comprise peptides added to facilitate purification or identification of neublastin (e.g., histidine/neublastin fusions). The amino acid sequence of neublastin can also be linked to the peptide Asp-Tyr-Lys-Asp-Asp-Asp-Asp-Lys (DYKDDDDK) (SEQ ID NO:22) (Hopp et al., Biotechnology 6:1204 (1988)). The latter sequence is highly antigenic and provides an epitope reversibly bound by a specific monoclonal antibody, enabling rapid assay and facile purification of expressed recombinant protein.

This sequence is also specifically cleaved by bovine mucosal enterokinase at the residue immediately following the Asp-Lys pairing.

Bioactive Polypeptides

The polypeptides of the invention may be provided in any bioactive form, including the form of pre-pro-proteins, pro-proteins, mature proteins, glycosylated proteins, non-glycosylated proteins, phosphorylated proteins, non-phosphorylated proteins, truncated forms, or any other posttranslational modified protein. A bioactive neublastin polypeptide includes a polypeptide that, for example, when dimerized, alone or in the presence of a cofactor (such as GFRα3, or RET), binds to RET, induces dimerization of RET, and autophosphorylation of RET.

The polypeptides of the invention may in particular be an N-glycosylated polypeptide, which polypeptide preferably is glycosylated at the N-residues indicated in the sequence listings.

In some embodiments, a polypeptide of the invention has the amino acid sequence presented as SEQ ID NO:6, holding a glycosylated asparagine residue at position 122; or the amino acid sequence presented as SEQ ID NO:14, holding a glycosylated asparagine residue at position 95, or the analogous position in any mutated neublastin polypeptide when aligned by, e.g., ClustalW computer software.

In some embodiments, the polypeptide of the invention has the amino acid sequence presented as SEQ ID NO:23, referred to herein as NBN113-N95K, containing a lysine residue substituted for the asparagine residue at position 95 of SEQ ID NO:2; or the amino acid sequence presented as SEQ ID NO:24, referred to herein as NBN106-N95K; or the analogous position in any mutated neublastin polypeptide when aligned by, e.g., ClustalW computer software.

This invention also includes mutated neublastin fusion proteins, such as Ig-fusions, as described, e.g., in U.S. Pat. No. 5,434,131, or serum albumin fusions.

In some embodiments, the invention provides a polypeptide having the amino acid sequence shown as SEQ ID NO:1 with the exception of one substitution, or an amino acid sequence that has at least about 85%, preferably at least about 90%, more preferably at least about 95%, more preferably at least about 98%, and most preferably at least about 99% identity to the sequence presented as SEQ ID NO:1.

In other embodiments, the invention provides a polypeptide having the amino acid sequence of SEQ ID NO:2 with the exception of one substitution, or an amino acid sequence that has at least about 85%, preferably at least about 90%, more preferably at least about 95%, more preferably at least about 98%, and most preferably at least about 99% identity to the sequence presented as SEQ ID NO:2.

In some embodiments, the invention provides a polypeptide having the amino acid sequence of SEQ ID NO:3 with the exception of one substitution, or an amino acid sequence that has at least about 85%, preferably at least about 90%, more preferably at least about 95%, more preferably at least about 98%, and most preferably at least about 99% identity to the sequence presented as SEQ ID NO:3.

In some embodiments, the invention provides a polypeptides having the amino acid sequence of SEQ ID NO:4 with the exception of one substitution, or an amino acid sequence that has at least about 85%, preferably at least about 90%, more preferably at least about 95%, more preferably at least about 98%, and most preferably at least about 99% identity to the sequence presented as SEQ ID NO:4.

In some embodiments, the invention provides a polypeptide having the amino acid sequence of SEQ ID NO:5 with the exception of one substitution, or an amino acid sequence that has at least about 85%, preferably at least about 90%, more preferably at least about 95%, more preferably at least about 98%, and most preferably at least about 99% identity to the sequence presented as SEQ ID NO:5.

In some embodiments, the invention provides a polypeptides having the amino acid sequence of SEQ ID NO:6 with the exception of one substitution, or an amino acid sequence that has at least about 85%, preferably at least about 90%, more preferably at least about 95%, more preferably at least about 98%, and most preferably at least about 99% identity to the sequence presented as SEQ ID NO:6.

In some embodiments, the invention provides a polypeptide having the amino acid sequence of SEQ ID NO:7 with the exception of one substitution, or an amino acid sequence that has at least about 85%, preferably at least about 90%, more preferably at least about 95%, more preferably at least about 98%, and most preferably at least about 99% identity to the sequence presented as SEQ ID NO:7.

In some embodiments, the invention provides a polypeptide having the amino acid sequence of any one of SEQ ID NOs:8-21 with the exception of one substitution, or an amino acid sequence that has at least about 85%, preferably at least about 90%, more preferably at least about 95%, more preferably at least about 98%, and most preferably at least about 99% identity to the sequence presented as any one of SEQ ID NOs:8-21.

In some embodiments, the invention provides a polypeptide having the amino acid sequence of SEQ ID NO:36 with the exception of one substitution, or an amino acid sequence that has at least about 85%, preferably at least about 90%, more preferably at least about 95%, more preferably at least about 98%, and most preferably at least about 99% identity to the sequence presented as SEQ ID NO:36.

In further embodiments, the invention provides a polypeptide having the amino acid sequence of any one of SEQ ID NOS:1-21 and 36 with the exception of one substitution, or an amino acid sequence that has at least about 85%, preferably at least about 90%, more preferably at least about 95%, more preferably at least about 98%, and most preferably at least about 99% identity to any one of the sequences presented as SEQ ID NOS:1-21 and 36.

In other embodiments, the mutated polypeptide of the invention holds the GDNF subfamily fingerprint, i.e. the conserved cysteine amino acid residues designated in Tables 3 and 4.

In some embodiments, the invention provides a mutated polypeptide encoded by a polynucleotide sequence capable of hybridizing under high stringency conditions with the polynucleotide sequence encoding the polypeptide of SEQ ID NO:1, its complementary strand, or a sub-sequence thereof. In some embodiments, the mutated polypeptide of the invention is encoded by a polynucleotide sequence having at least 70% identity to the polynucleotide sequence encoding the polypeptide of SEQ ID NO:1.

In some embodiments, the invention provides novel polypeptides encoded by a polynucleotide sequence capable of hybridizing under high stringency conditions with the polynucleotide sequence encoding the polypeptide of SEQ ID NO:2, its complementary strand, or a sub-sequence thereof. In some embodiments, the mutated polypeptide of the invention is encoded by a polynucleotide sequence having at least 70% identity to the polynucleotide sequence encoding the polypeptide of SEQ ID NO:2.

In some embodiments, the invention provides mutated polypeptides encoded by a polynucleotide sequence capable of hybridizing under high stringency conditions with the polynucleotide sequence encoding the polypeptide of any one of SEQ ID NOs:8-21, its complementary strand, or a sub-sequence thereof. In other embodiments, the mutated polypeptide of the invention is encoded by a polynucleotide sequence having at least 70% identity to the polynucleotide sequence encoding the polypeptide of any one of SEQ ID NO: 8-21.

In some embodiments, the invention provides novel polypeptides encoded by a polynucleotide sequence capable of hybridizing under high stringency conditions with the polynucleotide sequence encoding the polypeptide of SEQ ID NO:36, its complementary strand, or a sub-sequence thereof. In some embodiments, the mutated polypeptide of the invention is encoded by a polynucleotide sequence having at least 70% identity to the polynucleotide sequence encoding the polypeptide of SEQ ID NO:36.

Biological Origin

A non-conjugated neublastin polypeptide dimer can be isolated and then conjugated to one or more polymers to obtain a polymer conjugated neublastin polypeptide dimer of the invention. The neublastin polypeptide dimer can be isolated from a mammalian cell, preferably from a human cell or from a cell of murine origin or from a cell of Chinese hamster ovary origin.

Neurotrophic Activity

Modified neublastin polypeptides, including truncated neublastin polypeptides, of the invention are useful for moderating metabolism, growth, differentiation, or survival of a nerve or neuronal cell. In particular, modified neublastin polypeptides are used to treat or alleviate a disorder or disease of a living animal, e.g., a human, which disorder or disease is responsive to the activity of a neurotrophic agent. Such treatments and methods are described in more detail below.

Pharmaceutical Compositions Comprising Neublastin-Polymer Conjugates

Also provided is a pharmaceutical composition comprising a modified neublastin polypeptide dimer of the present invention.

The polymer-neublastin conjugates of the invention may be administered per se as well as in the form of pharmaceutically acceptable esters, salts, and other physiologically functional derivatives thereof. In such pharmaceutical and medicament formulations, the polymer-conjugated neublastin conjugate preferably is utilized together with one or more pharmaceutically acceptable carrier(s) and optionally any other therapeutic ingredients.

The carrier(s) must be pharmaceutically acceptable in the sense of being compatible with the other ingredients of the formulation and not unduly deleterious to the recipient thereof. The polymer-conjugated neublastin is provided in an amount effective to achieve a desired pharmacological effect or medically beneficial effect, as described herein, and in a quantity appropriate to achieve the desired bioavailable in vivo dose or concentration.

The formulations include those suitable for parenteral as well as non parenteral administration, and specific administration modalities include oral, rectal, buccal, topical, nasal, ophthalmic, subcutaneous, intramuscular, intravenous, transdermal, intrathecal, intra-articular, intra-arterial, sub-arachnoid, bronchial, lymphatic, vaginal, and intra-uterine administration. Formulations suitable for aerosol and parenteral administration, both locally and systemically, are preferred.

When the polymer-conjugated neublastin is utilized in a formulation comprising a liquid solution, the formulation advantageously may be administered orally, bronchially, or parenterally. When the polymer-conjugated neublastin is employed in a liquid suspension formulation or as a powder in a biocompatible carrier formulation, the formulation may be advantageously administered orally, rectally, or bronchially. Alternatively, it may be administered nasally or bronchially, via nebulization of the powder in a carrier gas, to form a gaseous dispersion of the powder that is inspired by the patient from a breathing circuit comprising a suitable nebulizer device.

The formulations comprising the proteins of the present invention may conveniently be presented in unit dosage forms and may be prepared by any of the methods well known in the art of pharmacy. Such methods generally include the step of bringing the active ingredient(s) into association with a carrier that constitutes one or more accessory ingredients.

Typically, the formulations are prepared by uniformly and intimately bringing the active ingredient(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each comprising a predetermined amount of the active ingredient as a powder or granules; or a suspension in an aqueous liquor or a non-aqueous liquid, such as a syrup, an elixir, an emulsion, or a draught.

Formulations suitable for parenteral administration conveniently comprise a sterile aqueous preparation of the active conjugate, which preferably is isotonic with the blood of the recipient (e.g., physiological saline solution). Such formulations may include suspending agents and thickening agents or other microparticulate systems which are designed to target the compound to blood components or one or more organs. The formulations may be presented in unit-dose or multi-dose form.

Nasal spray formulations comprise purified aqueous solutions of the active conjugate with preservative agents and isotonic agents. Such formulations are preferably adjusted to a pH and isotonic state compatible with the nasal mucus membranes.

Formulations for rectal administration may be presented as a suppository with a suitable carrier such as cocoa butter, hydrogenated fats, or hydrogenated fatty carboxylic acid. Ophthalmic formulations such as eye drops are prepared by a similar method to the nasal spray, except that the pH and isotonic factors are preferably adjusted to match that of the eye.

Topical formulations comprise the conjugates of the invention dissolved or suspended in one or more media, such as mineral oil, petroleum, polyhydroxy alcohols, or other bases used for topical pharmaceutical formulations.

In addition to the aforementioned ingredients, the formulations of this invention may further include one or more accessory ingredient(s) selected from diluents, buffers, flavoring agents, disintegrants, surface active agents, thickeners, lubricants, preservatives (including antioxidants), and the like. The foregoing considerations apply also to the neublastin fusion proteins of the invention (e.g., neublastin-human serum albumin fusion proteins).

Accordingly, the present invention includes the provision of suitable fusion proteins for in vitro stabilization of a polymer-conjugated neublastin conjugate in solution, as a preferred illustrative application of the invention. The fusion proteins may be employed for example to increase the resistance to enzymatic degradation of the polymer-conjugated neublastin polypeptide and provides a means of improving shelf life, room temperature stability, and the like. It is understood that the foregoing considerations apply also to the neublastin-serum albumin fusion proteins (including the human neublastin-human serum albumin fusion proteins) of the invention.

Methods of Treatment

The compositions of the invention may be used for treating or alleviating a disorder or disease in a mammal, e.g., a primate including a human, which disorder or disease is responsive to the activity of neurotrophic agents.

The compositions of the invention may be used directly via, e.g., injected, implanted or ingested pharmaceutical compositions to treat a pathological process responsive to the neublastin polypeptides. The compositions may be used for alleviating a disorder or disease of a living animal body, including a human, which disorder or disease is responsive to the activity of neurotrophic agents. The disorder or disease may in particular be damage of the nervous system caused by trauma, surgery, ischemia, infection, metabolic diseases, nutritional deficiency, malignancy or toxic agents, and genetic or idiopathic processes.

The damage may in particular have occurred to sensory neurons or retinal ganglion cells, including neurons in the dorsal root ganglia or in any of the following tissues: the geniculate, petrosal and nodose ganglia; the vestibuloacoustic complex of the eighth cranial nerve; the ventrolateral pole of the maxillomandibular lobe of the trigeminal ganglion; and the mesencephalic trigeminal nucleus.

In some embodiments of the method of the invention, the disease or disorder is a neurodegenerative disease involving lesioned and traumatic neurons, such as traumatic lesions of peripheral nerves, the medulla, and/or the spinal cord, cerebral ischemic neuronal damage, neuropathy and especially peripheral neuropathy, peripheral nerve trauma or injury, ischemic stroke, acute brain injury, acute spinal cord injury, nervous system tumors, multiple sclerosis, exposure to neurotoxins, metabolic diseases such as diabetes or renal dysfunctions and damage caused by infectious agents, neurodegenerative disorders including Alzheimer's disease, Huntington's disease, Parkinson's disease, Parkinson-Plus syndromes, progressive Supranuclear Palsy (Steele-Richardson-Olszewski Syndrome), Olivopontocerebellar Atrophy (OPCA), Shy-Drager Syndrome (multiple systems atrophy), Guamanian parkinsonism dementia complex, amyotrophic lateral sclerosis, or any other congenital or neurodegenerative disease, and memory impairment connected to dementia.

In some embodiments, sensory and/or autonomic system neurons can be treated. In particular, nociceptive and mechanoreceptive neurons can be treated, more particularly A-delta fiber, C-fiber and A-beta fiber neurons. In addition, sympathetic and parasympathetic neurons of the autonomic system can be treated.

In some embodiments, motor neuron diseases such as amyotrophic lateral sclerosis ("ALS") and spinal muscular atrophy can be treated. In other embodiments, the neublastin molecules of this invention to can be used to enhance nerve recovery following traumatic injury. Alternatively, or in addition, a nerve guidance channel with a matrix containing polymer-conjugated neublastin polypeptides, or fusion or conjugates of mutated neublastin polypeptides can be used in the herein described methods. Such nerve guidance channels are disclosed, e.g., U.S. Pat. No. 5,834,029.

In some embodiments, the compositions disclosed herein (and pharmaceutical compositions comprising same) are used in the treatment of peripheral neuropathies. Among the peripheral neuropathies included for treatment with the molecules of this invention are trauma-induced neuropathies, e.g., those caused by physical injury or disease state, physical damage to the brain, physical damage to the spinal cord, stroke associated with brain damage, and neurological disorders related to neurodegeneration. Also included herein are those neuropathies secondary to infection, toxin exposure, and drug exposure. Still further included herein are those neuropathies secondary to systemic or metabolic disease. For example, the herein disclosed compositions can also be used to treat chemotherapy-induced neuropathies (such as those caused by delivery of chemotherapeutic agents, e.g., taxol or cisplatin); toxin induced neuropathies, drug-induced neuropathies, vitamin-deficiency-induced neuropathies; idiopathic neuropathies; diabetic neuropathies; and post-herpetic neuralgias. See, e.g., U.S. Pat. Nos. 5,496,804 and 5,916,555.

Additional conditions that can be treated according to the invention are mono-neuropathies, mono-multiplex neuropathies, and poly-neuropathies, including axonal and demyelinating neuropathies.

In some embodiments, the compositions of the invention (and pharmaceutical compositions comprising same) are used in the treatment of various disorders in the eye, including photoreceptor loss in the retina in patients afflicted with macular degeneration, retinitis pigmentosa, glaucoma, and similar diseases.

Methods and Pharmaceutical Compositions

This invention provides methods for treating neuropathic pain, for treating tactile allodynia, and for reducing loss of pain sensitivity associated with neuropathy. The present methods use polymer conjugated neublastin polypeptide dimers, including dimers comprising bioactive full-length neublastin polypeptides or bioactive truncated neublastin polypeptides. In addition, the invention provides pharmaceutical compositions comprising a polymer conjugated neublastin polypeptide dimer suspended, dissolved, or dispersed in a pharmaceutically acceptable carrier.

1. Treatment of Neuropathic Pain

In one embodiment, the invention includes a method for treating neuropathic pain in a subject comprising administering to the subject an effective amount of a polymer conjugated neublastin polypeptide dimer. In some embodiments, the invention includes a method for treating neuropathic pain in a subject comprising administering to the subject a pharmaceutically effective amount of a polymer conjugated neublastin polypeptide dimer comprising, for example, wild-type, truncated or mutated neublastin polypeptides, including, e.g., any one of SEQ ID NOS:1, 2, 6-21 and 36 or a mutated form thereof, either alone, or by also administering to the subject an effective amount of an analgesia-inducing compound selected from the group consisting of opioids, anti-arrhythmics, topical analgesics, local anaesthetics, anticonvulsants, antidepressants, corticosteroids and non-steroidal anti-inflammatory drugs (NSAIDS). In a preferred embodiment, the analgesia-inducing compound is an anticonvulsant. In another preferred embodiment, the analgesia-inducing compound is gabapentin ((1-aminomethyl)cyclohexane acetic acid) or pregabalin (S-(+)-4-amino-3-(2-methylpropyl)butanoic acid).

The neublastin polypeptides and nucleic acids of this invention (and pharmaceutical compositions comprising polymer conjugated neublastin polypeptide dimers described herein) are used in the treatment of pain associated with peripheral neuropathies. Among the peripheral neuropathies which can be treated according to this invention are trauma-induced neuropathies, e.g., those caused by physical injury or disease state, physical damage to the brain, physical damage to the spinal cord, stroke associated with brain damage, and neurological disorders related to neurodegeneration.

The invention also provides treatments of chemotherapy-induced neuropathies (such as those caused by delivery of chemotherapeutic agents, e.g., taxol or cisplatin); toxin-induced neuropathies, drug-induced neuropathies, pathogen-induced (e.g., virus induced) neuropathies, vitamin-deficiency-induced neuropathies; idiopathic neuropathies; and diabetic neuropathies. See, e.g., U.S. Pat. Nos. 5,496,804 and 5,916,555, each herein incorporated by reference. The invention still further can be used for treatment of mono-neuropathies, mono-multiplex neuropathies, and poly-neuropathies, including axonal and demyelinating neuropathies, using the neublastin nucleotides and polypeptides of this invention.

The neuropathic pain may be associated with a number of peripheral neuropathies, including: (a) trauma-induced neuropathics, (b) chemotherapy-induced neuropathies, (c) toxin-induced neuropathies (including but not limited to neuropathies induced by alcoholism, vitamin B6 intoxication, hexacarbon intoxication, amiodarone, chloramphenicol, disulfiram, isoniazide, gold, lithium, metronidazole, misonidazole, nitrofurantoin), (d) drug-induced neuropathies, including therapeutic drug-induced neuropathic pain (such as caused by anti-cancer agents, particularly anti-cancer agents selected from the group consisting of taxol, taxotere, cisplatin, nocodazole, vincristine, vindesine and vinblastine; and such as caused by anti-viral agents, particularly anti-viral agents selected from the group consisting of ddI, DDC, d4T, foscarnet, dapsone, metronidazole, and isoniazid), (e) vitamin-deficiency-induced neuropathies (including but not limited to vitamin B12 deficiency, vitamin B6 deficiency, and vitamin E deficiency), (f) idiopathic neuropathies, (g) diabetic neuropathies, (h) pathogen-induced nerve damage, (i) inflammation-induced nerve damage, (j) neurodegeneration, (k) hereditary neuropathy (including but not limited to Friedreich ataxia, familial amyloid polyneuropathy, Tangier disease, Fabry disease), (l) metabolic disorders (including but not limited to renal insufficiency and hypothyroidism), (m) infectious and viral neuropathies (including but not limited to neuropathic pain associated with leprosy, Lyme disease, neuropathic pain associated with infection by a virus, particularly a virus selected from the group consisting of a herpes virus (e.g. herpes zoster which may lead to post-herpetic neuralgia), a human immunodeficiency virus (HIV), and a papilloma virus), (n) auto-immune neuropathies (including but not limited to Guillain-Barre syndrome, chronic inflammatory de-myelinating polyneuropathy, monoclonal gammopathy of undetermined significance and polyneuropathy), (o) trigeminal neuralgia and entrapment syndromes (including but not limited to Carpel tunnel), and (p) other neuropathic pain syndromes including post-traumatic neuralgia, phantom limb pain, multiple sclerosis pain, complex regional pain syndromes (including but not limited to reflex sympathetic dystrophy, causalgia), neoplasia-associated pain, vasculitic/angiopathic neuropathy, and sciatica. Neuropathic pain may be manifested as allodynia, hyperalgesia, spontaneous pain or phantom pain.

2. Treatment of Tactile Allodynia

The term "tactile allodynia" typically refers to the condition in a subject where pain is evoked by stimulation of the skin (e.g. touch) that is normally innocuous. This invention includes a method for treating tactile allodynia in a subject.

In some embodiments, tactile allodynia is treated by administering to the subject a pharmaceutically effective amount of a polymer conjugated mutated neublastin polypeptide dimer alone.

In a related embodiment, the invention includes a method for treating tactile allodynia in a subject, either by administering to the subject an effective amount of a polymer conjugated neublastin polypeptide dimer containing truncated wild-type or mutated neublastin polypeptides, including, e.g., at least one of SEQ ID NOS:1, 2, 6-21 and 36 or a mutated form thereof, either alone, or by administering to the subject an effective amount of a neublastin polypeptide with an effective amount of an analgesia-inducing compound selected from the group consisting of opioids, anti-arrhythmics, topical analgesics, local anaesthetics, anticonvulsants, antidepressants, corticosteroids and NSAIDS. In a preferred embodiment, the analgesia-inducing compound is an anticonvulsant. In another preferred embodiment, the analgesia-inducing compound is gabapentin ((1-aminomethyl)cyclohexane acetic acid) or pregabalin (S-(+)-4-amino-3-(2-methylpropyl)butanoic acid).

In some embodiments, a polymer conjugated mutated neublastin polypeptide dimer is administered in association with a therapeutic agent, including but not limited to an anti-cancer agent or an anti-viral agent. Anti-cancer agents include, but are not limited to, taxol, taxotere, cisplatin, nocodazole, vincristine, vindesine and vinblastine. Anti-viral agents include, but are not limited to, ddI, DDC, d4T, foscarnet, dapsone, metronidazole, and isoniazid.

3. Treatment for Reduction of Loss of Pain Sensitivity

In another embodiment, the invention includes a method for reducing the loss of pain sensitivity in a subject afflicted with a neuropathy. In a preferred embodiment, the neuropathy is diabetic neuropathy. In a preferred embodiment, the loss of pain sensitivity is a loss in thermal pain sensitivity. This invention contemplates both prophylactic and therapeutic treatment.

In prophylactic treatment, a polymer conjugated mutated neublastin polypeptide dimer is administered to a subject at risk of developing loss of pain sensitivity; such subjects would be expected to be subjects with an early stage neuropathy. The treatment with neublastin under such circumstances would serve to treat at-risk patients preventively.

In therapeutic treatment, a polymer conjugated mutated neublastin polypeptide dimer is administered to a subject who has experienced loss of pain sensitivity as a result of affliction with a neuropathy; such subjects would be expected to be subjects with a late stage neuropathy. The treatment with a polymer conjugated mutated neublastin polypeptide dimer under such circumstances would serve to rescue appropriate pain sensitivity in the subject.

4. Treatment of Viral Infections and Viral-Associated Neuropathies

Prophylactic treatment of infectious and viral neuropathies is contemplated. Prophylactic treatment is indicated after determination of viral infection and before onset of neuropathic pain. During treatment, a polymer conjugated mutated neublastin polypeptide dimer is administered to prevent appearance of neuropathic pain including but not limited to neuropathic pain associated with leprosy, Lyme disease, neuropathic pain associated with infection by a virus, particularly a virus selected from the group consisting of a herpes virus (and more particularly by a herpes zoster virus, which may lead to post-herpetic neuralgia), a human immunodeficiency virus (HIV), and a papilloma virus). In an alternative embodiment, a polymer conjugated mutated neublastin polypeptide dimer is administered to reduce the severity of neuropathic pain, should it appear.

Symptoms of acute viral infection often include the appearance of a rash. Other symptoms include, for example, the development of persistent pain in the affected area of the body, which is a common complication of a herpes zoster infection (shingles). Post-herpetic neuralgia can last for a month or more, and may appear several months after any rash-like symptoms have disappeared.

5. Treatment of Painful Diabetic Neuropathy

Prophylactic treatment of painful diabetic neuropathy is contemplated. Prophylactic treatment of diabetic neuropathies would commence after determination of the initial diagnosis of diabetes or diabetes-associated symptoms and before onset of neuropathic pain. Prophylactic treatment of painful diabetic neuropathy may also commence upon determining that a subject is at risk for developing diabetes or diabetes-associated symptoms. During treatment, a polymer conjugated mutated neublastin polypeptide dimer is administered to prevent appearance of neuropathic pain. In an alternative embodiment, a polymer conjugated mutated neublastin polypeptide dimer is administered to reduce the severity of neuropathic pain that has already appeared.

6. Nervous System Disorders

In a further aspect, the invention provides a method of treating or preventing a nervous system disorder in a subject (such as a human), by administering to a subject in need thereof a therapeutically effective amount of a polymer-conjugated neublastin polypeptide, a composition containing a neublastin polypeptide or mutated neublastin polypeptide coupled to a polymer, or a complex that includes a stable, aqueous soluble conjugated neublastin polypeptide or mutated neublastin polypeptide complex comprising a neublastin polypeptide or mutated neublastin polypeptide coupled to a polyalkylene moiety such as, e.g., PEG.

The nervous system disorder can be a peripheral nervous system disorder, such as a peripheral neuropathy or a neuropathic pain syndrome. Humans are preferred subjects for treatment.

A polymer-conjugated neublastin polypeptide dimer of the invention is useful for treating a defect in a neuron, including without limitation lesioned neurons and traumatized neurons. Peripheral nerves that experience trauma include, but are not limited to, nerves of the medulla or of the spinal cord. Inventive polymer-conjugated neublastin polypeptide dimers are useful in the treatment of neurodegenerative disease, e.g., cerebral ischemic neuronal damage; neuropathy, e.g., peripheral neuropathy, Alzheimer's disease, Huntington's disease, Parkinson's disease, amyotrophic lateral sclerosis (ALS). Such neublastin polypeptide dimers can be used in the treatment of impaired memory, e.g., memory impairment associated with dementia.

Additional examples of conditions or diseases are disorders of the peripheral nervous system, the medulla, or the spinal cord, as well as trauma-induced neuropathies, chemotherapy-induced neuropathies, toxin-induced neuropathies, drug-induced neuropathies, vitamin-deficiency-induced neuropathies; idiopathic neuropathies; and diabetic neuropathies, neuropathic pain associated with toxin-induced nerve damage, pathogen-induced nerve damage, inflammation-induced nerve damage, or neurodegeneration. An inventive neublastin polypeptide dimer is additionally useful for treating neuropathic pain, for treating tactile allodynia and for reducing loss of pain sensitivity associated with neuropathy.

7. Dosage

The foregoing methods contemplate administering a to the subject, preferably systemically, a formulation comprising a polymer conjugated mutated neublastin polypeptide dimer that may or may not be truncated at a dosage from 0.01 µg/kg to 1000 µg/kg body weight of the subject, per dose. Preferably the dosage is from 1 µg/kg to 100 µg/kg body weight of the subject, per dose. More preferably the dosage is from 1 µg/kg to 30 µg/kg body weight of the subject, per dose, e.g., from 3 µg/kg to 10 µg/kg body weight of the subject, per dose. Therapeutically effective amounts of the formulation of the invention may be administered to a subject in need thereof in a dosage regimen ascertainable by one of skill in the art, without undue experimentation.

8. Delivery

The polypeptide dimer used in the foregoing methods can be administered via any suitable delivery system, and preferably from the group consisting of intravenous delivery, intramuscular delivery, intrapulmonary delivery, subcutaneous delivery, and intraperitoneal delivery, most preferably via intramuscular delivery, intravenous delivery, or subcutaneous delivery. The neublastin polypeptide used in the foregoing methods can also be administered via intrathecal delivery.

Administration of a polymer-conjugated neublastin polypeptide dimer can be, e.g., systemic or local. The formulations include those suitable for parenteral as well as non parenteral administration, and specific administration modalities include oral, rectal, buccal, topical, nasal, ophthalmic, subcutaneous, intramuscular, intravenous, transdermal, intrathecal, intra-articular, intra-arterial, sub-arachnoid, bronchial, lymphatic, vaginal, and intra-uterine administration. Formulations suitable for aerosol and parenteral administration, both locally and systemically, are included. Preferred formulations are suitable for subcutaneous, intramuscular, or intravenous administration.

8. Regimes

In some embodiments, the frequency of dosing for the polypeptide dimer of the invention provides for administering to the subject a formulation three times a week for two weeks. In order to optimize therapeutic efficacy, a polymer conjugated mutated neublastin polypeptide dimer is first administered at different dosing regimens. The unit dose and regimen depend on factors that include, e.g., the species of mammal immunized, its immune status, the body weight of the mammal. Typically, protein levels in tissue are monitored using appropriate screening assays as part of a clinical testing procedure, e.g., to determine the efficacy of a given treatment regimen.

The frequency of dosing for a polymer conjugated mutated neublastin polypeptide dimer of this invention is within the skills and clinical judgement of physicians. Typically, the administration regime is established by clinical trials which may establish optimal administration parameters. However, the practitioner may vary such administration regimes according to the subject's age, health, weight, sex and medical status. The frequency of dosing may also vary between acute and chronic treatments for neuropathy. In addition, the frequency of dosing may be varied depending on whether the treatment is prophylactic or therapeutic.

The invention is further illustrated in the following non-limiting examples.

EXAMPLES

Example 1

Bioavailability of Amino-Terminal PEGylated Neublastin

CHO cell—and *E. coli*—derived recombinant neublastins were observed to be rapidly cleared from circulation if administered intravenously in rats. The proteins were below the threshold of detection in the serum following subcutaneous administration. To increase bioavailability of neublastin, PEGylated forms of mutated neublastin were constructed.

Because no lysines occur in the neublastin sequence, amine-specific PEGylation chemistries will result in PEGylation of a wild-type neublastin polypeptide at its amino terminus. Thus, for each neublastin dimer, two PEG moieties should be attached. Accordingly, PEG forms were first directly targeted to the amino-terminus through amine specific chemistries. Surprisingly, PEGylation of *E. coli* expressed wild-type neublastin, even with two 20 kDa PEGs attached, had little benefit on half life, indicating that a mechanism based clearance pathway was overriding the enhancement in half life that was expected to be achieved by PEGylation.

Example 2

Construction of a PEGylated Mutated Neublastin (N95K)

The bioavailability of mutated neublastin forms PEGylated at internal amino acid residues was next examined. A series of four mutants replacing naturally occurring residues at positions 14, 39, 68, and 95, when numbered as shown in SEQ ID NO:1, were designed to insert lysines at selected sites in the sequence. These lysines would provide alternative sites for PEG attachment. These sites were selected using the crystal structure of GDNF (Nat. Struct. Biol. 4: 435-8, 1997) as a framework to identify surface residues. The persephin/neublastin chimera mutagenesis study (J. Biol. Chem. 275: 3412-20, 2000) was used to identify functionally important regions of the structure that should be avoided.

In order to express the wild-type neublastin gene in *E. coli*, syngenes were constructed with lower GC content and preferred *E. coli* codons. The syngene was cloned into two vectors, pET19b and pMJB164, a derivative of pET19b. In pET19b, the sequence encoding the mature domain of neublastin (NBN113) is directly fused to an initiating methionine. In pMJB164, the mature domain of neublastin is fused to a histidine tag (i.e. 10 histidines) and separated from the histidine tag by an enterokinase cleavage site (SEQ ID NOs: 35 and 36). The initiating methionine precedes the histidine tag.

TABLE 5

His-tagged Wild-Type Neublastin
Nucleotide and Polypeptide Sequence

```
His-tagged NBN
  1 ATG GGC CAT CAT CAT CAT CAT CAT CAT CAT CAT CAC TCG AGC GGC  45 (SEQ ID NO: 35)
  1  M   G   H   H   H   H   H   H   H   H   H   H   S   S   G   15 (SEQ ID NO: 36)

46 CAT ATC GAC GAC GAC GAC AAG GCT GGA GGA CCG GGA TCT CGT GCT  90
 16  H   I   D   D   D   D   K   A   G   G   P   G   S   R   A   30

91 CGT GCA GCA GGA GCA CGT GGC TGT CGT CTG CGT TCT CAA CTA GTG 135
 31  R   A   A   G   A   R   G   C   R   L   R   S   Q   L   V   45

136 CCG GTG CGT GCA CTC GGA CTG GGA CAC CGT TCC GAC GAA CTA GTA 180
 46  P   V   R   A   L   G   L   G   H   R   S   D   E   L   V   60

181 CGT TTT CGT TTT TGT TCA GGA TCT TGT CGT CGT GCA CGT TCT CCG 225
 61  R   F   R   F   C   S   G   S   C   R   R   A   R   S   P   75

226 CAT GAT CTA TCT CTA GCA TCT CTA CTA GGA GCC GGA GCA CTA AGA 270
 76  H   D   L   S   L   A   S   L   L   G   A   G   A   L   R   90

271 CCG CCG CCG GGA TCT AGA CCT GTA TCT CAA CCT TGT TGT AGA CCT 315
 91  P   P   P   G   S   R   P   V   S   Q   P   C   C   R   P  105

316 ACT AGA TAC GAA GCA GTA TCT TTC ATG GAC GTA AAC TCT ACA TGG 360
106  T   R   Y   E   A   V   S   F   M   D   V   N   S   T   W  120

361 AGA ACC GTA GAT AGA CTA TCT GCA ACC GCA TGT GGC TGT CTA GGA 405
121  R   T   V   D   R   L   S   A   T   A   C   G   C   L   G  135

406 TGA TAA TAG  414
136  *   *   *
```

Two of the mutations (R39 and R68) were targeted at a region that, based on the distribution of positive charges on the surface, might represent a heparin binding site. This site likely contributes to the rapid clearance of the protein. A third site was targeted at N95, the natural glycosylation site in wild-type neublastin. This site is naturally modified with a complex carbohydrate structure. Therefore, modification with PEG at this site was not expected to impact function. The fourth site (R14) was selected in a region that was not covered by any other of the modifications. A mutant in which the asparagine residue at position 95 was replaced with a lysine (the "N95K mutant") was chosen for the studies disclosed herein.

Four different mutated rat neublastins comprising one or more alterations in the wild-type sequence of rat neublastin polypeptide were constructed. These mutated neublastins contained single amino acid substitutions: R14K; R68K; R39K; or N95K. Table 1A identifies these exemplary point mutations in bold. In the "$X_1N_1X_2$" nomenclature, $X_1$ refers to an amino acid of a wild-type neublastin polypeptide, $N_1$ refers to the numerical position of the $X_1$ amino acids in the sequence, as numbered according to SEQ ID NO:1, and $X_2$ refers to an amino acid substituted for the wild-type amino acid at the indicated numerical position $N_1$.

To construct the rat N95K neublastin mutation, site-directed mutagenesis was performed on pCMB020, a plasmid encoding wild-type rat neublastin. The wild-type rat neublastin nucleic and the amino acid sequence of the polypeptide encoded thereby are presented below:

TABLE 6

Wild-type Rat NBN Sequences

```
  1 ATGGAACTGG GACTTGGAGA GCCTACTGCA TTGTCCCACT GCCTCCGGCC  (SEQ ID NO: 25)

51 TAGGTGGCAA CCAGCCTTGT GGCCAACCCT AGCTGCTCTA GCCCTGCTGA

101 GCAGCGTCAC AGAAGCTTCC CTGGACCCAA TGTCCCGCAG CCCCGCCTCT

151 CGCGATGTTC CCTCCCCGGT CCTGGCGCCC CCAACAGACT ACCTACCTCG

201 GGGACACACC GCACATCTGT GCAGCGAAAG ACCCCTGCGA CCACCGCCGC

251 AGTCTCCTCA GCCCGCACCC CCACCACCGG GTCCCGCGCT CCAGTCTCCT

301 CCCGCTGCGC TCCGCGGGGC ACGCGCGGCG CGTGCAGGAA CCCGGAGCAG

351 CCGCCCACGG GCTACAGATG CGCGCGGCTG CCGCCTGCGC TCACAGCTGG

401 TGCCGGTGAG CGCTCTCGGC CTGGCCCACA GCTCCGACGA GCTGATACGT
```

TABLE 6-continued

Wild-type Rat NBN Sequences

```
451 TTCCGCTTCT GCAGCCGTTC GTGCCGCCGA GCACCCTCCC CGCACGATCT

501 CAGCCTGGCC AGCCTGCTGC GCGCCGGGGC CCTGCGGTCT CCTCCCGGGT

551 CCCGGCCGAT CAGCCAGCCC TGTTGCCGGC CCACTCGCTA TGAGGCAGTC

601 TCCTTCATGG ACGTGAACAG CACCTGGAGA ACCGTGGACC ATCTCTCCGC

651 CACCGCCTGC GGCTGTCTGG GCTGA

1 MELGLGEPTA LSHCLRPRWQ PALWPTLAAL ALLSSVTEAS LDPMSRSPAS  (SEQ ID NO: 26)

51 RDVPSPVLAP PTDYLPGGHT AHLCSERALR PPPQSPQPAP PPPGPALQSP

101 PAALRGARAA RAGTRSSRAR ATDARGCRLR SQLVPVSALG LGHSSDELIR

151 FRFCSGSCRR ARSPHDLSLA SLLGAGALRS PPGSRPISQP CCRPTRYEAV

201 SFMDVNSTWR TVDHLSATAC GCLG*
```

Mutagenesis of pCM020 using oligonucleotides KD3-210 and KD3-211 resulted in formation of the plasmid pCMB027:

```
                                              (SEQ ID NO: 27)
KD3-210
5'-GTATCTTTCATGGACGTTATGTTCTACATGGAGAACC-3'

(SEQ ID NO: 28)
KD3-211
5'-GGTTCTCCATGTAGAACATACGTCCATGAAAGATAC-3'
```

In pCMB027, the codon encoding asparagine at position 95 was replaced with a codon encoding lysine.

A R14K mutated neublastin was formed by replacement of a codon encoding arginine at position 14 with a codon encoding lysine in the neublastin coding sequence of pCMB020. Site-directed mutagenesis was performed on pCMB020 using oligonucleotides KD3-254 and KD3-255:

```
                                              (SEQ ID NO: 29)
KD3-254   5'-GCTCGTGCAACGGATGCAAAAGGCTGTCGTCTGCG-3'

(SEQ ID NO: 30)
KD3-255   5'-CGCAGACGACAGCCTTTTGCATCCGTTGCACGAGC-3'
```

The resulting construct was named pCMB029.

An R68K mutated neublastin was formed by replacement of a codon encoding arginine at position 68 with a codon encoding lysine in the neublastin coding sequence of pCMB020. Site-directed mutagenesis was performed on pCMB020 using oligonucleotides KD3-258 and KD3-259:

```
                                              (SEQ ID NO: 31)
KD3-258
5'-GGAGCCGGAGCACTAAAATCTCCCCCGGGATCTAGACC-3'

(SEQ ID NO: 32)
KD3-259
5'-GGTCTAGATCCCGGGGGAGATTTTAGTGCTCCGGCTCC-3'
```

The resulting construct was named pCMB030.

A R39K mutated neublastin was formed by replacement of arginine at amino acid 39 with lysine in the neublastin coding sequence of pCMB020. Site-directed mutagenesis of pCMB020 was performed using oligonucleotides KD3-256 and KD3-257:

```
                                              (SEQ ID NO: 33)
KD3-256   5'-GACGAATTAATTAAGTTTCGTTTTTGTTCAGG-3'

(SEQ ID NO: 34)
KD3-257   5'-CCTGAACAAAAACGAAACTTAATTAATTCGTC-3'
```

Expression and Characterization of Mutated Neublastin in E. coli

For expression and purification, a plasmid encoding the rat neublastin N95K polypeptide was expressed in E. coli as a His-tagged fusion protein with an enterokinase cleavage site immediately adjacent to the start of the mature 113 amino acid neublastin sequence. The E. coli was grown in a 500 L fermentor and frozen cell paste was provided. The E. coli cells were lysed in a APV Gaulin Press and the rat neublastin N95K recovered from the insoluble washed pellet fraction.

The N95K mutated neublastin was extracted from the pellet with guanidine hydrochloride, refolded, and the His-tag removed with enterokinase (see Example 5). The product was then subjected to chromatography on Ni NTA agarose (Qiagen) and on Bakerbond WP CBX cation exchange resin.

Enterokinase treatment of the His tagged product resulted in an aberrant cleavage of the protein at arginine 7 in the mature sequence. The resulting des 1-7 neublastin product (NBN106-N95K) was fully active in the KIRA ELISA and structurally indistinguishable from the mature form in its susceptibility to guanidine-induced denaturation and therefore was used for subsequent work.

Rat mutated neublastin NBN106-N95K was PEGylated at an average of 3.3 PEG moieties per neublastin molecule using methoxylpoly(ethylene glycol)-succinimidyl propionate (SPA-PEG) with a molecular mass of 10,000 Da as the reactant. The resulting PEGylated product was subjected to extensive characterization including analysis by SDS-PAGE, size exclusion chromatography (SEC), reverse phase HPLC, matrix assisted laser desorption/ionization mass spectrometry (MALD/IMS), peptide mapping, assessment of activity in the KIRA ELISA, and determination of endotoxin content. The purity of the neublastin N95K product prior to PEGylation as measured by SDS-PAGE and SEC was greater than 95%. The neublastin N95K product migrated under nonreducing conditions as a dimer, consistent with its predicted structure. After PEGylation, the resulting product consisted of a series of modified adducts comprising 2 PEGs per molecule, which was 5% of the product, 3 PEGs per molecule, which was 60% of the product, 4 PEGs per molecule, which was 30% of the product, and several minor forms of higher mass. In the PEGylated sample there was no evidence of aggregates. Residual levels of unmodified neublastin in the product were below the limits of quantitation. The endotoxin content of the material is routinely less than 1 EU/mg. The specific activity of the PEGylated neublastin in the KIRA ELISA is 10 nM. The PEGylated product was formulated at 1.1 mg/mL in PBS pH 6.5. The material, which is similar in potency to wild-type neublastin (NBN113), can be supplied as a frozen liquid, which is stored at −70° C.

The R14K, R39K, and R68K mutated neublastin polypeptides were expressed in E. coli and can be subjected to the same methods for purification, PEGylation and assessment of function as described above for the NBN106-N95K neublastin.

Preparation of PEGylated Mutated Neublastin NBN106-N95K 230 mL of the refolded rat N95K mutated neublastin (2.6 mg/mL) that had been produced in *E. coli* and stored at 4° C. in 5 mM sodium phosphate pH 6.5, 100 mM NaCl was diluted with 77 mL of water, 14.4 mL of 1M HEPES pH7.5, and 2.8 g (10 mg/mL final) of PEG SPA 10,000 Da (Shearwater Polymers, Inc.). The sample was incubated at room temperature for 4 hours in the dark, then treated with 5 mM imidazole (final), filtered, and stored overnight at 4° C. The product was generated in two batches one containing 130 mL of the N95K bulk and the other containing 100 mL of the bulk. The PEGylated neublastin was purified from the reaction mixture on Fractogel EMD $S0_3^-$(M) (EM Industries). The column was run at room temperature. All buffers were prepared pyrogen free. Sodium chloride was added to the reaction mixture to a final concentration of 87 mM and the sample was loaded onto a 45 mL Fractogel column (5 cm internal diameter).

The column was washed with one column volume of 5 mM sodium phosphate pH 6.5, 80 mM NaCl, then with three one column volume aliquots of 5 mM sodium phosphate containing 50 mM NaCl. The resin was transferred into a 2.5 cm diameter column and the PEGylated neublastin was eluted from the column with six ten mL steps containing 5 mM sodium phosphate pH 6.5, 400 mM NaCl, three steps containing 500 mL NaCl, and six steps containing 600 mM NaCl. Elution fractions were analyzed for protein content by absorbance at 280 nm and then for extent of modification by SDS-PAGE. Selected fractions were pooled, filtered through a 0.2 μm filter, and diluted with water to 1.1 mg PEGylated rat neublastin/mL. After assessing endotoxin levels in the individual batches, they were pooled and refiltered through a 0.2 μm membrane. The final material was aliquoted and stored at −70° C.

UV Spectrum of Purified PEGylated Mutated Neublastin NBN106-N95K

The UV spectrum (240-340 nm) of PEGylated NBN N95K was taken on the neat sample. The sample was analyzed in triplicate. The PEGylated sample exhibited an absorbance maximum at 275-277 nm and an absorbance minimum at 247-249. This result is consistent with what is observed on the bulk intermediate. The protein concentration of the PEGylated product was estimated from the spectrum using an extinction coefficient of $\Sigma_{280}^{0.1\%}$=0.50. The protein concentration of the PEGylated neublastin bulk is 1.1 mg/mL. No turbidity was present in the sample as evident by the lack of absorbance at 320 nm.

Characterization of PEGylated Mutated Neublastin NBN106-N95K by SDS-PAGE

Aliquots of PEGylated neublastin containing 3, 1.5, 0.75, and 0.3 μg of the product were subjected to SDS-PAGE on a 4-20% gradient gel (Owl). The gel was stained with Coomassie brilliant blue R-250. Molecular weight markers (GIBCO-BRL) were run in parallel.

SDS-PAGE analysis of PEGylated mutated neublastin NBN106-N95K under non reducing conditions revealed a series of bands corresponding to modifications with 2, 3, 4, and more than 4 PEGs per molecule. The major band with apparent mass of 98 kDa contains 3 PEGs per molecules. In the purified PEGylated product, non-PEGylated neublastin was not detected. The presence of a mixture of products with 2, 3 and 4 PEGS attached was verified by MALDI mass spectrometric analysis. The ratio of product containing 2, 3, and 4 PEGs was determined by densitometry and determined to be 7, 62, and 30 percent of the total, respectively.

Characterization of PEGylated Mutated Neublastin NBN106-N95K By Size Exclusion Chromatography PEGylated mutated neublastin NBN106-N95K was subjected to size exclusion chromatography on an analytical Superose 6 HR1O/30 FPLC column using 5 mM MES pH 6.5, 300 mM NaCl as the mobile phase. The column was run at 20 mL/h. Elution fractions were monitored for absorbance at 280 nm. The PEGylated mutated neublastin eluted as a single peak with an apparent molecular weight of about 200 kDa consistent with the large hydrodynamic volume of the PEG. No evidence of aggregates was observed. Free neublastin, which elutes with an apparent molecular mass of about 30 kDa, was not detected in the preparation.

Analysis of PEGylated Mutated Neublastin NBN106-N95K by Reverse Phase HPLC

PEGylated mutated neublastin NBN106-N95K was subjected to reverse phase HPLC on a Vydac $C_4$ (5 μm, 1×250 mm) column. The column was developed using a 60 mm gradient from 40 to 60% B (Buffer A: 0.1% TFA, Buffer B: 75% acetonitrile/0.085% TFA). The column effluent was monitored for absorbance at 214 nm and fractions collected for subsequent analysis. PEGylated NBN106-N95K was fractionated into its various di (60.5 mm), tri (63.3 mm), and tetra (67.8 mm) PEGylated components by reverse phase HPLC on a $C_4$ column. The relative intensities of the peaks suggest that the ratios of the components are 5.4, 60.5, and 30.1%, respectively. Peak identities were verified by MALDI-MS. There was no evidence of non-PEGylated NBN106-N95K (elutes at 5-15 mm) in the product.

Analysis of PEGylated Mutated Neublastin NBN106-N95K by Mass Spectrometry

PEGylated mutated neublastin NBN106-N95K was desalted on a $C_4$ Zip Tip and analyzed by mass spectrometry on a Voyager-DE™ STR (PerSeptive Biosystems) matrix-assisted laser desorption/ionization time-of-flight (MALDI-TOF) mass spectrometer using sinapinic acid as a matrix. 0.5 μL of the purified protein was mixed with 0.5 μL of matrix on the target plate. Mass spectrometry of PEGylated mutated neublastin NBN106-N95K revealed singly and doubly charged forms of three adducts. The observed masses of 43803 Da, 54046 Da, and 64438 Da are consistent with modifications of 2, 3, and 4 PEGs per molecule.

Analysis of PEGylated Mutated Neublastin NBN106-N95K by Peptide Mapping

The specificity of the PEGylation reaction was evaluated by peptide mapping. PEGylated neublastin was separated into di, tri, and tetra PEGylated components, which were then reduced, alkylated, and further separated into their single chain components by HPLC on a $C_4$ column. These components and reduced and alkylated non-PEGylated NBN106-N95K as a control were digested with Asp-N proteinase and the resulting cleavage products were fractionated by reversed phase HPLC on a Vydac $C_{18}$ (5 μm, 1×250 mm) column using a 60 mm gradient from 0 to 60% B (Buffer A: 0.1% TFA, Buffer B: 75% acetonitrile/0.085% TFA). The column effluent was monitored for absorbance at 214 mm.

The rat neublastin sequence contains five internal aspartic acids and therefore was expected to yield a simple cleavage profile when digested with endoproteinase Asp-N. All of the peaks from the Asp-N digest of rat N95K have been identified by mass spectrometry and/or Edman amino-terminal sequencing and thus the peptide map can be used as a simple tool to probe for the sites of modification by the presence or absence of a peak. The identity of the various peaks are summarized below in Table 7.

cell line which expresses Ret and GFRα3, were plated at $2\times10^5$ cells per well in 24-well plates in Dulbecco's modified eagle medium (DMEM), supplemented with 10% fetal bovine serum, and cultured for 18 h at 37° C. and 5% $CO_2$.

The cells were washed with PBS, and treated with serial dilutions of neublastin in 0.25 mL of DMEM for 10 min at 37° C. and 5% $CO_2$. Each sample was analyzed in duplicate. The cells were washed with 1 mL of PBS, and lysed for 1 h at 4° C. with 0.30 mL of 10 mM Tris HCl, pH 8.0, 0.5% Nonidet P40, 0.2% sodium deoxycholate, 50 mM NaF, 0.1 mM $Na_3VO_4$, 1 mM phenylmethylsulfonyl fluoride with gently rocking the plates. The lysates were further agitated by repeated pipetting and 0.25 mL of sample was transferred to a 96-well ELISA plate that had been coated with 5 μg/mL of anti-Ret

TABLE 7

| Peak by Retention Time (mm) | Observed Mass Average | Theoretical Mass Average | Residue Assignment (SEQ ID NO:2) | Amino Acid Sequence |
| --- | --- | --- | --- | --- |
| 38.8 | 1261.1 (M) | 1262.4 | 102-113 | DHLSATACGCLG |
| 40.7 | 1090.9 | 1092.2 | 93-101 | DVKSTWRTV |
| 44.6 | 2508.4 | 2508.9 | 35-54 | DELIRFRFCSGSCRRARSPH |
| 46.0 | 2437.0 | 2437.8 | 12-34 | DARGCRLRSQLVPVSALGLGHSS |
| 51.4 | 3456.7 | 3456.0 | 55-86 | DLSLAS...CRPTRY |
| 51.9 | 4134.4 | | 55-92(oxid) | DLSLAS...CRPTRYEAVSFM |
| 53.2 | 4136.3 * | 4120.8 | 55-92 | DLSLAS...CRPTRYEAVSFM |

(M) monoisotopic mass
* due to oxidation of methionine containing peptide on MALDI.

Since neublastin naturally exists as a homodimer, the rat mutated neublastin NBN106-N95K product contains four potential sites for PEGylation, the two amino-terminal amines from each of the chains and the two N95K sites that were engineered into the construct. In the peptide map of the di-PEGylated chain, only the peak that contains the peptide with the N95K mutation was altered by the PEG modification. None of the other peaks were affected by the PEG modification. The mapping data therefore indicate that the PEG moiety is specifically attached to this peptide and not to any of the other peptides that were screened. The second potential site of attachment, the amino-terminus is on a peptide that is only three amino acids long and is not detected in the peptide map. It is inferred that additional PEG attachments are at this site. Consistent with this notion, a small percentage of the rat mutated neublastin N95K is not truncated and contains the mature Ala-1 sequence. This peptide elutes at 30 μm and is visible in the peptide map from the non-PEGylated digest, but is absent from the PEGylated mutated neublastin NBN106-N95K digests.

Example 3

Assessing the Potency of Internally PEGylated Mutated Neublastin NBN106-N95K in a Kinase Receptor Activation (KIRA) ELISA The potency of PEGylated mutated rat neublastin was measured using neublastin dependent activation/phosphorylation of c-Ret as a reporter for neublastin activity in an ELISA that was specific for the presence of phosphorylated RET. NB41A3-mRL3 cells, an adherent murine neuroblastoma mAb (AA.GE7.3) in 50 mM carbonate buffer, pH 9.6 at 4° C. for 18 h, and blocked at room temperature for one hour with block buffer (20 mM Tris HCl pH 7.5, 150 mM NaCl, 0.1% Tween-20 (TBST) containing 1% normal mouse serum and 3% bovine serum albumin).

After a 2 h incubation at room temperature, the wells were washed 6-times with TBST. Phosphorylated Ret was detected by incubating the wells at room temperature for 2 h with 2 μg/mL of horseradish peroxidase (HRP)-conjugated anti-phosphotyrosine 4G10 antibody in block buffer, washing 6-times with TBST, and measuring HRP activity at 450 nm with a colorometric detection reagent. The absorbance values from wells treated with lysate or with lysis buffer were measured and the background corrected signal was plotted as a function of the concentration of neublastin present in the activation mixture. The potency of PEGylated mutated neublastin (3,(4)×10 kDa PEG NBN106-N95K) in the KIRA ELISA was indistinguishable from that of the wild-type NBN113 material (Table 8). There was no effect of two freeze-thaw cycles on potency and following this treatment there was no significant increase in the turbidity of the sample, indicating that the samples can be safely thawed for the study. In independent studies accessing the activity of product with three and four 10 kDa PEGs per molecule separately, it was determined that the adduct with three PEGs was fully active, while the four PEG product had reduced potency (Table 8). These data demonstrate that 3,(4)×10 kDa PEG NBN106-N95K and 3×10 kDa PEG NBN106-N95K is activate Ret to a similar extent and with the same dose-dependence as non-mutated (wild-type) neublastin, NBN113. However, although 4×10 kDa PEG NBN106-N95K activates Ret to a similar extent as non-mutated (wild-type) NBN113, 4×10 kDa PEG NBN106-N95K is approximately 10-fold less potent than non-mutated (wild-type) NBN113 in activating Ret. Estimated EC50's are provided in Table 8.

Example 4

Pharmokinetic Studies of Internally PEGylated Mutated Rat Neublastin NBN106-N95K in Rats and Mice The pharmokinetic properties of various PEGylated and non-PEGylated mutated neublastin products in rat and mouse models were examined (see Table 8 for summary of results).

The data revealed that PEGylation of rat mutated neublastin NBN1 06-N95K with 3.3, 10000 Da PEGs resulted in a significant effect on the half life and bioavailability of the neublastin. Following a 1 mg/kg IV administration in Sprague Dawley rats, peak levels of PEGylated mutated neublastin of 3000 ng/mL were detected after 7 minutes, and levels of 700 ng/mL were detected after 24 h, 200 ng/mL after 48 h, and 100 ng/mL after 72 h. In contrast for non-PEGylated mutated neublastin N95K following a 1 mg/kg IV administration, levels of 1500 ng/mL were detected after 7 minutes, but then the levels quickly dropped to 70 ng/mL after 3 h and were not detectable after 7 h. The effects of PEGylation were even more pronounced in animals treated with PEGylated neublastin by subcutaneous administration.

Following a 1 mg/kg s.c. administration, circulating levels of PEGylated neublastin reached a maximum of 200 ng/mL after 24 h and remained at this level for the duration of the three day study. In contrast, no detectable neublastin was observed at any time point following administration of non-PEGylated mutated neublastin.

The analysis of the PEGylated N95K samples are complicated by the presence of adducts comprising 2, 3 and 4 PEGs per molecule, which each will display a different PK profile. In early PK studies, mice were used to facilitate screening through a variety of candidates and routes of administration. The mouse studies revealed dramatic differences in the bioavailability of the candidates. However, when the 3.3 10 kDa PEG adduct was evaluated in rats, it was found to be less bioavailable in rats than it was in mice. This difference in bioavailability was particularly pronounced following i.p. administration. Levels in mice reached 1600 ng/mL after 7 hr and remained at 400 ng/mL after 24 hr. In contrast, rat levels were constant at 100 ng/mL for 4-48 hr.

Two surprising and unexpected results emerged from the PK studies summarized in Table 8: 1) PEGylation of the amino-terminal amino acids of non-glycosylated neublastin was not sufficient to increase serum exposure substantially; and 2) PEGylation of the amino-terminal amino acid(s) of neublastin together with modification (e.g. PEGylation or glycosylation) of amino acid 95 was sufficient to increase serum exposure substantially. For example, glycosylated NBN104 (CHO) gave no detectable exposure after s.c. administration; however, glycosylated 1×20 kDa PEG NBN104 (CHO) gave high serum exposure after s.c. administration. Similarly, 2×20 kDa PEG NBN113 gave low-to-moderate serum exposure after s.c. administration; however, glycosylated 2×20 kDa PEG NBN104 (CHO) gave high serum exposure after s.c. administration. These results indicated that polymer conjugation of the amino-terminal amino acid(s) of neublastin together with either polymer conjugation of an internal amino acid (e.g. at position 95) or glycosylation at an internal amino acid (e.g. at position 95) results in substantially increased serum exposure after systemic administration.

Both wild-type rat neublastin and mutated neublastin N95K were refolded and purified to >95% for efficacy tests in the STZ diabetic rat neuropathy model. Wild-type neublastin was formulated to go directly into animal testing while N95K was prepared for PEGylation with 10 kDa PEG-SPA. To accomplish the refolding and purification goal, a refolding method utilizing size exclusion chromatography (SEC) was developed that permitted the renaturation of neublastin from E. coli inclusion bodies in large quantities and at high concentrations. In addition to SEC, both Ni-NTA and CM silica column chromatography steps were employed to increase the final protein purity. The proteins were subjected to extensive characterization including analysis by SDS-PAGE, size exclusion chromatography, ESMS, assessment of activity by KIRA ELISA, and determination of endotoxin content. SDS-PAGE and SEC of the final protein products indicated a purity of greater than 95%. The endotoxin level of each product was <0.2 EU/mg. The specific activity of both proteins in the KIRA ELISA is approximately 10 nM. Wild-type neublastin was formulated at 1.0 mg/ml and N95K was formulated at 2.6 mg/ml in phosphate-buffered saline (PBS) pH6.5. Wild-type neublastin was aliquoted into 15 ml tubes and stored frozen at −70° C. while N95K was subjected to PEGylation prior to aliquoting and freezing.

Example 5

Refolding and Purification of a Wild-Type Neublastin and the Mutated N95K Neublastin Both neublastin forms were expressed in E. coli as Histidine (His)-tagged fusion proteins with an enterokinase cleavage site immediately adjacent to the start of the mature 113 amino acid sequence. Bacteria expressing either wild-type (1.8 kg pellet) or N95K (2.5 kg pellet) neublastin were subjected to lysis in 2 liters of PBS using a APV Gaulin Press. Following centrifugation (10,000 rpm) to pellet the inclusion bodies, the supernatants from each preparation were discarded. The inclusion body pellets were washed two times with wash buffer (0.02M Tris-HCl pH 8.5, 0.5 mM EDTA) then washed two times with the same buffer containing Triton X-100 (2%, v/v) followed by two additional buffer washes without detergent. Both pellets were solubilized using 6M guanidine hydrochloride, 0.1M Tris pH 8.5, 0.1M DTT, and 1 mM EDTA. To aid in the solubilization process, each pellet was subjected to homogenization using a polytron homogenizer followed by overnight stirring at room temperature. The solubilized proteins were clarified by centrifugation prior to denaturing chromatography through Superdex 200 (5.5 liter column equilibrated with 0.05M glycine/$H_3PO_4$ pH 3.0 with 2M Guanidine-HCl) at 20 ml per minute.

Denatured neublastin was identified by SDS-PAGE. Fractions containing either wild type-neublastin or N95K were pooled and concentrated to approximately 250 mL using an Amicon 2.5-liter stirred cell concentrator. After filtration to remove any precipitate, the concentrated protein was subjected to renaturing sizing chromatography through Superdex 200 equilibrated with 0.1 M Tris-HCl pH 7.8, 0.5M guanidine-HCl, 8.8 mM reduced glutathione and 0.22 mM oxidized glutathione. The column was developed using 0.5M guanidine-HCl at 20 mL per minute. Fractions containing renatured wild-type neublastin or N95K neublastin were identified by SDS-PAGE, pooled, and stored at 4° C. until needed for His tag removal.

Alternative Method of Refolding Wild-Type Neublastin and Mutated N95K Neublastin by Dilution.

To refold neublastin by dilution, solubilzed protein was rapidly diluted in refolding buffer (0.5 M guanidine-HCl, 0.35 M L-Arginine, 50 mM potassium phosphate (pH 7.8), 0.2 mM glutathione reduced, 1 mM glutathione oxidized, and 0.1% Tween-80) at a final concentration of 0.1 mg/ml and incubated at room temperature for 48 hours without stirring. Refolded neublastin was then concentrated 25 fold, brought to 40 mM imidazole, and applied to a chromatography column containing Ni-NTA agarose to further concentrate the product and eliminate host cell proteins. The column was washed with 10 times column volume with wash buffer (40 mM imidazole, 0.5 M guanidine-HCl). Neublastin was then eluted from the resin with 0.2 M Imidazole and 0.5 M guanidine-HCl.

Concentration of Column-Refolded Neublastin by Ni-NTA Chromatography.

Column-renatured neublastin was stored at 4° C. for at least 24 hours before proceeding with the purification to promote disulfide formation between the neublastin monomers. During this time, a precipitate formed and was removed by filtration through a 0.2µ polyether sulfone (PES) filter unit. To decrease non-specific binding, the protein solution was brought to 20 mM imidazole prior to loading on a 100 ml Ni-NTA (Qiagen) column equilibrated with column buffer (0.5 M guanidine and 20 mM imidazole) at 50 ml per minute. Following the protein application, the column was washed to baseline using the same buffer. Neublastin was eluted from the resin using approximately 300 mL of elution buffer containing 0.5 M guanidine-HCl and 0.4 M imidazole. After elution, neublastin was dialyzed overnight (using 10 kDa dialysis tubing) at room temperature against ten volumes of 5 mM HCl. Dialysis promotes the hydrolysis of contaminating substances and decreases the guanidine-HCl and imidazole concentrations to 0.05M and 0.04M, respectively.

Cleavage of the His Tag by Lysyl Endopeptidase or Enterokinase.

The next day, any precipitate that formed during dialysis was removed by filtration. The following purification steps apply to both the column- and dilution-refolded neublastin products. The protein sample was made to 0.1 M NaCl by the addition of NaCl from a 5M stock for a final salt concentration including the remaining guanidine-HCl of approximately 150 mM. This concentration was confirmed using a conductivity meter. Additionally, 1 M HEPES pH 7.8 was added for a final concentration of 25 mM. To cleave the His tag, lysyl endopeptidase was added to the wild-type neublastin and enterokinase was added to the N95K mutated neublastin, both at an approximately 1:300 ratio of protease to neublastin. Enterokinase was used in place of lysyl endopeptidase for the N95K mutated neublastin due to an additional protease cleavage site in the mutated protein at Lys95. The samples were stirred at room temperature for 2 hours and the digestions monitored by SDS-PAGE.

His Tag Removal by Ni-NTA Chromatography.

Protease-treated neublastin was applied to a 100 mL Ni-NTA column equilibrated with 0.5M guanidine-HCl and 20 mM imidazole at 50 mL per minute. The column was washed to baseline with the same buffer. Any protein washing off the column was pooled with the flow-through protein containing neublastin without the His tag.

CM Silica Chromatography.

Following Ni-NTA chromatography, the protein was immediately subjected to further purification through CM silica resin. A 20 mL CM silica column equilibrated with loading buffer (5 mM phosphate pH 6.5, 150 mM NaCl) was loaded with neublastin at 20 mL per minute. The column was washed with twenty column volumes of wash buffer (5 mM phosphate pH 6.5, 400 mM NaCl) and the protein step eluted with elution buffer containing 5 mM phosphate pH 6.5 but with 1 M NaCl. The eluted protein was dialyzed overnight against the phosphate alone to bring the salt concentration down to 100 mM for N95K and 150 mM for wild type neublastin. Both samples were filtered through a 0.2µ PES filter unit, analyzed by SDS-PAGE, and stored at 4° C. until needed for further characterizations and/or PEGylation.

Wild-type and N95K mutated neublastin protein preparations were subjected to UV spectrum analysis to assess their absorbance at 280. Using a micro quartz cuvette and blanking against buffer alone, 100 µl of either wild-type or N95K mutated neublastin was continuously scanned from 230 to 330 nm using a Beckman spectrophotometer. Based on this analysis, wild-type neublastin was determined to be at a concentration of 1.1 mg/ml and N95K mutated neublastin at 2.6 mg/ml (A280 nm-$E^{0.1\%}$=0.5 used for each protein). Less than 1% precipitated material was identified based on absorbance at 330 nm.

To assess the purity of both protein preparations, each sample (0.5 mg) was subjected to size exclusion chromatography through a 16/30 Superdex 75 column. The column was equilibrated with 5 mM phosphate pH 6.5 containing 400 mM NaCl and developed with a 1.5 mL per minute flow rate. Based on the absorbance at 280 nm, both wild-type and N95K mutated neublastin preparations migrated as a single peak with an expected molecular weight (23-24 kDa), and they did not contain any significant protein contamination.

Both wild-type and N95K mutated neublastin proteins were reduced in 2.5 M guanidine-HCl, 60 mM Tris pH 8.0 and 16 mM DTT. The reduced samples were desalted over a short $C_4$ column and analyzed on-line by ESMS using a triple quadrupole instrument. The ESMS raw data were deconvoluted by the MaxEnt program to generate mass spectra. This procedure allows multiple charged signals to collapse into one peak that directly corresponds to the molecular mass in kilodaltons (kDa). The deconvoluted mass spectrum for wild-type showed the predominant species is 12046 Da, which is in agreement with the predicted molecular weight of 12046.7 Da for the 113 amino acid form of the protein. A minor component was also observed (12063 Da) suggesting the presence of an oxidation product. Three peaks were identified in the N95K mutated neublastin protein sample. The major component demonstrated an apparent molecular mass of 11345 Da in agreement with the predicted mass for the 106 amino acid form of the protein. The other two peaks had masses of 11362 and 12061 Da, suggesting N95K oxidation and the presence of the 113 amino acid form, respectively.

The presence of the 106 and 113 amino acid forms in the N95K mutated neublastin protein preparation is attributable to digestion with enterokinase. This protease from Biozyme is a natural enzyme preparation purified from calf intestinal mucosa and is reported to contain a slight trypsin contamination (0.25 ng trypsin per µg enterokinase). Therefore, trypsin may be acting on the N95K mutated neublastin protein on the carboxy terminal side of Arg7 to produce the predominant 106 amino acid form. On the other hand, lysyl endopeptidase used to cleave wild-type neublastin is a single protease activity acting on the carboxy terminal side of the lysine residue contained within the His tag to produce the mature 113 amino acid neublastin form. Both the 106 and 113 amino acid forms of neublastin are equally active in all assays tested and behave similarly in guanidine-HCl stability tests.

Neublastin activity was determined by its ability to stimulate c-Ret phosphorylation in NB41A3-mRL3 cells using the KIRA ELISA described in Example 3. Phosphorylated Ret was detected by incubating (2 hours) the captured receptor with HRP-conjugated phosphotyrosine antibody (4G10; 0.2 µg per well). Following the incubation, the wells were washed six times with TBST, and the HRP activity detected at 450 nm with a colorimetric assay. The absorbance values from wells treated with lysate or with lysis buffer alone were measured, background corrected, and the data plotted as a function of the concentration of neublastin present in the activation mixture. The data demonstrate that the purified neublastin polypeptides resulted in the appearance of phosphorylated RET, indicating that the purified neublastin was active in this assay.

Example 6

Preparation of a Serum Albumin-Neublastin Conjugate

Wild-type rat neublastin at a concentration of 1 mg/ml in PBS was treated with 1 mM sulfo-SMCC (Pierce) and desalted to remove excess cross-linker. Since the wild-type neublastin protein contains only a single amine at its amino-terminus and no free sulfhydryl groups, reaction with SMCC was expected to result in site-specific modification of the neublastin with SMCC attached at its amino-terminus.

Next, 60 µg of the neublastin-SMCC conjugate was incubated with 120 µg of bovine serum albumin and analyzed for extent of cross-linking by SDS-PAGE. BSA contains a single free SH group and consequently reaction with the neublastin-SMCC conjugate is expected to result in modification at this site through the maleimide on the SMCC. Under these conditions, two additional bands of higher molecular weight were observed, which are consistent in mass with modification of the neublastin with a single BSA moiety and with two BSA molecules since each neublastin molecule contains two amino-termini that can undergo reaction, and consequently are in agreement with this notion. Concurrent with the formation of these bands, was a decrease in the intensity of the neublastin-SMCC and BSA bands. Based on the intensity of the remaining neublastin band, the reaction appeared to have gone to 70-80% completion.

The monosubstituted product was purified from the reaction mixture by subjecting the material to cation exchange chromatography and size exclusion chromatography on a Superdex 200 column (Pharmacia) essentially as described for PEGylation studies discussed above. Column fractions from the gel filtration run were analyzed by SDS-PAGE and those containing the monosubstituted product were analyzed for protein content by absorbance at 280 nm. Since the mass of BSA is approximately twice that of neublastin, the apparent concentration was divided by a factor of 3 to give the neublastin equivalent. This fraction was subjected this to analysis for function in the KIRA ELISA. IC50 values for both the wt- and BSA-conjugated neublastin were 3-6 nM, indicating that conjugation to the BSA had not compromised function.

While these preliminary studies were generated with BSA, the corresponding serum albumin proteins from rats and humans also contain a free SH. Consequently a similar approach can be applied to generate a rat serum albumin-rat neublastin conjugate for performing PK and efficacy studies in rats and human serum albumin-human neublastin for performing clinical trials. Similarly SMCC can be substituted with any of a number of cross-linkers that contain an amino reactive group on one side and a thiol reactive group on the other side. Examples of amine reactive cross-linkers that insert a thiol reactive-maleimide are AMAS, BMPS, MBS, EMCS, SMPB, SMPH, KMUS, or GMBS, that insert a thiol reactive-haloacetate group are SBAP, SIA, SIAB and that provide a protected or non protected thiol for reaction with sulfhydryl groups to product a reducible linkage are SPDP, SMPT, SATA, or SATP all of which are available from Pierce. Such cross linkers are merely exemplary and many alternative strategies are anticipated for linking the amino-terminus of neublastin with serum albumin. A skilled artisan also could generate conjugates to serum albumin that are not targeted at the amino-terminus of neublastin or at the thiol moiety on serum albumin. Neublastin-serum albumin fusions created using genetic engineering where neublastin is fused to the serum albumin gene at its amino-terminus, carboxy-terminus, or at both ends, are also expected to be functional.

This method can be extended through routine adaptations to any neublastin-serum albumin conjugate that would result in a product with a prolonged half-life in animals and consequently in humans.

Example 7

Crystallization and Structure Determination of Human Neublastin

Selenomethionine labeled neublastin was expressed using a standard procedure to inhibit methionine biosynthesis (Van Duyne, et al., 1991, *Science* 252, 839-842). Both wildtype neublastin and selenomethionine-incorporated neublastin was concentrated to 17 mg/ml in 0.8 M arginine. The protein stock was concentrated to 17 mg/ml in 0.8 M arginine. Crystals were grown by the hanging-drop vapor diffusion method (Jancarik, J. & Kim, S. H., 1991, *J. Appl. Crystallogr.* 24, 409-411) out of 1.25 M magnesium sulfate, 0.1 M MES pH 6.5 at 20° C. The most reproducible crystals were obtained by microseeding. The crystals were cryoprotected by the addition of 5% ethylene glycol every 60 seconds to a final concentration of 1.25 M magnesium sulfate, 0.1 M MES pH 6.5, and 30% (v/v) ethylene glycol and then frozen by quick transfer into liquid nitrogen.

Crystals approximately 100 microns on each side diffracted to 1.6A at beamline X4A at the National Synchrotron Light Source (Upton, N.Y.). Data processing with the HKL program package (Otwinowski (1993) in: Proceeding of the CCP4 Study Weekend: Data Collection and Processing (Sawer et al., Eds.) pp. 56-62, Daresbury Laboratory, Warrington) revealed the crystals to belong to a C2 space group with 1 covalent dimer per asymmetric unit and approximate cell dimensions a=115 Å, b=33 Å, c=55 Å and $\alpha=\gamma=90°$, $\beta=99°$.

The crystal structure was solved by multiple isomorphous replacements. Native neublastin crystals were soaked in 1 mM $PtCl_4$ for 4 hours, 10 mM $IrCl_3$ for 72 hours, and 10 mM $IrCl_6$ for 18 hours and data collected and processed by the HKL suite (Otwinowski et al., supra). The two selenomethionine sites were located by inspection of isomorphous and anomalous difference pattersons. The remaining sites were located using SOLVE (4). The phases were improved by RESOLVE (Terwilliger et al., 1999, *Acta Crystallogr. D.* 55, 849-861) to a figure of merit of 0.56 and resulting maps were of sufficient quality to trace the neublastin model. Alternating cycles of model building with O2D (5 G J Kleywegt & T A Jones, "O2D—the manual", software manual, Uppsala, 1994) and refinement with CNX using a mlhl target and refined against the selenomethionine data resulted in a complete model of the neublastin protein, excluding the first amino-terminal 13 amino acids, as well as 89 water molecules and 6 sulfate anions. The final $R_{free}$ is 28.5% and R-factor is 24.7% to 2.0 Å with good stereochemistry.

Example 8

Sulfate Binding Sites and Modeling of Heparin Sulfate

A cluster of three sulfates at the vertices of an approximate equilateral triangle are located on at the pre-helix region of the neublastin surface and could represent a binding site for heparin sulfate. There are three arginine residues that appear to have key interactions with these sulfates. The arginine residue R48 links together all three sulfates (#2, #6, and #3). Its backbone amide interacts with sulfate #2, while its side chain guanidinium group forms a bifurcated hydrogen bond with sulfates #6 and #3. A second arginine residue (R49) forms a hydrogen bond with sulfate #2 and a third arginine residue (R51) forms a long hydrogen bond to sulfate #6.

These sulfates may represent binding pockets for heparin sulfate, which if mutated to non-positively charged residues could reduce heparin sulfate binding and possibly decrease and/or delay clearance of the neublastin molecule upon in vivo administration. A model of heparin sulfate bound to neublastin may be constructed by superimposing the sulfates of the glycosaminoglycan with the existing sulfates of the neublastin crystal structure. The n and n+2 saccharide-linked sulfates in heparin sulfate from the crystal structure of FGF-1 complexed to heparin sulfate are separated by approximately 8.5 Å (Pellegrini et al., (2000) *Nature* 407, 1029-1034). This measurement closely matches the distance between sulfates of the 3-sulfate cluster in the neublastin structure; sulfates #3 and #6 are separated by 8.8 Å and sulfates #3 and #2 are separated by 8.1 Å. This distance measurement correspondance could indicate that this R48/R49/R51 motif is part of a heparin binding site. This suggests that single site mutations of R48, R49 or R51 to glutamate or aspartate, or any other non-positive amino acid, might reduce heparin sulfate binding affinity without reducing the receptor-binding activity of neublastin, thereby resulting in a biologically active product that has a prolonged half-life in animals and consequently in humans. To test this possibility, we are generating a series of constructs that contain one or more arginines mutated to glutamic acids. The mutated neublastin products will be expressed in *E. coli*, purified and refolded, and tested for function. Finally, the products will be tested for ability to bind heparin and for pharmacokinetics and pharmacodynamics in animals.

One or more of these sites might also provide other sites for PEGylation which can be accomplished by replacing R with K or C and applying the methods described above.

Example 9

Dosage of Pegylated Mutated Neublastin NBN106-N95K on Reversal of Tactile and Thermal Hyperalgesia in Nerve Ligation Animal Model of Neuropathic Pain We had previously demonstrated that 1 mg/kg wild-type neublastin, administered s.c. 3 times per week, results in nearly complete reversal and normalization of neuropathic pain behaviors (tactile allodynia and thermal hyperalgesia) induced by spinal nerve ligation in the rat, whereas 0.03 mg/kg wild-type neublastin, administered s.c. 3 times per week had no effect and 0.1 mg/kg and 0.6 mg/kg wild-type neublastin, administered s.c. 3 times per week had intermediate effects in this model.

Here, we describe studies to address the reversal effect of pegylated N95K neublastin on tactile allodynia and thermal hyperalgesia in the Chung L5/L6 spinal nerve ligation ("SNL") model. Sprague-Dawley male rats (230-380 g) were divided into two groups. All rats received the spinal nerve ligation. One group of rats (n=6) was administered vehicle by subcutaneous injection. A second group of rats (n=6 per group) were administered pegylated N95K neublastin (3,(4)× 10 kDa PEG NBN106-N95K) by subcutaneous injection at 10 µg/kg. 3(,4)×10 kDa PEG NBN106-N95K, comprised neublastin protein that was *E. coli*-derived and contained an Asn-to-Lys amino acid substitution at position 95, then truncated (amino-terminus truncation of 7 amino acids; NBN106), and finally pegylated with an average of 3.3 PEG moieties per dimer of NBN, using methoxylpoly(ethylene glycol)-succinimidyl propionate (SPA-PEG) with a molecular mass of 10,000 Da as the reactant. The vehicle consisted of 5 mM phosphate and 150 mM sodium chloride at pH 6.5. Subcutaneous injections were administered on days 3, 5, 7, 10, 12 and 14 following the operation (post-SNL). The Von Frey (Chaplan et al. (1994), *J. Neurosci. Meth.* 53: 55-63) and Hargreave's (Hargreaves et al. (1988), *Pain* 32: 77-88) behavioral tests were used to monitor tactile and thermal responses, respectively. These pain responses were monitored prior to the spinal nerve ligation to establish baseline responses, on day 2 post-SNL to verify the presence of tactile and thermal hyperalgesia, and then on days 3, 5, 7, 10, 12, 14 and 15 post-SNL. To assess statistical significance of drug treatment relative to vehicle treatment, a 1-way analysis of variance (1-way ANOVA) was carried out followed by a post-hoc Student Neuman Keuls (SNK) test.

Both types of neuropathic pain behavior (tactile allodynia and thermal hyperalgesia) developed fully by day 2 post-SNL, as expected. Subcutaneous administration of 10 µg/kg 3(,4)×10 kDa PEG N95K-NBN106 led to substantial and statistically significant reversal of both types of neuropathic pain in rats with spinal nerve ligation. In rats with spinal nerve ligation, the effect of 10 µg/kg 3(,4)×10 kDa PEG NBN106-N95K on thermal sensitivity and tactile allodynia first became statistically significant 4 days after the initiation of administration of pegylated N95K neublastin. The effect of 10 µg/kg 3(,4)×10 kDa PEG NBN106-N95K on thermal sensitivity and tactile allodynia reached a plateau approximately 4 days after the initiation of administration of pegylated N95K neublastin. The effects of 3(,4)×10 kDa PEG NBN106-N95K did not diminish during the 2 to 3 day interval between administrations. In fact, there was substantial normalization of pain behaviors between the administrations of pegylated N95K neublastin on days 5 and 7. In another experiment (data not shown), subcutaneous administration of 3 µg/kg 3(,4)×10 kDa PEG NBN106-N95K on days 3, 5, 7, 10, 12 and 14 led to a significant normalization of pain behaviors (tactile and thermal hyperalgesia) in the SNL model, though the onset of the effect was somewhat slower.

These results demonstrated that of 3(,4)×10 kDa PEG NBN106-N95K has an increased potency of at least 100 to 333-fold over non-mutated non-glycosylated neublastin on tactile allodynia and thermal hyperalgesia pain behaviors in the SNL model. The enhanced pharmacokinetic properties of 3(,4)×10 kDa PEG N95K NBN106 compared to non-mutated non-glycosylated neublastin indicated that efficacy of systemically administered neublastin correlates with serum levels of neublastin. These results demonstrated that polymer conjugates of mutated neublastin can be used to treat neuropathic pain in patients with greatly reduced doses, and potentially reduced dosing frequency, due to their enhanced bioavailability compared to unconjugated neublastin.

TABLE 8

Biological Characterization of PEGylated NBN

| Form of NBN | PEGylated Amino Acids | Glycosylated Amino Acid | Exposure in Mice After s.c. Administration | KIRA: ~EC50 | KIRA: ~Max Efficacy vs WT |
|---|---|---|---|---|---|
| NBN | | | nd | 0.4-1.2 nM | 100% |
| NBN104 (CHO) | | 95, 95 | nd | 0.7 nM | 90% |
| 2 × 5 kDa PEG-NBN | 1, 1 | | nd | 0.2 nM | 105% |
| 4 × 5 kDa PEG NBN106-N95K | 1, 1, 95, 95 | | nd | 1 nM | 80% |
| 2 × 10 kDa PEG-NBN | 1, 1 | | nd | 0.2 nM | 72% |
| 1 × 20 kDa Branched PEG-NBN | 1 | | nd | 0.2 nM | 83% |
| 1 × 20 kDa PEG-NBN104 (CHO) | 1 | 95, 95 | ++ | 0.3 nM | 110% |
| 3 × 10 kDa PEG-WT/N95K-NBN106 | 1, 1, 95 | | ++ | 0.7 nM | 115% |
| 3 × 10 kDa PEG NBN106-N95K | 1, 1, 95 | | ++ | 0.8 nM | 100% |
| 3 (,4) × 10 kDa PEG NBN106-N95K | 1, 1, 95 (,95) | | ++ | 1.6 nM | 90% |
| 4 × 10 kDa PEG NBN106-N95K | 1, 1, 95, 95 | | ++ | 11 nM | >80% |
| 2 × 20 kDa PEG-NBN | 1, 1 | | + | 0.6 nM | 80% |
| 2 × 20 kDa Branched PEG NBN106-N95K | 1, 95 | | ++ | inactive | inactive |
| 2 × 20 kDa PEG-NBN104 (CHO) | 1, 1 | 95, 95 | ++ | 1 nM | 105% |

Note:
nd denotes not detectable,
+ indicates low-moderate exposure,
++ indicates high exposure
Note:
all are NBN113, unless otherwise indicated
Note:
all are *E. coli* derived, unless CHO is indicated

| SEQ ID NO: | Sequence: |
|---|---|
| 1 | Consensus mature neublastin polypeptide - 113 aa |
| 2 | Human mature NBN113 |
| 3 | Mouse mature NBN113 |
| 4 | Rat mature NBN113 |
| 5 | PreproNBN - 220 aa |
| 6 | Mature NBN140 |
| 7 | Mature NBN116 |
| 8 | Truncated NBN112 |
| 9 | Truncated NBN111 |
| 10 | Truncated NBN110 |
| 11 | Truncated NBN109 |
| 12 | Truncated NBN108 |
| 13 | Truncated NBN107 |
| 14 | Truncated NBN106 |
| 15 | Truncated NBN105 |
| 16 | Truncated NBN104 |
| 17 | Truncated NBN103 |
| 18 | Truncated NBN102 |
| 19 | Truncated NBN101 |
| 20 | Truncated NBN100 |
| 21 | Truncated NBN99 |
| 22 | Polypeptide DYKDDDD - 8 aa |
| 23 | NBN113-N95K |
| 24 | NBN106-N95K |
| 25 | Rat wild-type ORF - 675 nt |
| 26 | Rat wild-type preproNBN polypeptide - 224 aa |
| 27 | KD2-310 Primer |
| 28 | KD2-311 Primer |
| 29 | KD3-254 Primer |
| 30 | KD2-255 Primer |
| 31 | KD3-258 Primer |
| 32 | KD3-259 Primer |
| 33 | KD3-256 Primer |
| 34 | KD3-257 Primer |
| 35 | His-tagged NBN ORF - 414 nt |
| 36 | His-tagged NBN - 135 aa |

Other Embodiments

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims.

What is claimed is:

1. An isolated polypeptide comprising an amino acid sequence at least 90% identical to amino acids 8-113 of SEQ ID NO:1, wherein the polypeptide includes at least one amino acid substitution selected from the group consisting of:
   (a) an amino acid other than arginine at the position corresponding to position 14 in SEQ ID NO:1;
   (b) an amino acid other than arginine at the position corresponding to position 39 in SEQ ID NO:1;
   (c) an amino acid other than arginine at the position corresponding to position 68 in SEQ ID NO:1; and
   (d) an amino acid other than asparagine at the position corresponding to position 95 in SEQ ID NO:1,
   wherein the polypeptide, when dimerized, binds to GFRα3.

2. The polypeptide of claim 1, wherein the amino acid at the position corresponding to position 95 in SEQ ID NO:1 is an amino acid other than asparagine.

3. The polypeptide of claim 1, wherein the amino acid at the position corresponding to position 95 in SEQ ID NO:1 is lysine.

4. The polypeptide of claim 1, wherein the polypeptide comprises amino acids 8-113 of SEQ ID NO:2, SEQ ID NO:3, or SEQ ID NO:4, wherein an amino acid other than asparagine is substituted for the asparagine at position 95.

5. The polypeptide of claim 1, wherein the polypeptide comprises amino acids 1-113 of SEQ ID NO:2, SEQ ID NO:3 or SEQ ID NO:4, wherein lysine is substituted for asparagine at position 95.

6. The polypeptide of claim 1, wherein the amino acid sequence is at least 95% identical to amino acids 8-113 of SEQ ID NO:1.

7. The polypeptide of claim 1, wherein the amino acid sequence is at least 95% identical to amino acids 8-113 of SEQ ID NO:2.

8. The polypeptide of claim 2, wherein the amino acid sequence is at least 95% identical to amino acids 8-113 of SEQ ID NO:2.

9. The polypeptide of claim 3, wherein the amino acid sequence is at least 95% identical to amino acids 8-113 of SEQ ID NO:2.

10. A fusion protein comprising the polypeptide of claim 1 fused to a second moiety.

11. The fusion protein of claim 10, wherein the second moiety is a human serum albumin sequence.

12. A dimer comprising two polypeptides according to claim 1.

13. A dimer comprising two fusion proteins according to claim 10.

14. A conjugate comprising the polypeptide of claim 1 conjugated to a non-naturally occurring polymer.

15. A conjugate comprising the polypeptide of claim 7 conjugated to a non-naturally occurring polymer.

16. A conjugate comprising the polypeptide of claim 8 conjugated to a non-naturally occurring polymer.

17. A conjugate comprising the polypeptide of claim 9 conjugated to a non-naturally occurring polymer.

18. A conjugate comprising the fusion protein of claim 10 conjugated to a non-naturally occurring polymer.

19. The conjugate of claim 14, wherein the polymer is a polyalkylene glycol.

20. The conjugate of claim 19, wherein the polyalkylene glycol is polyethylene glycol.

21. The conjugate of claim 15, wherein the polymer is a polyalkylene glycol.

22. The conjugate of claim 21, wherein the polyalkylene glycol is polyethylene glycol.

23. The conjugate of claim 16, wherein the polymer is a polyalkylene glycol.

24. The conjugate of claim 23, wherein the polyalkylene glycol is polyethylene glycol.

25. The conjugate of claim 17, wherein the polymer is a polyalkylene glycol.

26. The conjugate of claim 25, wherein the polyalkylene glycol is polyethylene glycol.

27. The conjugate of claim 19, wherein the polyalkylene glycol is conjugated to a lysine residue substituted at a position corresponding to position 14, 39, 68, or 95 in SEQ ID NO:1.

28. The conjugate of claim 19, wherein the polyalkylene glycol is conjugated to the N terminus of the polypeptide.

29. The conjugate of claim 19, wherein the polypeptide is glycosylated.

30. A pharmaceutical composition comprising the polypeptide of claim 1 and physiologically acceptable vehicle.

31. A pharmaceutical composition comprising the fusion protein of claim 10 and physiologically acceptable vehicle.

32. A pharmaceutical composition comprising the conjugate of claim 19 and physiologically acceptable vehicle.

33. A polypeptide comprising an amino acid sequence at least 95% identical to amino acids 15-113 of SEQ ID NO:2 (NBN99), wherein the polypeptide includes at least one amino acid substitution selected from the group consisting of:
   (a) an amino acid other than arginine at the position corresponding to position 39 in SEQ ID NO:2;
   (b) an amino acid other than arginine at the position corresponding to position 68 in SEQ ID NO:2; and
   (c) an amino acid other than asparagine at the position corresponding to position 95 in SEQ ID NO:2,
   wherein the polypeptide, when dimerized, binds to GFRα3.

34. The polypeptide of claim 33, wherein the amino acid at the position corresponding to position 39 in SEQ ID NO:2 is an amino acid other than arginine.

35. The polypeptide of claim 33, wherein the amino acid at the position corresponding to position 39 in SEQ ID NO:2 is lysine.

36. The polypeptide of claim 33, wherein the amino acid at the position corresponding to position 68 in SEQ ID NO:2 is an amino acid other than arginine.

37. The polypeptide of claim 33, wherein the amino acid at the position corresponding to position 68 in SEQ ID NO:2 is lysine.

38. The polypeptide of claim 33, wherein the amino acid at the position corresponding to position 95 in SEQ ID NO:2 is an amino acid other than asparagine.

39. The polypeptide of claim 33, wherein the amino acid at the position corresponding to position 95 in SEQ ID NO:2 is lysine.

40. The polypeptide of claim 33, wherein the polypeptide comprises amino acids 15-113 of SEQ ID NO:2 (NBN99), wherein an amino acid other than asparagine is substituted for the asparagine at position 95.

41. The polypeptide of claim 33, wherein the polypeptide comprises amino acids 15-113 of SEQ ID NO:2 (NBN99), wherein lysine is substituted for asparagine at position 95.

42. A conjugate comprising the polypeptide of claim 33 conjugated to a non-naturally occurring polymer.

43. A conjugate comprising the polypeptide of claim 34 conjugated to a non-naturally occurring polymer.

44. A conjugate comprising the polypeptide of claim 35 conjugated to a non-naturally occurring polymer.

45. A conjugate comprising the polypeptide of claim 36 conjugated to a non-naturally occurring polymer.

46. A conjugate comprising the polypeptide of claim 37 conjugated to a non-naturally occurring polymer.

47. A conjugate comprising the polypeptide of claim 38 conjugated to a non-naturally occurring polymer.

48. A conjugate comprising the polypeptide of claim 39 conjugated to a non-naturally occurring polymer.

49. A conjugate comprising the polypeptide of claim 40 conjugated to a non-naturally occurring polymer.

50. A conjugate comprising the polypeptide of claim 41 conjugated to a non-naturally occurring polymer.

51. The conjugate of claim 42, wherein the polymer is a polyalkylene glycol.

52. The conjugate of claim 51, wherein the polyalkylene glycol is polyethylene glycol.

53. The conjugate of claim 43, wherein the polymer is a polyalkylene glycol.

54. The conjugate of claim 53, wherein the polyalkylene glycol is polyethylene glycol.

55. The conjugate of claim 44, wherein the polymer is a polyalkylene glycol.

56. The conjugate of claim 55, wherein the polyalkylene glycol is polyethylene glycol.

57. The conjugate of claim 45, wherein the polymer is a polyalkylene glycol.

58. The conjugate of claim 57, wherein the polyalkylene glycol is polyethylene glycol.

59. The conjugate of claim 46, wherein the polymer is a polyalkylene glycol.

60. The conjugate of claim 9, wherein the polyalkylene glycol is polyethylene glycol.

61. The conjugate of claim 47, wherein the polymer is a polyalkylene glycol.

62. The conjugate of claim 61, wherein the polyalkylene glycol is polyethylene glycol.

63. The conjugate of claim 48, wherein the polymer is a polyalkylene glycol.

64. The conjugate of claim 63, wherein the polyalkylene glycol is polyethylene glycol.

65. The conjugate of claim 49, wherein the polymer is a polyalkylene glycol.

66. The conjugate of claim 65, wherein the polyalkylene glycol is polyethylene glycol.

67. The conjugate of claim 50, wherein the polymer is a polyalkylene glycol.

68. The conjugate of claim 67, wherein the polyalkylene glycol is polyethylene glycol.

* * * * *

UNITED STATES PATENT AND TRADEMARK OFFICE
CERTIFICATE OF CORRECTION

PATENT NO. : 7,442,370 B2  Page 1 of 1
APPLICATION NO. : 10/356264
DATED : October 28, 2008
INVENTOR(S) : Dinah Wen-Yee Sah et al.

It is certified that error appears in the above-identified patent and that said Letters Patent is hereby corrected as shown below:

Column 1
Line 7, delete "This application claims priority from" and insert -- This application is a CIP of --.

Column 88
Line 52, delete "A" and insert -- An isolated --.

Column 90
Line 21, delete "claim 9" and insert -- claim 59 --.

Signed and Sealed this

Fourteenth Day of July, 2009

JOHN DOLL
*Acting Director of the United States Patent and Trademark Office*